United States Patent [19]
Ditlow et al.

[11] Patent Number: 5,811,248
[45] Date of Patent: *Sep. 22, 1998

[54] ATHEROSCLEROTIC PLAQUE SPECIFIC ANTIGENS, ANTIBODIES THERETO, AND USES THEREOF

[75] Inventors: Charles C. Ditlow, Fremont; Francis W. Chen, San Francisco, both of Calif.; Emanuel Calenoff, Chicago, Ill.

[73] Assignee: Charter Ventures, Palo Alto, Calif.

[*] Notice: The term of this patent shall not extend beyond the expiration date of Pat. No. 5,786,455.

[21] Appl. No.: 480,434

[22] Filed: Jun. 7, 1995

Related U.S. Application Data

[60] Division of Ser. No. 336,525, Nov. 9, 1994, abandoned, which is a continuation-in-part of Ser. No. 53,451, filed as PCT/US94/04641 Apr. 26, 1994, which is a continuation-in-part of Ser. No. 828,860, Jan. 31, 1992, abandoned, which is a continuation-in-part of Ser. No. 388,129, Jul. 31, 1989, abandoned, which is a continuation-in-part of Ser. No. 67,995, Jun. 29, 1987, abandoned, which is a continuation of Ser. No. 67,993, Jun. 29, 1987, abandoned, which is a continuation-in-part of Ser. No. 67,986, Jun. 29, 1987, abandoned, which is a continuation-in-part of Ser. No. 876,841, Jun. 20, 1986, abandoned, which is a continuation-in-part of Ser. No. 871,811, Jun. 6, 1986, abandoned, which is a continuation-in-part of Ser. No. 846,401, Mar. 31, 1986, abandoned.

[51] Int. Cl.$^6$ .......................... G01N 33/574; G01N 33/53; C07K 16/18

[52] U.S. Cl. ................. 435/7.9; 435/7.1; 435/11; 435/7.92; 435/7.93; 424/9.6; 424/133.1; 424/134.1; 424/135.1; 424/178.1; 530/387.3; 530/388.1; 530/388.9; 530/391.1; 530/391.3

[58] Field of Search ................. 435/7.1, 11, 7.9, 435/7.92, 7.93; 530/387.3, 388.1, 388.9, 391.1, 391.3, 391.7; 436/518; 424/9.6, 133.1, 134.1, 135.1, 178.1

[56] References Cited

U.S. PATENT DOCUMENTS

| | | |
|---|---|---|
| 4,343,734 | 8/1982 | Lian et al. . |
| 4,816,567 | 3/1989 | Cabilly et al. . |
| 5,026,537 | 6/1991 | Daddona et al. . |
| 5,110,738 | 5/1992 | Takano et al. . |
| 5,196,324 | 3/1993 | Bumol et al. . |

FOREIGN PATENT DOCUMENTS 0 267 690   6/1988   European Pat. Off. .

OTHER PUBLICATIONS

Curtiss, L.K. and Witztum, J.L., Oct. 1983, "A Novel Method For Generating Region–Specific Monoclonal Antibodies To Modified Proteins," *The Journal of Clinical Investigation* 72(4):1427–1438.

Haberland, M.E., Jul. 8, 1988, "Malondialdehyde–Altered Protei Occurs in Atheroma Of Watanabe Heritable Hyperlipidemic Rabbits," *Science* 241:215–218.

Kimura, J. et al., 1986, "Monoclonal Antibodies Recognizing Lipid–Laden Cells And Extracellular Regions With Lipid–Deposits in Atherosclerotic Aorta," *Virchows Arch.* 410(2):159–164.

Shih, I.L. et al., Feb. 1990, "Focal Accumulation Of An Apolipoprotein B–Based Synthetic Oligopeptide In The Healing Rabbit Arterial Wall," *Proc. Nat'l. Acad. Sci.* 87:1436–1440.

*Primary Examiner*—Toni R. Scheiner
*Attorney, Agent, or Firm*—Albert P. Halluin; Howrey & Simon

[57] ABSTRACT

An antigen comprising 5,7 cholestadien-3β-ol (7-dehydrocholesterol) or a compound having a structure similar to 5,7 cholestadien-3β-ol and a quaternary ammonium salt is provided. Also provided is a method of generating an antibody using the aforementioned antigen, as well as antibodies produced thereby and fragments of such antibodies. The invention also provides a rat myeloma cell line Z2D3 73/30 1D10 and a murine-human chimeric monoclonal antibody produced thereby. A CDR-grafted antibody comprising a CDR region amino acid sequence from hybridoma Z2D3 or hybridoma Z2D3/3E5 and framework and constant region amino acid sequences from a human immunoglobulin is further provided. Also provided are methods for imaging atherosclerotic plaque, ablating atherosclerotic plaque, detecting and quantitatively determining in a sample an antigen indicative of the presence of atherosclerotic plaque, reducing the amount of atherosclerotic plaque in a blood vessel, and treating atherosclerosis in a subject. The invention also provides peptides having amino acid sequences which are the same or substantially the same as those of the aforementioned murine-human chimeric monoclonal antibody, as well as isolated nucleic acid sequences encoding therefore.

28 Claims, 52 Drawing Sheets

NON-SPECIFIC IgM MAb

FIG. 17A

```
              10v              20v              30v              40v              50v
VH1BACK(1,22)    AGGTSMARCTGCAGSAGTCWGG
Z2VH1(1,220)                          CTGCAGGAGTCWGGAGGAGGCTTGGTGCAACCTGGGGGGTCA
Z2VH12(1,218)                         CTGCAGGAGTCWGGAGGAGGCTTGGTGCAACCTGGGGGGTCA
Z2VH7(1,220)                          CTGCAGGAGTCTGGAGGAGGCTTGGTGCAACCTGGGGGGTCA
Z2VH9(1,218)                          CTGCAGGAGTCAGGAGGAGGCTTGGTGCAACCTGGGGGGTCG
Z2VH20A(1,237)                        CTGCAGGAGTCAGGAGGAGGCTTGGTGCAACCTGGGGGGTCA
Z2VH2(1,220)                                           AGGCTTGGTGCAACCTGGGGGGTCA
Z2VH5(1,220)                                           AGGCTTGGTGCAACCTGGGGGGTCA
Z2VH6(1,220)                                           AGGCTTGGTGCAACCTGGGGGGTCA
Z2VH8(1,219)                                              GGCTTGGTGCAACCTGGGGGGTCA
Z2VH10(1,218)                                               GCTTGGTGCAACCTGGGGGGTCA consensus        AGGTSMARCTGCAGGAGTCWGGAGGAGGCTTGGTGCAACCTGGGGGGTCA
```

FIG. 17B

```
                      60v        70v        80v        90v        100v
Z2VH1(1,220)'    CGGGGACTCTCTTGTGAAGGCTCAGGGTTTACTTTTAGTGGCTTCTGGAT
Z2VH12(1,218)'   CGGGGACTCTCTTGTGAAGGCTCAGGGTTTACTTTTAGTGGCTTCTGGAT
Z2VH7(1,220)'    CGGGGACTCTCTTGTGAAGGCTCAGGGCTTACTTTTAGTGGCTTCTGGAT
Z2VH9(1,218)'    CGGGGACTCTCTTGTGAAGGCTCAGGGTTTACTTTTAGTGGCTTCTGGAT
Z2VH20A(1,237)   CGGGGACTCTCTTGTGAAGGCTCAGGGTTTACTTTTAGTGGCTTCTGGAT
Z2VH2(1,220)     CGGGGACTCTCTTGTGAAGGCTCAGGGTTTACTTTTAGTGGCTTCTGGAT
Z2VH5(1,220)     CGGGGACTCTCTTGTGAAGGCTCAGGGTTTACTTTTAGTGGCTTCTGGAT
Z2VH6(1,220)     CGGGGACTCTCTTGTGAAGGCTCAGGGTTTACTTTTAGTGGCTTCTGGAT
Z2VH8(1,219)     CGGGGACTCTCTTGTGAAGGCTCAGGGTTTACTTTTAGTGGCTTCTGGAT
Z2VH10(1,218)    CGGGGACTCTCTTGTGAAGGCTCAGGGTTTACTTTTAGTGGCTTCTGGAT consensus        CGGGGACTCTCTTGTGAAGGCTCAGGGTTTACTTTTAGTGGCTTCTGGAT
```

FIG. 17C

```
                    110v         120v         130v         140v         150v
Z2VH1(1,220)   GAGCTGGGTTCGACAGACACCTGGGAAGACCCTGGAGTGGATTGGAGACA
Z2VH12(1,218)  GAGCTGGGTTCGACAGACACCTGGGAAGACCCTGGAGTGGATTGGAGACA
Z2VH7(1,220)   GAGCTGGGTTCGACAGACACCTGGGAAGACCCTGGAGTGGATTGGAGACA
Z2VH9(1,218)   GAGCTGGGTTCGACAGACACCTGGGAAGACCCTGGAGTGGATTGGAGACA
Z2VH20A(1,237) GAGCTGGGTTCGACAGACACCTGGGAAGACCCTGGAGTGGATTGGAGACA
Z2VH2(1,220)   GAGCTGGGTTCGACAGACACCTGGGAAGACCCTGGAGTGGATTGGAGACA
Z2VH5(1,220)   GAGCTGGGTTCGACAGACACCTGGGAAGACCCTGGAGTGGATTGGAGACA
Z2VH6(1,220)   GAGCTGGGTTCGACAGACACCTGGGAAGACCCTGGAGTGGATTGGAGACA
Z2VH8(1,219)   GAGCTGGGTTCGACAGACACCTGGGAAGACCCTGGAGTGGATTGGAGACA
Z2VH10(1,218)  GAGCTGGGTTCGACAGACACCTGGGAAGACCCTGGAGTGGATTGGAGACA consensus      GAGCTGGGTTCGACAGACACCTGGGAAGACCCTGGAGTGGATTGGAGACA
```

FIG. 17D

```
                    160v         170v         180v         190v         200v
Z2VH1(1,220)'    TTAATTCTGATGGCAGTGCAATAAACTACGCACCATCCATAAAGGATCGA
Z2VH12(1,218)'   TTAATTCTGATGGCAGTGCAATAAACTACGCACCATCCATAAAGGATCGA
Z2VH7(1,220)'    TAATTCTGATGGCAGTGCAATAAACTACGCACCATCCATAAAGGATCGA
Z2VH9(1,218)'    TTAATTCTGATGGCAGTGCAATAAACTACGCACCATCCATAAAGGATCGA
Z2VH20A(1,237)   CTAATTCTGATGGCAGTGCAATAAACTACGCACCATCCATAAAGGATCGA
Z2VH2(1,220)     TTAATTCTGATGGCAGTGCAATAAACTACGCACCATCCATAAAGGATCGA
Z2VH5(1,220)     TTAATTCTGATGGCAGTGCAATAAACTACGCACCATCCATAAAGGATCGA
Z2VH6(1,220)     TTAATTCTGATGGCAGTGCAATAAACTACGCACCATCCATAAAGGATCGA
Z2VH8(1,219)     TTAATTCTGATGGCAGTGCAATAAACTACGCACCATCCATAAAGGATCGA
Z2VH10(1,218)    TTAATTCTGATGGCAGTGCAATAAACTACGCACCATCCATAAAGGATCGA consensus        TTAATTCTGATGGCAGTGCAATAAACTACGCACCATCCATAAAGGATCGA
```

FIG. 17E

```
                    210v              220v              230v              240v              250v
Z2VH1(1,220)'      TTCACTATCTTCAGAGACAATGACAAGA
Z2VH12(1,218)'     TTCACTATCTTCAGAGACAATGACAA
Z2VH7(1,220)'      TTCACTATCTTCAGAGACAATGACAAGA
Z2VH9(1,218)'      TTCACTATCTTCAGAGACAATGACAA
Z2VH20A(1,237)     TTCACTATCTTCAGAGACAATGACAAGAGCACCCTGTACCTGCAG
Z2VH2(1,220)       TTCACTATCTTCAGAGACAATGACAAGAGCACCCTGTACCTGCAG
Z2VH5(1,220)       TTCACTATCTTCAGAGACAATGACAAGAGCACCCTGTACCTGCAG
Z2VH6(1,220)       TTCACTATCTTCAGAGACAATGACAAGAGCACCCTGTACCTGCAG
Z2VH8(1,219)       TTCACTATCTTCAGAGACAATGACAAGAGCACCCTGTACCTGCAG
Z2VH10(1,218)      TTCACTATCTTCAGAGACAATGACAAGAGCACCCTGTACCTGCAG
Z2VH21(1,147)      TTCACTATCTTCAGAGACAATGACAAGAGCACCCTGTACCTGCAG      CTGCAGATGAG
Z2VH17(1,114)'                                                                              CTGCAGATGAG concensus          TTCACTATCTTCAGAGACAATGACAAGAGCACCCTGTACCTGCAGATGAG
```

FIG. 17F

```
              260v       270v       280v       290v       300v
ZZVH21(1,147) CAATGTGCGATCTGAGGACACAGCCACGTATTTCTGTATGAGATATGATG
ZZVH17(1,114)'CAATGTGCGATCTGAGGACACAGCCACGTATTTCTGTATGAGATATGATG consensus     CAATGTGCGATCTGAGGACACAGCCACGTATTTCTGTATGAGATATGATG 310v       320v       330v       340v       350v
ZZVH21(1,147) GTTACTACTGGTACTTCGATGTCTGGGGCGCAGGGACCACGGTCACCGTC
ZZVH17(1,114)'GTTACTACTGGTACTTCGATGTCTGGGGCGCAGGGACCACGGTCACCGTC consensus     GTTACTACTGGTACTTCGATGTCTGGGGCGCAGGGACCACGGTCACCGTC 360v       370v       380v       390v       400v
ZZVH21(1,147) TCCTCAGAGAGTCAGTCCTTCCCAA--GTCTTAAGCTT
ZZVH17(1,114)'TCC
CM1FOR(1,34)'          GAGAGTCAGTCAGTCCTTCCCAAATGTCTTAAGCTTCC consensus     TCCTCAGAGAGTCAGTCCTTCCCAAatGTCTTAAGCTTCC
```

```
                                                        60
              PMH M  P       ESASBB  M  P  HF
              SNN N  L       CEPCSS  A  L  EN I
              TLF L  E       RCYRAA  E  E  FN
              111 1  1       2111JJ  3  1  11
                                      ///
AGGTSMARCTGCAGGAGTCWGGAGGAGGCTTGGTGCAACCTGGGGGGTCACGGGGACTCT
----.----+----.----+----.----+----.----+----.----+----.----+
TCCASKTYGACGTCCTCAGWCCTCCTCCGAACCACGTTGGACCCCCAGTGCCCCTGAGA v  k/q l  q  e  s  g  g  g  l  v  q  p  g  g  s  r  g  l  s
----.----+----.----+----.----+----.----+----.----+----.----+
```

```
              D                    A      FT     ESBB
              D                    L      OA     CESS
              E                    U      KQ     RCAA
              1                    1      11     21JJ
                                          /      //
                                                          120
CTTGTGAAGGCTCAGGGTTTACTTTTAGTGGCTTCTGGATGAGCTGGGTTCGACAGACAC
----+----.----+----.----+----.----+----.----+----.----+----.
GAACACTTCCGAGTCCCAAATGAAAATCACCGAAGACCTACTCGACCCAAGCTGTCTGTG c  e  g  s  g  f  t  f  s  g  f  w  m  s  w  v  r  q  t  p
```

FIG. 18C

```
AS B      BSEBBEASMA       B     AM                    F
PC B      SECBSCPCBL       S     SS                    O
YR V      ACPSARYROW       M     EE                    K
11 2      J111J21122       2     11                    1
 /         ////             /                                          180
         CTGGGAAGACCCTGGAGTGGATTGGAGACATTAATTCTGATGGCAGTGCAATAAACTACG
         ---------+---------+---------+---------+---------+---------+
         GACCCTTCTGGGACCTCACCTAACCTCTGTAATTAAGACTACCGTCACGTTATTTGATGC g  k  t  l  e  w  i  g   d  i  n  s  d  g  s  a  i  n  y  a
```

FIG. 18D

```
         BMDDCTTHM      A    B            HN    R
         IBPPLAFNB      L    S            GS    S
         NONNAQIFO      W    M            IP    A
         112111112      2    2            A2    1
          / //                                /
       ┌──────────                                         ──────
       CACCATCCATAAAGGATCGATTCACTATCTTCAGAGACAATGACAAGAGCACCCTGTACC
       ----+----.----+----.----+----.----+----.----+----.----+   240
       GTGGTAGGTATTTCCTAGCTAAGTGATAGAAGTCTCTGTTACTGTTCTCGTGGGACATGG
       ----+----.----+----.----+----.----+----.----+----.----+
       └──────────                                         ──────
         p  s  i  k  d    r   f  t  i  f  r  d  n  d  k  s  t  l  y  l
       ----+----.----+----.----+----.----+----.----+----.----+
```

FIG. 18E

```
P  B              M MDD  D              M                    M
S  S              N BPP  D              A                    A
T  P              L ONN  E              E                    E
1  1              1 121  1              2                    3
                            /                                              300
TGCAGATGAGCAATGTGTGCGATCTGAGGACACAGCCACGTATTTCTGTATGAGA TATGATG
---+----+----+----+----+----+----+----+----+----+----+- ---+---+
ACGTCTACTCGTTACACGCTAGACTCCTGTGTCGGTGCATAAAGACATACTCTA TACTAC q  m  s  n  v  r  s  e  d  t  a  t  y  f  c  m  r   y  d  g
---+----+----+----+----+----+----+----+----+----+---- +---+---+
```

FIG. 18F

```
           R   T                H H    ANAFDDSBBBMH     BD         AH
           S   A                I H    VLSISSESSSAP     SD         LN      →CH1
           A   Q                N A    AAUNAACAATEH     ME         WF
           1   1                P 1    241111JJE31      21         21          360
                                       ////////                     /
         GTTACTACTGGTACTTCGATGTCTGGGGGCGCAGGGACCACGGTCACCGTCTCCTCAGAGA
         ----+----.----+----.----+----.----+----.----+----.----+----.
         CAATGATGACCATGAAGCTACAGACCCCCGCGTCCCTGGTGCCAGTGGCAGAGGAGTCTCT
          y  y  w  y  f  d  v  w  g  a  g  t  t  v  t  v  s  s  e  s
```

GTCAGTCCTTCCCAAATGTCTTAAGCTTCC
        ----.----+----.----+----.----+  390
        CAGTCAGGAAGGGTTTACAGAATTCGAAGG q  s  f  p  n  v
        ----.----+----.----+----.----+
```

FIG. 19

```
              10v           20v          30v          40v          50v
Z2D3MUVH   XVXLQESGGGLVQPGGSRGLSCEGSGFTFSGFWMSWVRQTPGKTLEWIGDI
             V L ESGGGLVQPGGS  LSC   SGF FS   WMS WVRQ PGK LEWIG  I
MUVHIIIB   EVKLLESGGGLVQPGGSLKLSCAASGFDFSRYWMSWVRQAPGKGLEWIGEI
              10▲▲▲         20▲▲▲▲    30▲▲▲      40▲       50^

60v           70v          80v          90v          100v
Z2D3MUVH   N---SDGSAINYAPSIKDRFTIFRDNDKSTLYLQMSNVRSEDTATYFCMRYD
             N D S INY PS KD  F I RDN K TLYLQMS VRSEDTA Y C R
MUVHIIIB   NPKADSSTINYTPSLKDKFIISRDNAKNTLYLQMSKVRSEDTALYYCARL-
              60^▲          70▲       80^       90^           100^

110v
Z2D3MUVH   GYYWYFDVWGAGTTTVTVSS
             GYY YF     WG GTTVTVSS
MUVHIIIB   GYYGYFAYWGQGTTVTVSS
              110          120▲▲▲
```

FIG. 20A

```
                    10v        20v        30v        40v        50v
VK1BACK(1,24)     GACATTCAGCTGACCCAGTCTCCA
Z2VK34(1,291)              CTGACCCAGTCTCCATCCTCCATGTATGCATCGCTGGGAGA
Z2VK10(1,140)              CTGACCCAGTCTCCATCCTCCATGTATGCATCGCTGGGAGA
Z2VK17(1,92)               CTGACCCAGTCTCCATCCTCCATGTATGCATCGCTGGGAGA
Z2VK23(1,152)              CTGACCCAGTCTCCATCCTCCATGTATGCATCGCTGGGAGA
Z2VK3(1,141)                        CTCCATCCTCCATGTATGCATCGCTGGGAGA
Z2VK11A(1,84)                         TCCATCCTCCATGTATGCATCGCTGGGAGA
Z2VK7(1,140)                          TCCATCCTCCATGTATGCATCGCTGGGAGA
Z2VK8A(1,140)                         TCCATCCTCCATGTATGCATCGCTGGGAGA
Z2VK28(1,265)                                       TGCATCGCTGGGAGA
Z2VK29(1,265)                                       TGCATCGCTGGGAGA
Z2VK30(1,265)                                       TGCATCGCTGGGAGA
Z2VK31(1,264)                                        GCATCGCTGGGAGA
Z2VK32(1,264)                                        GCATCGCTGGGAGA
Z2VK36(1,263)'                                        CATCGCTGGGAGA
Z2VK25(1,260)'                                          CGCTGGGAGA consensus         GACATTCAGCTGACCCAGTCTCCATCCTCCATGTATGCATCGCTGGGAGA
```

FIG. 20B

```
                    60v         70v         80v         90v        100v
Z2VK34(1,291)'  GAGAGTCACTATCACTTGCAAGGCGAGTCAGGACATTAAAAGCTATTTAA
Z2VK10(1,140)'  GAGAGTCACTATCACTTGCAAGGCGAGTCAGGACATTAAAAGCTATTTAA
Z2VK17(1,92)'   GAGAGTCACTATCACTTGCAAGGCGAGTCAGGACATTAAAAGCTATTTAA
Z2VK23(1,152)   GAGAGTCACTATCACTTGCAAGGCGAGTCAGGACATTAAAAGCTATTTAA
Z2VK3(1,141)    GAGAGTCACTATCACTTGCAAGGCGAGTCAGGACATTAAAAGCTATTTAA
Z2VK11A(1,84)   GAGAGTCACTATCACTTGCAAGGCGAGTCAGGACATTAAAAGCTATTTAA
Z2VK7(1,140)    GAGAGTCACTATCACTTGCAAGGCGAGTCAGGACATTAAAAGCTATTTAA
Z2VK8A(1,140)   GAGAGTCACTATCACTTGCAAGGCGAGTCAGGACATTAAAAGCTATTTAA
Z2VK28(1,265)   GAGAGTCACTATCACTTGCAAGGCGAGTCAGGACATTAAAAGCTATTTAA
Z2VK29(1,265)   GAGAGTCACTATCACTTGCAAGGCGAGTCAGGACATTAAAAGCTATTTAA
Z2VK30(1,265)   GAGAGTCACTATCACTTGCAAGGCGAGTCAGGACATTAAAAGCTATTTAA
Z2VK31(1,264)   GAGAGTCACTATCACTTGCAAGGCGAGTCAGGACATTAAAAGCTATTTAA
Z2VK32(1,264)   GAGAGTCACTATCACTTGCAAGGCGAGTCAGGACATTAAAAGCTATTTAA
Z2VK36(1,263)'  GAGAGTCACTATCACTTGCAAGGCGAGTCAGGACATTAAAAGCTATTTAA
Z2VK25(1,260)'  GAGAGTCACTATCACTTGCAAGGCGAGTCAGGACATTAAAAGCTATTTAA
Z2VK18B(1,88)'                   AAGGGCGAGTCAGGACATTAAAAGCTATTTAA consensus       GAGAGTCACTATCACTTGCAAGGCGAGTCAGGACATTAAAAGCTATTTAA
```

FIG. 20C

```
                  110v       120v       130v       140v       150v
Z2VK34(1,291)'  GCTGGTACCAGCAGAAACCATGGAAATCTCCTAAGACCCTGATCTATTAT
Z2VK10(1,140)'  GCTGGTACCAGCAGAAACCATGGAAATCTCCTAAGACCCTGATCTATTA
Z2VK17(1,92)'   G
Z2VK23(1,152)   GCTGGTACCAGCAGAAACCATGGAAATCTCCTAAGACCCTGATCTATTAT
Z2VK3(1,141)    GCTGGTACCAGCAGAAACCATGGAAATCTCCTAAGACCCTGATCTATTAT
Z2VK11A(1,84)   GCTG
Z2VK7(1,140)    GCTGGTACCAGCAGAAACCATGGAAATCTCCTAAGACCCTGATCTATTAT
Z2VK8A(1,140)   GCTGGTACCAGCAGAAACCATGGAAATCTCCTAAGACCCTGATCTATTAT
Z2VK28(1,265)   GCTGGTACCAGCAGAAACCATGGAAATCTCCTAAGACCCTGATCTATTAT
Z2VK29(1,265)   GCTGGTACCAGCAGAAACCATGGAAATCTCCTAAGACCCTGATCTATTAT
Z2VK30(1,265)   GCTGGTACCAGCAGAAACCATGGAAATCTCCTAAGACCCTGATCTATTAT
Z2VK31(1,264)   GCTGGTACCAGCAGAAACCATGGAAATCTCCTAAGACCCTGATCTATTAT
Z2VK32(1,264)   GCTGGTACCAGCAGAAACCATGGAAATCTCCTAAGACCCTGATCTATTAT
Z2VK36(1,263)'  GCTGGTACCAGCAGAAACCATGGAAATCTCCTAAGACCCTGATCTATTAT
Z2VK25(1,260)'  GCTGGTACCAGCAGAAACCATGGAAATCTCCTAAGACCCTGATCTATTAT
Z2VK18B(1,88)'  GCTGGTACCAGCAGAAACCATGGAAATCTCCTAAGACCCTGATCTATTAT consensus       GCTGGTACCAGCAGAAACCATGGAAATCTCCTAAGACCCTGATCTATTAT
```

FIG. 20D

```
                 160v       170v       180v       190v       200v
Z2VK34(1,291)'   GCAACAAGCTTGGCAGATGGGGTCCCATCAAGATTCAGTGGCAGTGGATC
Z2VK23(1,152)    GCAACAAGCTT
Z2VK3(1,141)     GCAACAAGCT
Z2VK7(1,140)     GCAACAAGCT
Z2VK8A(1,140)    GCAACAAGCT
Z2VK28(1,265)    GCAACAAGCTTGGCAGATGGGGTCCCATCAAGATTCAGTGGCAGTGGATC
Z2VK29(1,265)    GCAACAAGCTTGGCAGATGGGGTCCCATCAAGATTCAGTGGCAGTGGATC
Z2VK30(1,265)    GCAACAAGCTTGGCAGATGGGGTCCCATCAAGATTCAGTGGCAGTGGATC
Z2VK31(1,264)    GCAACAAGCTTGGCAGATGGGGTCCCATCAAGATTCAGTGGCAGTGGATC
Z2VK32(1,264)    GCAACAAGCTTGGCAGATGGGGTCCCATCAAGATTCAGTGGCAGTGGATC
Z2VK36(1,263)'   GCAACAAGCTTGGCAGATGGGGTCCCATCAAGATTCAGTGGCAGTGGATC
Z2VK25(1,260)'   GCAACAAGCTTGGCAGATGGGGTCCCATCAAGATTCAGTGGCAGTGGATC
Z2VK18B(1,88)'   GCAACAA
Z2VK19(1,203)              AGCTTGGCAGATGGGGTCCCATCAAGATTCAGTGGCAGTGGATC
Z2VK20(1,204)              AGCTTGGCAGATGGGGTCCCATCAAGATTCAGTGGCAGTGGATC
Z2VK16(1,175)'             AGCTTGGCAGATGGGGTCCCATCAAGATTCAGTGGCAGTGGATC
Z2VK18A(1,167)'              CTTGGCAGATGGGGTCCCATCAAGATTCAGTGGCAGTGGATC consensus        GCAACAAGCTTGGCAGATGGGGTCCCATCAAGATTCAGTGGCAGTGGATC
```

FIG. 20E

| | 210v | 220v | 230v | 240v | 250v |
|---|---|---|---|---|---|
| Z2VK34(1,291)' | TGGGCAAGATTATTCTCTAACCATCAGCAGCCTGGAGTCTGACGATACAG |
| Z2VK28(1,265) | TGGGCAAGATTATTCTCTAACCATCAGCAGCCTGGAGTCTGACGATACAG |
| Z2VK29(1,265) | TGGGCAAGATTATTCTCTAACCATCAGCAGCCTGGAGTCTGACGATACAG |
| Z2VK30(1,265) | TGGGCAAGATTATTCTCTAACCATCAGCAGCCTGGAGTCTGACGATACAG |
| Z2VK31(1,264) | TGGGCAAGATTATTCTCTAACCATCAGCAGCCTGGAGTCTGACGATACAG |
| Z2VK32(1,264) | TGGGCAAGATTATTCTCTAACCATCAGCAGCCTGGAGTCTGACGATACAG |
| Z2VK36(1,263)' | TGGGCAAGATTATTCTCTAACCATCAGCAGCCTGGAGTCTGACGATACAG |
| Z2VK25(1,260)' | TGGGCAAGATTATTCTCTAACCATCAGCAGCCTGGAGTCTGACGATACAG |
| Z2VK19(1,203) | TGGGCAAGATTATTCTCTAACCATCAGCAGCCTGGAGTCTGACGATACAG |
| Z2VK20(1,204) | TGGGCAAGATTATTCTCTAACCATCAGCAGCCTGGAGTCTGACGATACAG |
| Z2VK16(1,175)' | TGGGCAAGATTATTCTCTAACCATCAGCAGCCTGGAGTCTGACGATACAG |
| Z2VK18A(1,167)' | AAGATTATTCTCTAACCATCAGCAGCCTGGAGTCTGACGATACAG |
| Z2VK8B(1,154)' | TGGGCAAGATTATTCTCTAACCATCAGCAGCCTGGAGTCTGACGATACAG | consensus  TGGGCAAGATTATTCTCTAACCATCAGCAGCCTGGAGTCTGACGATACAG

FIG. 20F

|  | 260v | 270v | 280v | 290v | 300v |
|---|---|---|---|---|---|
| Z2VK34(1,291)' | CAACTTATTACTGTCTACAGCATGGTGAGAGCCCGCTCACGTTCGGTGCT |
| Z2VK28(1,265)' | CAACTTATTACTGTCTACAGCATGGTGAGAGCCCGCTCACGTTCGGTGCT |
| Z2VK29(1,265) | CAACTTATTACTGTCTACAGCATGGTGAGAGCCCGCTCACGTTCGGTGCT |
| Z2VK30(1,265) | CAACTTATTACTGTCTACAGCATGGTGAGAGCCCGCTCACGTTCGGTGCT |
| Z2VK31(1,264) | CAACTTATTACTGTCTACAGCATGGTGAGAGCCCGCTCACGTTCGGTGCT |
| Z2VK32(1,264) | CAACTTATTACTGTCTACAGCATGGTGAGAGCCCGCTCACGTTCGGTGCT |
| Z2VK36(1,263)' | CAACTTATTACTGTCTACAGCATGGTGAGAGCCCGCTCACGTTCGGTGCT |
| Z2VK25(1,260)' | CAACTTATTACTGTCTACAGCATGGTGAGAGCCCGCTCACGTTCGGTGCT |
| Z2VK19(1,203) | CAACTTATTACTGTCTACAGCATGGTGAGAGCCCGCTCACGTTCGGTGCT |
| Z2VK20(1,204) | CAACTTATTACTGTCTACAGCATGGTGAGAGCCCGCTCACGTTCGGTGCT |
| Z2VK16(1,175)' | CAACTTATTACTGTCTACAGCATGGTGAGAGCCCGCTCACGTTCGGTGCT |
| Z2VK18A(1,167)' | CAACTTATTACTGTCTACAGCATGGTGAGAGCCCGCTCACGTTCGGTGCT |
| Z2VK8B(1,154)' | CAACTTATTACTGTCTACAGCATGGTGAGAGCCCGCTCACGTTCGGTGCT | consensus  CAACTTATTACTGTCTACAGCATGGTGAGAGCCCGCTCACGTTCGGTGCT

FIG. 20G

```
              310v        320v        330v        340v        350v
Z2VK19(1,203)  GGGACCAAGCTGGAGCTGAAACGGGGCTGATGCTGCACCAACTGTATCCA-
Z2VK20(1,204)  GGGACCAAGCTGGAGCTGAAACGGGGCTGATGCTGCACCAACTGTATCCAT
Z2VK16(1,175)' GGGACCAAGCTGGAGCTGAAACGGGGCTGATG
Z2VK18A(1,167)' GGGACCAAGCTGGAGCTGAAACGGG
Z2VK8B(1,154)' GGGACCAAGCTGGAGCTGAAACGGGGCTGATGCTGCACCAACTGTATCCAT
CK2F0R(1,32)'                                  GCTGCACCAACTGTATCCAT consensus      GGGACCAAGCTGGAGCTGAAACGGGGCTGATGCTGCACCAACTGTATCCAT
```

FIG. 20H

```
              360v        370v        380v        390v        400v
Z2VK19(1,203)  CTTCAAGCTT
Z2VK20(1,204)  CTTCAAGCTT
Z2VK8B(1,154)' CTTCAAGCT
CK2F0R(1,32)'  CTTCAAGCTTCC consensus      CTTCAAGCTTCC
```

FIG. 21A

```
P  P  H D  M N  N DDAPBAPNNHAND                    BXMDD
S  L  N D  N L  L RRSSAPSLSASLD                    IHBPP
T  E  F E  L A  A AAUSNASAPEUAE                    NOONN
1  1  1 1  1 3  3 2212114231 41                    12121
                      //////////                     ///
CTGCAGSAGTCWGGACTCAGAGCATGGAGACATGAGGGCCCCTGCTCAGTTTTTTGGGATCTTG
----+----:----+----.----+----:----+----.----+----:----+----.    60
GACGTCSTCAGWCCTGAGTCGTACCTGTACTCCCGGGGACGAGTCAAAAAACCCTAGAAC m   r   a   p   a   q   f   f   g   i   l m   r   a   p   a   q   f   f   g   i   l
```

FIG. 21B

```
        E AS          M         F         T         B    A    N
        C PC          A         O         T         S    L    L
        R YR          E         K         H         M    W    A
        2 11          3         1         1         2    2    3
          /                                                          120
TTGCTCTGGTTTCCAGGTATCAGAGATGTGACATCAAGATGACCCAGTCTCCATCCTCCATG
----+----+----+----+----+----+----+----+----+----+----+----+
AACGAGACCAAAGGTCCATAGTCTCTACACTGTAGTTCTACTGGGTCAGAGGTAGGAGGTAC l  l  w  f  p  g  i  r  c  d  i  k  m  t  q  s  p  s  s  m
```

FIG. 21C

```
  M  NA   S   HM   P           H    P   M   A
  N  SV   F   NA   L           N    L   S   L
  L  IA   A   FE   E           F    E   E   V
  1  13   N   13   1           1    1   1   1
                                              180
TATGCATCGCTGGGAGAGAGTCACTATCACTTGCAAGGCGAGTCAGGACATTAAAAGC
----+----+----+----+----+----+----+----+----+----+----+----+
ATACGTAGCGACCCTCTCTCAGTGATAGTGAACGTTCCGCTCAGTCCTGTAATTTTCG y  a s  l  g  e  r  v  t  i  t  c  k  a  s  q  d  i  k  s
```

FIG. 21D

```
            M A   BANRKE    DSNDSBBTN       D   E MDD
            S L   ASLSPC    STCSESSTL       D   C BPP
            E U   NPAAN1    AYOACAAHA       E   P ONN
            1 1   114115    11111JJ23       1   1 121
                  / / /     / / / / /               /
                                                                          240
         TATTTAAGCTGGTACCAGCAGAGAAACCATGGAAATCTCCTAAGACCCTGATCTATTATGCA
         ----+----.----+----.----+----.----+----.----+----.----+----.
         ATAAATTCGACCATGGTCGTCTTTGGTACCTTTAGAGGATTCTGGGACTAGATAATACGT
          y l  s  w  y  q  q  k  p  w  k  s  p  k  t  l  i  y  y  a

```
H A           DNPPAANF    TH      BXMDD
I L           RLPSVSLI    FN      IHBPP
N U           AAUSAUAN    IF      NOONN
3 1           24112141    11      12121
             / ////       /       ///
      ACAAGCTTGGCAGATGGGGTCCCATCAAGATTCAGTGGGCAGTGGGATCTGGGCAAGATTAT
      ---+----.----+----.----+----.----+----.----+----.----+          300
      TGTTCGAACCGTCTACCCCAGGGTAGTTCTAAGTCACCGTCACCCTAGACCCGTTCTAATA t  s  l  a  d   g  v  p  s  r  f  s  g  s  g  s  g  q  d  y

```
        E   F  E  AS  H   B   P          A
        C   N  C  PC  N   B   L          C
        1   U  R  YR  F   V   E          C
        5   H  2  11  1   1   1          1
                              /
TCTCTAACCATCAGCAGCCTGGAGTCTGACGATACAGCAACTTATTACTGT CTACAGCAT
----+----.----+----.----+----.----+----.----+----.----+----
AGAGATTGGTAGTCGTCGGACCTCAGACTGCTATGTCGTTGAATAATGACA GATGTCGTA
                                                                360
 s  l  t  i  s  s  l  e  s  d  d  t  a  t  y  y  c    l  q  h
----+----.----+----.----+----.----+----.----+----.----+----
```

FIG. 21G

```
        N      BNAHT M           ANAF       A      A   A SB      F
        L      ASCPT A           VLSI       L      L   L FB      N
        A      NPIHH E           AAUN       U      U   U AV      U
        3      22112 2           2411       1      1   1 N1      H
                //                /                        /
GGTGAGAGAGCCCGCTCACGTTCGGTGCTGGGACCAAGCTGGAGCTGAAACGGGCTGATGCT
----+----.----+----.----+----.----+----.----+----.----+----.   420
CCACTCTCGGGCGAGTGCAAGCCACGACCCTGGTTCGACCTTCGACTTTGCCCGACTACGA
                                                     ─CK
 g  e  s  p  l  t  f  g  a  g  t  k  l  e  l  k  r  a  d  a
```

FIG. 21H

```
MBO2                          HAILNU31
GCACCAACTGTATCCATCTTCAAGCTTCC          449
---:----.----+----:----.----+
CGTGGTTGACATAGGTAGAAGTTCGAAGG
 a  p  t  v  s  i  f
```

```
                    10v              20v               30v              40v              50v
Z2D3MUVK   DIQLTQSPSSMYASLGERVTITC KASQDIKSYLS WYQQKPWKSPKTLIYYA
           DIQ TQSPSS    ASLG RVTITC  ASQDI       YL  WYQQKP    PK  LIYYA
MUVKV      DIQMTQSPSSLSASLGDRVTITC RASQDISNYLN WYQQKPGGTPKLLIYYA
                     ▲10^            ▲20^           ▲30^           ▲40^  ▲50^

60v              70v               80v              90v             100v
Z2D3MUVK   TSLAD GVPSRFSGSGSGQDYSLTISSLESDDTATYYC LQHGESPLT FGAGT
               L GVPSRFSGSGSG DYSLTISSLE   D ATY  Q    Q       TFG GT
MUVKV      SRLHS GVPSRFSGSGSGTDYSLTISSLEQEDIATYFC QQGNSLPRT FGGGT
           ▲60^▲▲▲             ▲70^

CHIMERIC Z2D3 F(ab')$_2$

NON-SPECIFIC HUMAN F(ab')$^2$

CHIMERIC Z2D3 F(ab')$_2$

NON-SPECIFIC HUMAN F(ab')$_2$

CHIMERIC Z2D3 F(ab')$_2$

NON-SPECIFIC HUMAN F(ab')$_2$

ATHEROSCLEROTIC PLAQUE SPECIFIC ANTIGENS, ANTIBODIES THERETO, AND USES THEREOF

This is a division of application Ser. No. 08/336,525 filed Nov. 9, 1994, now abandoned, which is a continuation in part of PCT/US94/04641, filed Apr. 26, 1994, which is a continuation in part of U.S. Ser. No. 08/053,451, filed Apr. 26, 1993; which is a continuation in part of U.S. Ser. No. 07/828,860, filed Jan. 31, 1992, now abandoned; which is a continuation in part of U.S. Ser. No. 07/388,129, filed Jul. 31, 1989, now abandoned; which was a continuation in part of U.S. Ser. No. 07/067,995, filed Jun. 29, 1987, now abandoned; which was a continuation U.S. Ser. No. 07/067,993, filed Jun. 29, 1987, now abandoned; which was a continuation in part of U.S. Ser. No. 07/067,986, filed Jun. 29, 1987, now abandoned; which was a continuation in part of U.S. Ser. No. 06/876,841, filed Jun. 20, 1986, now abandoned; which was a continuation in part of U.S. Ser. No. 06/871,811, filed Jun. 6, 1986, now abandoned; which was a continuation in part of U.S. Ser. No. 06/846,401, filed Mar. 31, 1986, now abandoned.

BACKGROUND OF THE INVENTION

Atherosclerosis is the progressive narrowing of the lumen (inner passageway) of arterial blood vessels by layers of plaque (fatty and fibrous tissues). Atherosclerosis can occur in any artery. In coronary arteries, it may result in heart attacks; in cerebral arteries it may result in strokes; and in peripheral arteries it may result in gangrene of the extremities. Atherosclerosis is the single largest medical problem currently facing the United States and other developed countries. Approximately forty million people in the United States are at risk for atherosclerosis. However, only six million people in the United States show overt signs of the disease. The rest remain undiagnosed until the disease manifests itself symptomatically, in the worst case as heart attack or stroke. Heart attack and stroke, respectively, represent the first and third leading causes of death in the United States. Over five hundred thousand people die of heart attacks every year, and a significant sub-group of these patients expire without warning. The endothelium is located between the blood and arterial tissue and serves as a barrier against the accumulation of blood components in the vascular wall. Formation of atherosclerotic lesions in the subendothelium is associated with major coronary artery disease and stroke. The causes and detection of such lesions have been intensely investigated.

Atherosclerosis is a complex process, and precisely how it begins or what causes it is not known. However, endothelial injury is believed to be an initial step in the formation of atherosclerotic lesions, and may be caused by hemodynamic strain, hypercholesterolemia, hypertension or immune complex disease. Endothelial injury leads to cholesterol and lipid accumulation, intimal thickening, smooth muscle cell proliferation, and formation of connective tissue fibers. Gradually, the build-up of fatty deposits and the proliferation of the smooth muscle cells lead to the formation of plaques which eventually narrow and block the artery.

Although atherosclerosis is generally a diffuse disease, human coronary atherosclerosis lends itself to bypass procedures because the major site of plaque formation is usually proximally distributed. As a result, direct coronary artery bypass has become the most frequently selected form of myocardial revascularization. The aorta-coronary artery vein graft or the internal mammary artery graft have become technically standardized and have high, long-term patency rates. These long-term results, however, can be compromised by progressive atherosclerosis distal to the graft anastomosis. Other cases are inoperable because of distal disease. Previously, distal lesions have been ignored, or, in selected cases, treated by endarterectomy although neither approach has proved entirely satisfactory.

Most existing procedures for the diagnosis and treatment of atherosclerosis are invasive, costly, and of limited effectiveness in a significant percentage of cases.

Prior to the subject invention, radioimaging of atherosclerotic plaque using an antibody which specifically binds to an atherosclerotic plaque-specific antigen was unknown, although radioimaging of aged venous thrombi with fibrin-specific monoclonal antibodies labeled with a radioactive moiety has been reported [Rosebrough, S. et al., Radiology 163: 575–577 (February, 1987)].

Radioimaging thrombi with radiolabeled monoclonal antibodies to platelets was first described by Peters, A., et al., [British Medical Journal, 293: 1525–1527 (December 1986)]. DTPA-coupled antibodies radiolabeled with metallic radionuclides has been described by Hnatowich, D., et al., [Journal of Immunological Methods, 65: 147–157 (1983)].

NMRI, ultrasound and X-ray imaging with metal chelates are described in U.S. Pat. No. 4,647,447. In addition, antibody coupling of metal chelates is mentioned at column 7, line 42. Monoclonal antibodies labeled with polymeric paramagnetic chelates and their use in NMRI methods have also been described [Shreve, P. et al., Magnetic Resonance in Medicine, Second Annual Meeting, Soc. of Magnetic Resonance in Medicine, Inc., San Francisco, p. 10 (1983), referenced by Koutcher, J., et al., J. Nucl. Med., 25: 506–513 (1984)].

U.S. Pat. No. 4,343,734 (Lian, et al.) describes gamma-carboxyglutamic acid (GLA) specific antibodies which can be labeled with fluorescein for immunofluorescence staining of tissue to determine the presence therein of GLA. GLA specific antibodies bind with GLA present in advanced atherosclerotic plaque having calcium deposits. Lian et al. report that GLA is not found in uncalcified plaques and that GLA is found in cardiac valves and aortas, and in circulating proteins such as prothombin, clotting factors VII, IX and X, Protein C and Protein S. However, the GLA binding antibodies developed by Lian et al. do not selectively bind to atherosclerotic plaque. The atherosclerotic plaque antibodies of the subject invention bind to all stages of atherosclerotic plaque including non-calcified stages, and do not selectively bind to GLA.

The concept of plaque enhancement by application of a stain has been reported [Spears, J. et al., J. Clin. Invest., 71: 395–399 (1983)]. These stains mark the plaque surfaces with a fluorescent compound. Plaque destruction by photoactivation of hematoporphyrin derivatives using an intraluminal laser-transmitting optical fiber has been suggested [Abela, G. et al., Am. J. Cardio., 50: 1199–1205 (1983)]. Moreover, tetracycline stains have also been suggested. [Murphy-Chutorian, D. et al., Am. J. Cardio., 55: 1293–1297 (1985)]. The above-identified stains were selected for their ability to bind the components of the atherosclerotic plaque. In principal, the stain absorbs laser light concentrating the light at the stained surface. Some staining of healthy tissue occurs causing stain associated damage to the surrounding tissue. Because laser light is monochromatic, chromophores having optimum absorption at the wavelength of the laser must be used to provide most controlled ablation.

In recent years, lasers have been used increasingly in microsurgery, both as scalpels and as coagulating instruments. Because of their ability to produce relatively bloodless incisions of great precision, as well as focal coagulation, they have been particularly useful in microsurgical procedures in the eye, central nervous system, nasal passages, cervix, gastrointestinal tract, skin, muscle, and even in small vessels.

Experiments with heart and arterial tissue from human cadavers have demonstrated the feasibility of vaporizing or etching away plaque on diseased surfaces. UV-wavelengths were found to offer more precision. Laser treatment of plaque in live animals was less precise, causing damage and perforation of surrounding healthy tissue. [Gerrity, R. et al., Jour. Thorac. Cardiovasc. Surg., 85: 409–421 (1983); Lee, G. et al., Am. Heart Jour., 105: 885–889 (1983); Lee, G. et al., Am. Heart Jour., pp 777–778 (Aug. 1984); Lee, G. et al., Am. Heart Jour., 108: 1577–1579 (1984); Lee, G. et al., Lasers in Surgery and Medicine, 4: 201–206 (1984); Abela, G. et al., Circulation, 71(2): 403–411 (1985); Prince, M. et al., Jour. Clin. Invest., 78: 295–302 (1986); and Srinivasan, R., Science, 234: 559–565 (1986)].

Recent reference has been made to monoclonal antibodies targeting differential antigens in atherosclerotic plaque. For example, oxidized or otherwise modified lipoproteins (Haberland, M. E., et al., Science, 241: 215 (1988). While concentrated within the plaque substance, these antigens have also been found in normal artery and/or other normal tissues. Some antigens and their corresponding monoclonal antibodies have shown early promise in the Watanabe rabbit model, but have not held up when applied to human lesions (Shih, I. L., et al, Proc. Nat'l. Acad. Sci., 87: 1436 (1990)), especially when diffuse markers of extracellular plaque tissue are being sought (Kimura J., et al., Virchows Arch., 410(2): 159 (1986)).

SUMMARY OF THE INVENTION

This invention provides an antigen comprising 5,7 cholestadien-3β-ol (7-dehydrocholesterol) or a compound having a structure similar to 5,7 cholestadien-3β-ol, and a quaternary ammonium salt.

This invention also provides methods for quantitatively determining in a sample the concentration of an antibody which specifically forms a complex with a plaque-indicative antigen, which methods comprise the use of the above-described antigen.

This invention also provides a method for coating a solid support with the above-described antigen.

This invention also provides a method of generating an antibody which is capable of specifically binding to atherosclerotic plaque, which method comprises administering the above-described antigen to an animal.

Further provided by this invention are an antibody produced by the above-described method, as well as a biologically active fragment of such an antibody.

This invention also provides reagents and pharmaceutical compositions comprising the above-described antibody or fragment.

This invention further provides methods for imaging atherosclerotic plaque which comprise the use of a reagent comprising the above-described antibody or fragment labeled with a detectable marker.

Also provided are methods for ablating atherosclerotic plaque which comprise the use of a reagent comprising the above-described antibody or fragment bound to a chromophore capable of absorbing radiation having a plaque ablating wavelength.

This invention further provides methods for detecting in a sample and for quantitatively determining in a sample an antigen indicative of the presence of atherosclerotic plaque, which methods comprise the use of the above-described antibody or fragment.

This invention further provides a method for reducing the amount of atherosclerotic plaque in a blood vessel, which method comprises the use of a reagent comprising the above-described antibody or fragment conjugated to an enzyme capable of digesting atherosclerotic plaque.

This invention also provides a method for treating atherosclerosis in a subject, which method comprises administering to the subject a reagent comprising the above-described antibody or fragment thereof bound to a drug useful in treating atherosclerosis.

This invention also provides a rat myeloma cell line designated Z2D3 73/30 1D10, having ATCC Accession Number CRL 11203.

Also provided by this invention is a murine-human chimeric monoclonal antibody produced by the above-described rat myeloma cell line, as well as a biologically active fragment thereof.

This invention also provides reagents and pharmaceutical compositions comprising the above-described chimeric monoclonal antibody or fragment.

This invention further provides methods for imaging atherosclerotic plaque which comprise the use of a reagent comprising the above-described chimeric monoclonal antibody or fragment thereof labeled with a detectable marker.

Also provided are methods for ablating atherosclerotic plaque which comprise the use of a reagent comprising the above-described chimeric monoclonal antibody or fragment thereof bound to a chromophore capable of absorbing radiation having a plaque ablating wavelength.

This invention further provides methods for detecting in a sample and for quantitatively determining in a sample an antigen indicative of the presence of atherosclerotic plaque, which methods comprise the use of the above-described chimeric monoclonal antibody or fragment thereof.

This invention further provides a method for reducing the amount of atherosclerotic plaque in a blood vessel, which method comprises the use of a reagent comprising the above-described chimeric monoclonal antibody or fragment thereof conjugated to an enzyme capable of digesting atherosclerotic plaque.

This invention also provides a method for treating atherosclerosis in a subject, which method comprises administering to the subject a reagent comprising the above-described chimeric monoclonal antibody or fragment thereof bound to a drug useful in treating atherosclerosis.

This invention also provides a CDR-grafted antibody comprising a CDR region amino acid sequence from hybridoma Z2D3 or hybridoma Z2D3/3E5 and framework and constant region amino acid sequences from a human immunoglobulin, as well as a biologically active fragment of such a CDR-grafted antibody.

This invention also provides reagents and pharmaceutical compositions comprising the above-described CDR-grafted antibody or fragment.

This invention further provides methods for imaging atherosclerotic plaque which comprise the use of a reagent comprising the above-described CDR-grafted antibody or fragment labeled with a detectable marker.

Also provided are methods for ablating atherosclerotic plaque which comprise the use of a reagent comprising the above-described CDR-grafted antibody or fragment bound to a chromophore capable of absorbing radiation having a plaque ablating wavelength.

This invention further provides methods for detecting in a sample and for quantitatively determining in a sample an antigen indicative of the presence of atherosclerotic plaque, which methods comprise the use of the above-described CDR-grafted antibody or fragment.

This invention further provides a method for reducing the amount of atherosclerotic plaque in a blood vessel, which method comprises the use of a reagent comprising the above-described CDR-grafted antibody or fragment conjugated to an enzyme capable of digesting atherosclerotic plaque.

This invention also provides a method for treating atherosclerosis in a subject, which method comprises administering to the subject a reagent comprising the above-described CDR-grafted antibody or fragment bound to a drug useful in treating atherosclerosis.

This invention also provides a peptide having an amino acid sequence which is the same or substantially the same as the amino acid sequence of the variable region of the heavy chain of the above-described chimeric monoclonal antibody.

This invention also provides a peptide having an amino acid sequence which is the same or substantially the same as the amino acid sequence of the variable region of the light chain of the above-described amino acid sequence.

This invention also provides a peptide which comprises an amino acid sequence or combination of amino acid sequences, each of which amino acid sequences is the same or substantially the same as the amino acid sequence of a complimentarity determining region (CDR) of the above-described chimeric monoclonal antibody.

Finally, this invention provides isolated nucleic acid molecules having nucleotide sequences encoding for the above-described peptides.

Figure 1A:
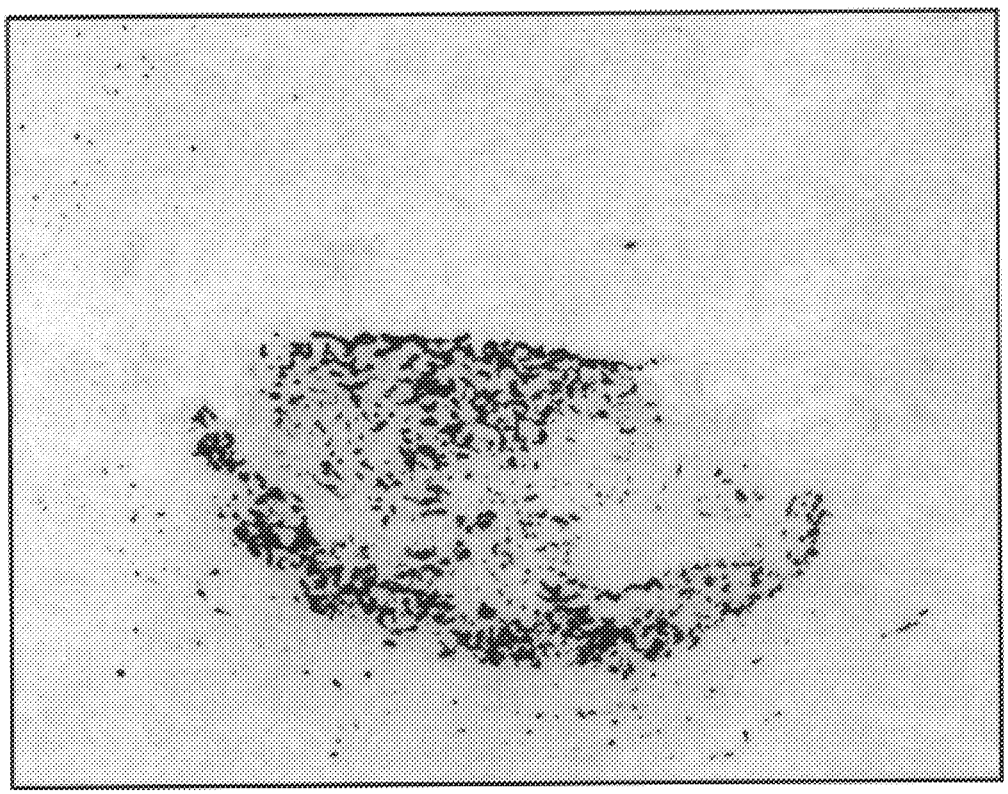
FIG. 1A.

Immunohistological staining with the Z2D3 IgM monoclonal antibody of a moderate atherosclerotic lesion; staining of a frozen human coronary artery section with the mouse Z2D3 IgM monoclonal antibody.

FIG. 1B.

Immunohistological staining with the Z2D3 IgM monoclonal antibody of a moderate atherosclerotic lesion; staining of a sequential section with a non specific mouse IgM monoclonal antibody.

FIG. 2A.

Immunohistological staining with the Z2D3 IgM monoclonal antibody of an advanced atherosclerotic lesion; staining of a frozen human coronary artery section with the mouse Z2D3 IgM monoclonal antibody.

FIG. 2B.

Immunohistological staining with the Z2D3 IgM monoclonal antibody of an advanced atherosclerotic lesion; staining of a sequential section with a non specific mouse IgM monoclonal antibody.

FIG. 3A.

Chemical structure of 5-Cholesten-3β-ol, Cholesterol.

FIG. 3B.

ELISA activity of 5-cholesten-3β-ol in combination with

X: Benzyldimethylhexadecylammonium chloride;

○: palmitoylcholine.

FIG. 4A.

Chemical structure of 5,7-Cholestadien-3β-ol, 7-Dehydrocholesterol.

FIG. 4B.

ELISA activity of 5,7-Cholestadien-3β-ol in combination with

X: Benzyldimethylhexadecylammonium chloride;

○: palmitoylcholine.

FIG. 5A.

Chemical structure of 5,24-Cholestadien-3β-ol, Desmosterol.

FIG. 5B.

ELISA activity of 5,24-Cholestadien-3β-ol in combination with

X: Benzyldimethylhexadecylammonium chloride;

○: palmitoylcholine.

FIG. 6A.

A: Chemical structure of 5α-Cholest-7-en-3β-ol, Lathosterol.

FIG. 6B.

ELISA activity of 5α-Cholest-7-en-3β-ol in combination with,

X: Benzyldimethylhexadecylammonium chloride;

○: palmitoylcholine.

FIG. 7A.

Chemical structure of 5α-Cholestane-3β-ol, Dihydrocholesterol.

FIG. 7B.

ELISA activity of 5α-Cholestane-3β-ol in combination with,

X: Benzyldimethylhexadecylammonium chloride;

○: palmitoylcholine.

FIG. 8A.

Chemical structure of 5-Cholesten-3-one.

FIG. 8B.

ELISA activity of 5-Cholest-3-one in combination with,

X: Benzyldimethylhexadecylammonium chloride;

○: palmitoylcholine.

FIG. 9A.

Chemical structure of 5-Androsten-3β-ol.

FIG. 9B.

ELISA activity of 5-Androsten-3β-ol in combination with,

X: Benzyldimethylhexadecylammonium chloride;

○: palmitoylcholine.

FIG. 10A.

Chemical structure of 5-Cholesten-3β-ol acetate, Cholesteryl Acetate.

FIG. 10B.

ELISA activity of 5-Cholesten-3β-ol acetate in combination with,

X: Benzyldimethylhexadecylammonium chloride;

○: palmitoylcholine.

FIG. 11A.

Chemical structure of 5-Cholesten.

FIG. 11B.

ELISA activity of 5-Cholesten in combination with,

X: Benzyldimethylhexadecylammonium chloride;

○: palmitoylcholine.

FIG. 12A.

Chemical structure of Cholecalciferol, Vitamin D3.

FIG. 12B.

ELISA activity of Cholecalciferol in combination with,

X: Benzyldimethylhexadecylammonium chloride;

○: palmitoylcholine.

FIG. 13.

Biosynthesis and metabolism of cholesterol. Outline of a portion of the biological pathway of steroid metabolism showing the six most active steroid compounds in the surrogate antigen ELISA assay and their relationship to cholesterol. The enzymes which catalyze individual steps are in italics.

FIG. 14.

ELISA activity of various choline esters in presence of 5-Cholesten-3β-ol, Cholesterol.

○=Lauroylcholine;

■=Myristoylcholine;

Δ=Palmitoylcholine; and

X=Stearoylcholine.

FIG. 15.

ELISA activity of various choline esters in presence of 5,7-Cholestadien-3β-ol, 7-Dehydrocholesterol.

○=Lauroylcholine;

■=Myristoylcholine;

Δ=Palmitoylcholine; and

X=Stearoylcholine.

FIG. 16.

Agarose gel analysis of amplified Z2D3 VH and VK DNA. Lane 1, φx 174 Hae III fragments;

lane 2, VH undigested;

lane 3, VH Pst I digest;

lane 4, VH Hind III digest;

lane 5, VK undigested;

lane 6, VK Hind III digest;

lane 7, VK Pvu II digest.

FIGS. 17A–17F.

Sequence determination from M13 clones containing Z2D3 VH DNA. Gaps or dashes are used to maximize sequence homology. In the consensus sequence, underlining represents homology. In the consensus sequence, the following positions are underlined: 9-14; 16-19; 21-49; 51-77; 79-150; 152-219; 221-353; 357-375; 378-388.

Sequence VH1BACK (1,22) is SEQ ID NO:1.

Sequence Z2VH1 (1, 220)' is SEQ ID NO:2.

Sequence Z2VH12 (1,218)' is SEQ ID NO:3.

Sequence Z2VH7 (1,220)' is SEQ ID NO:4.

Sequence Z2VH9 (1, 218)' is SEQ ID NO:5.

Sequence Z2VH20A (1, 237) is SEQ ID NO:6.

Sequence Z2VH2 (1, 220) is SEQ ID NO:7.

Sequence Z2VH5 (1, 220) is SEQ ID NO:8.

Sequence Z2VH6 (1, 220) is SEQ ID NO:9.

Sequence Z2VH8 (1, 219) is SEQ ID NO:10.

Sequence Z2VH10 (1, 218) is SEQ ID NO:11.

Sequence Z2VH21 (1, 147) is SEQ ID NO:12.

Sequence Z2VH17 (1, 114)' IS SEQ ID NO:13.

Sequence CM1FOR (1, 34)' is SEQ ID NO:14.

Sequence consensus is SEQ ID NO:15.

FIGS. 18A–18G.

Z2D3 VH DNA and amino acid sequences. CDRs are boxed and oligonucleotides used in the PCR are underlined. Restriction endonuclease cleavage sites are identified by alpha-numeric code. CH1 identifies the beginning of the constant region of the antibody.

The first sequence, which begins "AGGTSMARCT-G . . . ", is SEQ ID NO:16.

The second sequence, which begins "TCCASKTYGA-C . . . ", is SEQ ID NO:17.

The third sequence, which begins "v, k/q, l, q, e, s, g, g, g, l, v, . . . ", is represented by SEQ ID NO:18 and SEQ ID NO:19; wherein SEQ ID NO:18 corresponds to "v, k, l, q, e, s, g, g, g, l, v, . . . "; and wherein SEQ ID NO:19 corresponds to "v, q, l, q, e, s, g, g, g, l, v, . . . ".

SEQ ID NO:20 corresponds to the first sequence within the first box.

SEQ ID NO:21 corresponds to the second sequence within the first box.

SEQ ID NO:22 corresponds to the third sequence within the first box.

SEQ ID NO:23 corresponds to the first sequence within the second box.

SEQ ID NO:24 corresponds to the second sequence within the second box.

SEQ ID NO:25 corresponds to the third sequence within the second box.

SEQ ID NO:26 corresponds to the first sequence within the third box.

SEQ ID NO:27 corresponds to the second sequence within the third box.

SEQ ID NO:28 corresponds to the third sequence within the third box.

FIG. 19.

Comparison of the amino acid sequences of Z2D3 VH (top) and a consensus sequence from mouse subgroup IIIB (bottom). Invariant residues in mouse subgroup IIIB are highlighted (▲). The center sequence indicates those residues which are homologous. Nearly all of the invariant mouse subgroup IIIB residues are homologous with the Z2D3 VH sequence. Gaps or dashes are used to maximize sequence homology. CDRs are boxed. Sequence Z2D3MUVH is SEQ ID NO:29.

Sequence MUVHIIIB is SEQ ID NO:30.

SEQ ID NO:31 corresponds to Sequence Z2D3MUVH within the first box.

SEQ ID NO:32 corresponds to Sequence MUVHIIIB within the first box.

SEQ ID NO:33 corresponds to Sequence Z2D3MUVH within the second box.

SEQ ID NO:34 corresponds to Sequence MUVHIIIB within the second box.

SEQ ID NO:35 corresponds to Sequence Z2D3MUVH within the third box.

SEQ ID NO:36 corresponds to Sequence MUVHIIIB within the third box.

FIGS. 20A–20H.

Sequence determination from M13 clones containing Z2D3 VK DNA. Gaps or dashes are used to maximize sequence homology. In the consensus sequence, underlining represents homology. In the consensus sequence, the following positions are underlined: 10-27; 29-349; 351-360.

Sequence VK1BACK (1, 24) is SEQ ID NO:37.

Sequence Z2VK34 (1, 291)' is SEQ ID NO:38.

Sequence Z2VK10 (1, 140)' is SEQ ID NO:39.

Sequence Z2VK17 (1, 92)' is SEQ ID NO:40.

Sequence Z2VK23 (1, 152) is SEQ ID NO:41.

Sequence Z2VK3 (1, 141) is SEQ ID NO:42.

Sequence Z2VK11A (1, 84) is SEQ ID NO:43.

Sequence Z2VK7 (1, 140) is SEQ ID NO:44.

Sequence Z2VK8A (1, 140) is SEQ ID NO:45.

Sequence Z2VK28 (1, 265) is SEQ ID NO:46.

Sequence Z2VK29 (1, 265) is SEQ ID NO:47.
Sequence Z2VK30 (1, 265) is SEQ ID NO:48.
Sequence Z2VK31 (1, 264) is SEQ ID NO:49.
Sequence Z2VK32 (1, 264) is SEQ ID NO:50.
Sequence Z2VK36 (1, 263)' is SEQ ID NO:51.
Sequence Z2VK25 (1, 260)' is SEQ ID NO:52.
Sequence Z2VK18B (1, 88)' is SEQ ID NO:53.
Sequence Z2VK19 (1, 203) is SEQ ID NO:54.
Sequence Z2VK20 (1, 204) is SEQ ID NO:55.
Sequence Z2VK16 (1, 175)' is SEQ ID NO:56.
Sequence Z2VK18A (1, 167)' is SEQ ID NO:57.
Sequence Z2VK8B (1, 154)' is SEQ ID NO:58.
Sequence CK2FOR (1, 32)' is SEQ ID NO:59.
Sequence consensus is SEQ ID NO:60.

FIGS. 21A–21H.

Z2D3 VK DNA and amino acid sequences. CDRs are boxed and oligonucleotides used in the PCR are underlined. Restriction endonuclease cleavage sites are identified by alpha-numeric code. Gaps or dashes are used to maximize sequence homology. CK identifies the beginning of the constant region of the kappa light chain of the antibody.

The first sequence, which begins "CTGCAGSAGT-C . . . ", is SEQ ID NO:61.

The second sequence, which begins "GACGTCSTCA-G . . . ", is SEQ ID NO:62.

The third sequence, which begins "m, r, a, p, a, q, f, f, g, i, l, . . . ", is SEQ ID NO:63.

SEQ ID NO:64 corresponds to the first sequence within the first box.

SEQ ID NO:65 corresponds to the second sequence within the first box.

SEQ ID NO:66 corresponds to the third sequence within the first box.

SEQ ID NO:67 corresponds to the first sequence within the second box.

SEQ ID NO:68 corresponds to the second sequence within the second box.

SEQ ID NO:69 corresponds to the third sequence within the second box.

SEQ ID NO:70 corresponds to the first sequence within the third box.

SEQ ID NO:71 corresponds to the second sequence within the third box.

SEQ ID NO:72 corresponds to the third sequence within the third box.

FIG. 22.

Comparison of the amino acid sequence of Z2D3 VK and a consensus sequence from mouse family V. Invariant residues in the mouse family V sequence are highlighted (▲). The center sequence indicates those residues which are homologous. All of the invariant mouse family V residues are homologous with the Z2D3 VK sequence. Gaps or dashes are used to maximize sequence homology. CDRs are boxed.

Sequence Z2D3MUVK is SEQ ID NO:73.
Sequence MUVKV is SEQ ID NO:74.
SEQ ID NO:75 corresponds to Sequence Z2D3MUVK within the first box.
SEQ ID NO:76 corresponds to Sequence MUVKV within the first box.
SEQ ID NO:77 corresponds to Sequence Z2D3MUVK within the second box.
SEQ ID NO:78 corresponds to Sequence MUVKV within the second box.
SEQ ID NO:79 corresponds to Sequence Z2D3MUVK within the third box.
SEQ ID NO:80 corresponds to Sequence MUVKV within the third box.

FIG. 23.

Components and organization of the immunoglobulin heavy chain mammalian expression vector.

FIG. 24.

Components and organization of the immunoglobulin kappa chain mammalian expression vector.

FIG. 25.

ELISA showing binding of murine Z2D3 antibody and murine V/human IgG1, K chimeric antibody to atherosclerotic plaque antigen.

FIG. 26A.

Immunohistological staining of Z2D3 chimeric antibody with early atherosclerotic lesion; chimeric Z2D3 F(ab')$_2$; immunostaining of an unfixed 5μ thick frozen tissue section of human coronary artery from a patient with early atherosclerosis, using biotinylated chimeric Z2D3 F(ab')$_2$ anti-human atherosclerotic plaque antibody. The tissue sections are stained using ABC immunoperoxidase method, and counterstained with hematoxylin.

FIG. 26B.

Immunohistological staining of Z2D3 chimeric antibody with early atherosclerotic lesion; non-specific human F(ab')$_2$; immunostaining of an unfixed 5μ thick frozen tissue section of human coronary artery from a patient with early atherosclerosis, using biotinylated non-specific human IgG F(ab')$_2$. The tissue sections are stained using ABC immunoperoxidase method, and counterstained with hematoxylin.

FIG. 27A.

Immunohistological staining of Z2D3 chimeric antibody with moderate atherosclerotic lesion; chimeric Z2D3 F(ab')$_2$; immunostaining of an unfixed 5μ thick frozen tissue section of human coronary artery from a patient with moderate atherosclerosis, using biotinylated chimeric Z2D3 F(ab')$_2$ anti-human atherosclerotic plaque antibody. The tissue sections are stained using ABC immunoperoxidase method, and counterstained with hematoxylin.

FIG. 27B.

Immunohistological staining of Z2D3 chimeric antibody with moderate atherosclerotic lesion; non-specific human F(ab')$_2$; immunostaining of an unfixed 5 μ thick frozen tissue section of human coronary artery from a patient with moderate atherosclerosis, using biotinylated non-specific human IgG F(ab')$_2$. The tissue sections are stained using ABC immunoperoxidase method, and counterstained with hematoxylin.

FIG. 28A.

Immunohistological staining of Z2D3 chimeric antibody with advanced atherosclerotic lesion; chimeric Z2D3 F(ab')$_2$; immunostaining of an unfixed 5 μ thick frozen tissue section of human coronary artery from a patient with advanced atherosclerosis, using biotinylated chimeric Z2D3 F(ab')$_2$ anti-human atherosclerotic plaque antibody. The tissue sections are stained using ABC immunoperoxidase method, and counterstained with hematoxylin.

FIG. 28B.

Immunohistological staining of Z2D3 chimeric antibody with advanced atherosclerotic lesion; non-specific human F(ab')$_2$; immunostaining of an unfixed 5 μ thick frozen tissue section of human coronary artery from a patient with advanced atherosclerosis, using biotinylated non-specific human IgG F(ab')$_2$. The tissue sections are stained using ABC immunoperoxidase method, and counterstained with hematoxylin.

DETAILED DESCRIPTION OF THE INVENTION

The subject invention provides an antigen indicative of the presence of atherosclerotic plaque which antigen comprises 5,7 cholestadien-3β-ol (7-dehydrocholesterol) or a compound having a structure similar to 5,7 cholestadien-3β-ol, and a quaternary ammonium salt.

The steroid compound may be 5,7-cholestadien-3β-ol (7-dehydrocholesterol); 5-cholesten-3β-ol (cholesterol); 5,24-cholestadien-3β-ol (desmosterol); 5α-cholest-7-en-3β-ol (lathosterol); 5α-cholestane-3β-ol (cholestanol or dihydrocholesterol), or 5-cholesten-3-one.

In one embodiment, the quaternary ammonium salt is a fatty acid ester of choline. In an embodiment wherein the quaternary ammonium salt is a fatty acid ester of choline, the fatty acid ester of choline may comprise a chain of about 12 or more atoms in length. Examples of fatty acid esters of choline useful in the practice of this invention include: dodecanoic acid choline ester (lauroylcholine); tridecanoic acid choline ester; tetradecanoic acid choline ester (myristoylcholine); pentadecanoic acid choline ester; hexadecanoic acid choline ester (palmitoylcholine); heptadecanoic acid choline ester; octadecanoic acid choline ester (stearoylcholine); nonadecanoic acid choline ester; eicosanoic acid choline ester (arachidylcholine); henicosanoic acid choline ester; docosanoic acid choline ester; tricosanoic acid choline ester; tetracosanoic acid choline ester; or pentacosanoic acid choline ester.

In another embodiment, the quaternary ammonium salt may have a substituent chain comprising about 12 or more atoms in length.

In a further embodiment the quaternary ammonium salt may be a cationic detergent. Examples of cationic detergents useful in the practice of this invention include:
benzyldimethyldodecylammonium salt;
benzyldimethyltridecylammonium salt;
benzyldimethyltetradecylammonium salt;
benzyldimethylpentadecylammonium salt;
benzyldimethylhexadecylammonium salt;
benzyldimethylheptadecylammonium salt;
benzyldimethyloctadecylammonium salt;
benzyldimethylnonadecylammonium salt;
benzyldimethyleicosylammonium salt;
benzyldimethylhenicosylammonium salt;
benzyldimethyldocosylammonium salt;
benzyldimethyltricosylammonium salt;
benzyldimethyltetracosylammonium salt;
benzyldimethylpentacosylammonium salt;
trimethyltetradecylammonium salt;
trimethylpentadecylammonium salt;
trimethylhexadecylammonium salt;
trimethylhepadecylammonium salt;
trimethyloctadecylammonium salt;
trimethylnonadecylammonium salt;
trimethyleicosylammonium salt;
trimethylhenicosylammonium salt;
trimethyldocosylammonium salt;
trimethyltricosylammonium salt;
trimethyltetracosylammonium salt;
trimethylpentacosylammonium salt;
didodecyldimethylammonium salt;
N-dodecylpyridinium salt;
N-tridecylpyridinium salt;
N-tetradecylpyridinium salt;
N-pentadecylpyridinium salt;
N-hexadecylpyridinium salt;
N-heptadecylpyridinium salt;
N-octadecylpyridinium salt;
N-nonadecylpyridinium salt;
N-eicosylpyridinium salt;
N-henicosylpyridinium salt;
N-docosylpyridinium salt;
N-tricosylpyridinium salt;
N-tetracosylpyridinium salt;
N-pentacosylpyridinium salt;
dodecyldimethylethylammonium salt;
tridecyldimethylethlyammonium salt;
tetradecyldimethylethylammonium salt;
pentadecyldimethylethylammonium salt;
hexadecyldimethylethylammonium salt;
heptadecyldimethylethylammonium salt;
octadecyldimethylethylammonium salt;
nonadecyldimethylethylammonium salt;
eicosyldimethylethylammonium salt;
henicosyldimethylethylammonium salt;
docosyldimethylethylammonium salt;
tricosyldimethylethylammonium salt;
tetracosyldimethylethylammonium salt;
pentacosyldimethylethylammonium salt; or
benzalkonium salt.

In one embodiment, the above-described antigen specifically binds to a monoclonal antibody produced by hybridoma Z2D3 (ATCC Accession Number HB9840), Z2D3/3E5 (ATCC Accession Number HB10485), or Z2D3 73/30 1D10 (ATCC Accession Number CRL 11203).

In another embodiment of this invention the above-described antigen may be labeled with a detectable marker. The choice of marker used will vary depending upon the application. However, the choice of marker is readily apparent to one skilled in the art.

In the practice of this invention the detectable marker may be an enzyme such as horseradish peroxidase or alkaline phosphatase, a paramagnetic ion, a chelate of a paramagnetic ion, biotin, a fluorophore, a chromophore, a heavy metal, a chelate of a heavy metal, a compound or element which is opaque to X-rays, a radioisotope, or a chelate of a radioisotope.

Radioisotopes useful as detectable markers include such isotopes as iodine-123, iodine-125, iodine-128, iodine-131, or a chelated metal ion of chromium-51, cobalt-57, gallium-67, indium-111, indium-113m, mercury-197, selenium-75, thallium-201, technetium-99m, lead-203, strontium-85, strontium-87, gallium-68, samarium-153, europium-157, ytterbium-169, zinc-62, or rhenium-188.

Paramagnetic ions useful as detectable markers include such ions as chromium (III), manganese (II), iron (III), iron (II), cobalt (II), nickel (II), copper (II), praseodymium (III), neodymium (III), samarium (III), gadolinium (III), terbium (III), dysprosium (III), holmium (III), erbium (III), or ytterbium (III).

In one embodiment the detectable marker may be iodine, an iodine complex, or a chelate of iodine.

The present invention also provides a method for quantitatively determining in a sample the concentration of an antibody which specifically forms a complex with a plaque-indicative antigen, which comprises:

(a) contacting a solid support with an excess of the above described antigen under conditions permitting the antigen to attach to the surface of the solid support;

(b) removing unbound antigen;

(c) contacting the resulting solid support to which the antigen is bound with the sample under conditions such that any antibody present in the sample binds to the bound antigen and forms a complex therewith;

(d) removing any antibody which is not bound to the complex;

(e) contacting any complex so formed with an excess of a detectable reagent which specifically binds to any antibody present in the complex so as to form a second complex which includes the antigen, the antibody, and the detectable reagent;

(f) removing any detectable reagent which is not bound in the second complex;

(g) quantitatively determining the amount of detectable reagent present in the second complex; and (h) thereby quantitatively determining in the sample the concentration of an antibody which specifically forms a complex with a plaque-indicative antigen.

In one embodiment of the method the detectable reagent comprises an antibody labeled with a detectable marker, wherein the antibody labeled with the detectable marker specifically binds to the complexed antibody in step (e).

The subject invention also provides a method for quantitatively determining in a sample the concentration of an antibody which specifically forms a complex with an plaque-indicative antigen indicative of the presence of atherosclerotic plaque, which comprises:

(a) contacting a solid support with a predetermined amount of the above described antigen under conditions permitting the antigen to attach to the surface of the support;

(b) removing unbound antigen;

(c) contacting the resulting solid support to which the antigen is bound with a predetermined amount of antibody labeled with a detectable marker and with the sample under conditions such that the labeled and sample antibodies competitively bind to the antigen bound to the solid support and form a complex therewith;

(d) removing any labeled or sample antibody which is not bound to the complex;

(e) quantitatively determining the amount of labeled antibody bound to the solid support; and (f) thereby quantitatively determining in the sample the concentration of an antibody which specifically forms a complex with a plaque-indicative antigen.

In the practice of the method step (e) may alternatively comprise quantitatively determining the amount of labeled antibody not bound to the solid support.

The subject invention also provides a method for quantitatively determining in a sample the concentration of antibody which specifically forms a complex with a plaque-indicative antigen, which comprises:

(a) contacting a solid support with a predetermined amount of the above described antigen under conditions permitting the antigen to attach to the surface of the support;

(b) removing any antigen which is not bound to the support;

(c) contacting the solid support to which the antigen is bound with the sample under conditions such that any antibody present in the sample binds to the bound antigen and forms a complex therewith;

(d) removing any antibody which is not bound to the complex;

(e) contacting the complex so formed with a predetermined amount of antibody labeled with a detectable marker under conditions such that the labeled antibody competes with the antibody in the sample for binding to the antigen;

(f) removing any labeled and sample antibody which are not bound to the complex;

(g) quantitatively determining the amount of labeled antibody bound to the solid support; and (h) thereby quantitatively determining in the sample the concentration of antibody which specifically forms a complex with a plaque-indicative antigen.

In the practice of the method step (g) may alternatively comprise quantitatively determining the amount of labeled antibody not bound to the solid support.

The subject invention, also provides the above described antigen bound to a solid support. In the practice of the subject invention the solid support may be an inert polymer, a microwell, or a porous membrane. In one embodiment the inert polymer is a polystyrene bead. The polystyrene bead may have a diameter from about 0.1 $\mu$m to about 100 $\mu$m.

The subject invention also provides method for coating a solid support with the above described antigen which comprises:

(a) forming a mixture by dissolving in an organic solvent the 5,7 cholestadien-3$\beta$-ol or compound having the structure similar to 5,7 cholestadien-3$\beta$-ol and the quaternary ammonium salt in a suitable molar ratio and in sufficient concentrations so as to coat the surface of the solid support after evaporation of the solvent, wherein the organic solvent does not react with the 5,7 cholestadien-3$\beta$-ol or the compound having the structure similar to 5,7 cholestadien-3$\beta$-ol, the quaternary ammonium salt, or the solid support;

(b) contacting the mixture of step (a) with the surface of the solid support;

(c) evaporating the organic solvent of the mixture in step (b); and (d) thereby coating onto the surface of the solid support the surrogate antigen.

Examples of organic solvents useful in the practice of this method include ethanol, acetone, chloroform, ether, or benzene.

In the practice of this method the molar ratio of the 5,7 cholestadien-3$\beta$-ol or compound having the structure similar to 5,7 cholestadien-3$\beta$-ol to the quaternary ammonium salt ranges from about 0.1:1 to about 200:1. In a preferred embodiment the molar ratio of 5,7 cholestadien-3$\beta$-ol or compound having the structure similar to 5,7 cholestadien-3$\beta$-ol to the quaternary ammonium salt ranges from about 2:1 to about 64:1.

The subject invention also provides a method of generating an antibody which is capable of specifically binding to atherosclerotic plaque, which method comprises:

(a) administering to an animal at least one time an amount of the above described antigen sufficient to generate the antibody;

(b) obtaining a serum from the animal;

(c) testing the serum for antibody capable of specifically binding to atherosclerotic plaque;

(d) wherein if the test in step (c) is positive, thereby generating the antibody capable of specifically binding to atherosclerotic plaque.

In a preferred embodiment of the above-described method step (a) comprises administering antigen coated onto the surface of a solid support. Solid supports useful in the above described method have been described above.

In one embodiment of the method the antigen comprises 5,7-cholestadien-3$\beta$-ol and the quaternary ammonium salt is benzyldimethylhexadecylammonium chloride or palmitoylcholine.

In another embodiment of the method the antigen comprises 5-cholesten-3$\beta$-ol and the quaternary ammonium salt is benzyldimethylhexadecylammonium chloride or palmitoylcholine.

In a further embodiment of the method the antigen comprises 5-cholesten-3-one and the quaternary ammonium salt is benzyldimethylhexadecylammonium chloride or palmitoylcholine.

In one embodiment of this method the solid support is a porous membrane, administered by implantation.

In the practice of this method the animal is a vertebrate such as a bird, or further is a mammal such as a rodent.

The subject invention also provides an antibody generated by the above-described method.

In one embodiment, the above-described antibody is capable of specifically binding to an antigen recognized by a monoclonal antibody produced by hybridoma Z2D3, Z2D3/3E5, or Z2D3 73/30 1D10.

This invention further provides a method of generating a monoclonal antibody which is capable of specifically binding to atherosclerotic plaque, which method comprises:

(a) administering to an animal at least one time an amount of the above antigen sufficient to generate the antibody;

(b) obtaining a serum from the animal;

(c) testing the serum for antibody capable of specifically binding to atherosclerotic plaque;

(d) obtaining an antibody producing cell from the animal with serum which tested positively in step (c);

(e) fusing the antibody producing cell with a myeloma cell or a myeloma derivative to generate a hybridoma cell which produces an antibody capable of specifically binding to atherosclerotic plaque;

(f) isolating hybridoma cells which secrete the antibody which is capable of specifically binding to atherosclerotic plaque;

(g) thereby generating a monoclonal antibody capable of specifically binding to atherosclerotic plaque.

In a preferred embodiment of the above-described method of generating a monoclonal antibody step (a) comprises administering antigen coated onto the surface of a solid support. Solid supports useful in the above described method have been described above.

In one embodiment of the method the antigen comprises 5,7-cholestadien-3β-ol and the quaternary ammonium salt is benzyldimethylhexadecylammonium chloride or palmitoylcholine.

In another embodiment of the method the antigen comprises 5-cholesten-3β-ol and the quaternary ammonium salt is benzyldimethylhexadecylammonium chloride or palmitoylcholine.

In a further embodiment of the method the antigen comprises 5-cholesten-3-one and the quaternary ammonium salt is benzyldimethylhexadecylammonium chloride or palmitoylcholine.

In one embodiment of this method the solid support is a porous membrane, administered by implantation.

In the practice of this method the animal is a vertebrate such as a bird, or further is a mammal such as a rodent.

This invention also provides a monoclonal antibody generated by the above-described method.

In one embodiment, the above-described antibody is capable of specifically binding to an antigen recognized by a monoclonal antibody produced by hybridoma Z2D3, Z2D3/3E5, or Z2D3 73/30 1D10.

The subject invention also provides biologically active fragments of the above described monoclonal antibody. In separate embodiments the fragment may comprise the F(ab')$_2$, Fab', Fab, $F_V$, $V_H$, or $V_L$ antibody fragment. In further embodiments the fragments are capable of specifically binding to an antigen recognized by a monoclonal antibody produced by hybridoma Z2D3, Z2D3/3E5, or Z2D3 73/30 1D10.

The subject invention also provides the above described monoclonal antibody or fragment thereof labeled with a detectable marker. The choice of marker used will vary depending upon the application. However, the choice of marker is readily apparent to one skilled in the art. Examples of detectable markers useful in the practice of this invention have been described above.

The subject invention also provides the above described monoclonal antibody or fragment thereof bound to a solid support. Examples of solid supports useful in the practice of this invention have been described above.

The subject invention also provides a reagent for use in imaging atherosclerotic plaque, which comprises the above described monoclonal antibody or fragment thereof labeled with a detectable marker in an amount effective to image atherosclerotic plaque, and a physiologically acceptable carrier.

The subject invention further provides a method for imaging atherosclerotic plaque, which comprises:

(a) contacting the atherosclerotic plaque to be imaged with the above described reagent under conditions such that the reagent binds to the atherosclerotic plaque; and (b) detecting the detectable marker labelling the antibody or fragment in the reagent bound to the atherosclerotic plaque;

thereby imaging the atherosclerotic plaque.

In one embodiment the above described method can be used to image atherosclerotic plaque located in blood vessel walls of a subject.

The subject invention also provides a method for differentially imaging atherosclerotic plaque and normal tissue in a lumen, which comprises:

(a) contacting the lumen with an antibody which specifically binds to normal intima or media and which does not bind to atherosclerotic plaque, and which is labeled with a detectable marker;

(b) contacting the lumen with the above described reagent under conditions such that the reagent binds to the atherosclerotic plaque;

(c) detecting the detectable marker labeling the antibody of step (a) bound to the normal intima or media; and (d) detecting the detectable marker labeling the antibody or the fragment in the reagent of step (b) bound to the atherosclerotic plaque;

wherein the detectable marker labeling the antibody which specifically binds to normal intima or media is different from the detectable marker labeling the antibody or fragment in the reagent, thereby differentially imaging the atherosclerotic plaque and the normal tissue in the lumen.

In a preferred embodiment of the above described method the antibody which specifically binds to normal intima or media is a purified antibody which specifically binds to an antigen synthesized by or present in normal smooth muscle cells and normal connective tissue surrounding arteries. In a more preferred embodiment, the antibody is a monoclonal antibody produced by hybridoma Q10E7 having ATCC Accession Number 10188.

The subject invention also provides the above described monoclonal antibody or fragment thereof bound to a chromophore capable of absorbing radiation having a plaque ablating wavelength. In the practice of this invention the chromophore absorbs light having a wavelength from about 190 nm to about 1100 nm. Examples of chromophores useful in the practice of this invention include fluorescein, rhodamine, tetracycline, hematoporphyrin, or β-carotene.

The subject invention provides a reagent for ablating atherosclerotic plaque comprising the above described monoclonal antibody or fragment thereof bound to a chromophore capable of absorbing radiation having a plaque ablating wavelength in an amount effective to highlight the atherosclerotic plaque to be ablated and a physiologically acceptable carrier.

The subject invention further provides a method for ablating atherosclerotic plaque, which comprises:
 (a) contacting atherosclerotic plaque with an effective amount of the above described reagent so that the antibody or fragment thereof present in the reagent binds to the atherosclerotic plaque forming an atherosclerotic antibody complex;
 (b) exposing the resulting complex to radiation having a plaque ablating wavelength under conditions such that the radiation is absorbed by the chromophore at a sufficient energy to ablate the atherosclerotic plaque; and
 (c) thereby ablating the atherosclerotic plaque.

In the practice of this invention the atherosclerotic plaque to be ablated may be located in a blood vessel. In such an instance the above described method for ablating atherosclerotic plaque comprises:
 (a) contacting the normal lumen with an antibody which specifically binds to normal intima or media and has bound thereto a moiety capable of reflecting radiation of the plaque ablating wavelength;
 (b) contacting the atherosclerotic plaque with the above described reagent;
 (c) exposing the atherosclerotic plaque to the radiation having plaque ablating wavelength; and
 (d) thereby ablating the atherosclerotic plaque present in a blood vessel.

In a preferred embodiment the above described method, the antibody which specifically binds to normal intima or media is a purified antibody which specifically binds to an antigen synthesized by or present in normal smooth muscle cells and normal connective tissue surrounding arteries. In a more preferred embodiment the antibody is a monoclonal antibody produced by hybridoma Q10E7 having ATCC Accession Number 10188.

The subject invention also provides a method for detecting in a sample an antigen indicative of the presence of atherosclerotic plaque, which comprises:
 (a) contacting the sample with the above described monoclonal antibody or fragment thereof under conditions such that the antibody or fragment binds to the antigen in the sample to form a detectable complex;
 (b) detecting the complex so formed; and
 (c) thereby detecting in the sample an antigen indicative of the presence of atherosclerotic plaque.

The subject invention further provides a method for quantitatively determining in a sample the concentration of an antigen indicative of the presence of atherosclerotic plaque, which comprises:
 (a) contacting a solid support with an excess of the above described monoclonal antibody or fragment thereof under conditions permitting the antibody or fragment to attach to the surface of the solid support;
 (b) removing unbound antibody or fragment;
 (c) contacting the resulting solid support to which the antibody or fragment is bound with the sample under conditions such that any antigen present in the sample binds to the bound antibody or fragment and forms a complex therewith;
 (d) removing any antigen which is not bound to the complex;
 (e) contacting any complex so formed with an excess of a detectable reagent which specifically binds to any antigen present in the complex so as to form a second complex which includes the antibody or fragment, the antigen, and the detectable reagent;
 (f) removing any detectable reagent which is not bound in the second complex;
 (g) quantitatively determining the concentration of detectable reagent present in the second complex; and
 (h) thereby quantitatively determining in the sample the concentration of an antigen indicative of the presence of atherosclerotic plaque.

The subject invention further provides the above described method wherein the detectable reagent comprises a monoclonal antibody or fragment thereof labeled with a detectable marker, wherein the monoclonal antibody is produced by hybridoma Z2D3 having ATCC Accession Number HB9840, hybridoma Z2D3/3E5 having ATCC Accession Number HB10485, rat myeloma cell line Z2D3 73/30 1D10 having ATCC Accession Number CRL 11203, or a CDR-grafted antibody comprising a CDR region from hybridoma Z2D3 or hybridoma Z2D3/3E5 and a framework and constant region from a human immunoglobulin.

The subject invention further provides a method for quantitatively determining in a sample the concentration of an antigen which is indicative of the presence of atherosclerotic plaque, which comprises:
 (a) contacting a solid support with a predetermined amount of the above described antibody or fragment thereof under conditions permitting the antibody or fragment to attach to the surface of the solid support;
 (b) removing any antibody or fragment not bound to the solid support;
 (c) contacting the resulting solid support to which the antibody or fragment is bound with a predetermined amount of an antigen labeled with a detectable marker, and with the sample under such conditions that labeled and sample antigens competitively bind to the antibody or fragment bound to the solid support and form a complex therewith;
 (d) removing any labeled and sample antigens which are not bound to the complex;
 (e) quantitatively determining the amount of labeled antigen bound to the solid support; and
 (f) thereby quantitatively determining in the sample the concentration of an antigen which is indicative of the presence of atherosclerotic plaque.

In the practice of the above described method step (e) may alternatively comprise quantitatively determining the amount of labeled antigen not bound to the solid support.

The subject invention also provides a method for quantitatively determining in a sample the concentration of an antigen which is indicative of the presence of atherosclerotic plaque, which comprises:
 (a) contacting a solid support with a predetermined amount of the above described monoclonal antibody or fragment thereof under conditions permitting the antibody or fragment to attach to the surface of the support;
 (b) removing any antibody or fragment not bound to the solid support;
 (c) contacting the resulting solid support to which the antibody or fragment is bound with the sample under conditions such that any antigen present in the sample binds to the bound antibody or fragment and forms a complex therewith;

(d) removing any antigen which is not bound to the complex;

(e) contacting the complex so formed with a predetermined amount of plaque antigen labeled with a detectable marker under conditions such that the labeled plaque antigen competes with the antigen from the sample for binding to the antibody or fragment;

(f) removing any labeled and sample antigens which are not bound to the complex;

(g) quantitatively determining the amount of labeled plaque antigen bound to the solid support; and (h) thereby quantitatively determining in the sample the concentration of an antigen which is indicative of the presence of atherosclerotic plaque.

In the practice of the above described method step (g) may alternatively comprise quantitatively determining the amount of labeled antigen not bound to the solid support.

The subject invention also provides the above described monoclonal antibody or fragment thereof conjugated to an enzyme capable of digesting a component of atherosclerotic plaque. In the practice of this invention the enzyme may be a proteinase, an elastase, a collagenase, or a saccharidase.

In a separate embodiment the enzyme is a proenzyme which, when activated, is converted to an enzyme capable of digesting a component of atherosclerotic plaque. Examples of proenzymes useful in the practice of this invention include a proenzyme form of fibroblastic collagenase, gelatinase, polymorphonuclear collagenase, granolocytic collagenase, stromelysin I, stromelysin II, or elastase.

In the practice of this invention the above described monoclonal antibody or fragment thereof conjugated to an enzyme or proenzyme may be genetically engineered so as to be expressed as a single molecule.

In a further preferred embodiment the above described monoclonal antibody or fragment thereof is a bifunctional antibody or fragment comprising a binding site specific for the enzyme and a binding site specific for an antigen indicative of atherosclerotic plaque. In the practice of this invention such a bifunctional antibody may be produced by a quadroma derived from the fusion of a hybridoma cell line Z2D3 having ATCC Accession Number HB9840, Z2D3/3E5 having ATCC Accession Number HB10485, or Z2D3 73/30 1D10 having ATCC Accession Number CRL 11203, with a hybridoma secreting a monoclonal antibody which specifically binds to the enzyme.

The subject invention also provides a pharmaceutical composition comprising the above described monoclonal antibody or fragment thereof bound to an enzyme or proenzyme in an amount effective to digest a component of atherosclerotic plaque, and a physiologically acceptable carrier.

The subject invention further provides a method for reducing the amount of atherosclerotic plaque in a blood vessel, which comprises:

(a) contacting the atherosclerotic plaque with a reagent comprising the antibody or fragment thereof bound to the enzyme or proenzyme under conditions and in an amount such that the reagent binds to, and digests, a component of the plaque; and (b) thereby reducing the amount of atherosclerotic plaque in a blood vessel.

In one embodiment the above described method further comprises contacting the blood vessel with an antibody which specifically binds to normal tissue and has bound thereto an inhibitor of an enzyme capable of digesting a component of atherosclerotic plaque under conditions such that the antibody binds to the normal tissue. In a preferred embodiment the antibody which specifically binds to normal intima or media is a purified antibody which specifically binds to an antigen synthesized by or present in normal smooth muscle cells and normal connective tissue surrounding arteries. In a more preferred embodiment the antibody is a monoclonal antibody produced by hybridoma Q10E7 having ATCC Accession Number 10188.

The subject invention also provides the above described monoclonal antibody or fragment thereof conjugated to cell growth inhibitors capable of preventing proliferation of atherosclerotic plaque.

The subject invention also provides a reagent for treating atherosclerosis, which comprises the above described monoclonal antibody or fragment thereof bound to a drug useful in treating atherosclerosis.

The subject invention also provides a method of treating atherosclerosis in a subject, which comprises administering to the subject an amount of the above described reagent effective to treat atherosclerosis.

The subject invention also provides a rat myeloma cell line designated Z2D3 73/30 1D10, having ATCC Accession Number CRL 11203. Hybridoma Z2D3 73/30 1D10 was deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md., 20852.

The subject invention also provides a murine-human chimeric monoclonal antibody produced by the rat myeloma cell line designated Z2D3 73/30 1D10 having ATCC Accession Number CRL 11203.

The subject invention also provides biologically active fragments of the above described human-murine chimeric monoclonal antibody. In separate embodiments the fragment may comprise the F(ab')$_2$, Fab', Fab, F$_V$, V$_H$, or V$_L$ antibody fragment. In further embodiments, the fragments are capable of specifically binding to an antigen recognized by a monoclonal antibody produced by hybridoma Z2D3, Z2D3/3E5, or Z2D3 73/30 1D10.

The subject invention also provides the above described antibody or fragment thereof labeled with a detectable marker. The choice of marker used will vary depending upon the application. However, the choice of marker is readily apparent to one skilled in the art. Examples of detectable markers useful in the practice of this invention have been described above.

The subject invention also provides the above described chimeric antibody or fragment thereof bound to a solid support. Examples of solid supports useful in the practice of this invention have been described above.

The subject invention also provides a reagent for use in imaging atherosclerotic plaque, which comprises the above described chimeric antibody or fragment thereof labeled with a detectable marker in an amount effective to image atherosclerotic plaque, and a physiologically acceptable carrier.

The subject invention further provides a method for imaging atherosclerotic plaque, which comprises:

(a) contacting the atherosclerotic plaque to be imaged with the above described reagent under conditions such that the reagent binds to the atherosclerotic plaque; and (b) detecting the detectable marker labelling the antibody or fragment in the reagent bound to the atherosclerotic plaque;

thereby imaging the atherosclerotic plaque.

In one embodiment the above described method can be used to image atherosclerotic plaque located in blood vessel walls of a subject.

The subject invention also provides a method for differentially imaging atherosclerotic plaque and normal tissue in a lumen, which comprises:

(a) contacting the lumen with an antibody which specifically binds to normal intima or media and which does not bind to atherosclerotic plaque, and which is labeled with a detectable marker;

(b) contacting the lumen with the above described reagent under conditions such that the reagent binds to the atherosclerotic plaque;

(c) detecting the detectable marker labeling the antibody of step (a) bound to the normal intima or media; and (d) detecting the detectable marker labeling the antibody or the fragment in the reagent of step (b) bound to the atherosclerotic plaque;

wherein the detectable marker labeling the antibody which specifically binds to normal intima or media is different from the detectable marker labeling the antibody or fragment in the reagent, thereby differentially imaging the atherosclerotic plaque and the normal tissue in the lumen.

In a preferred embodiment of the above described method the antibody which specifically binds to normal intima or media is a purified antibody which specifically binds to an antigen synthesized by or present in normal smooth muscle cells and normal connective tissue surrounding arteries. In a more preferred embodiment, the antibody is a monoclonal antibody produced by hybridoma Q10E7 having ATCC Accession Number 10188.

The subject invention also provides the above described chimeric antibody or fragment thereof bound to a chromophore capable of absorbing radiation having a plaque ablating wavelength. In the practice of this invention the chromophore absorbs light having a wavelength from about 190 nm to about 1100 nm. Examples of chromophores useful in the practice of this invention include fluorescein, rhodamine, tetracycline, hematoporphyrin, or β-carotene.

The subject invention provides a reagent for ablating atherosclerotic plaque comprising the above described chimeric antibody or fragment thereof bound to a chromophore capable of absorbing radiation having a plaque ablating wavelength in an amount effective to highlight the atherosclerotic plaque to be ablated and a physiologically acceptable carrier.

The subject invention further provides a method for ablating atherosclerotic plaque, which comprises:

(a) contacting atherosclerotic plaque with an effective amount of the above described so that the chimeric monoclonal antibody or fragment thereof present in the reagent binds to the atherosclerotic plaque forming an atherosclerotic plaque-chimeric monoclonal antibody complex;

(b) exposing the resulting complex to radiation having a plaque ablating wavelength under conditions such that the radiation is absorbed by the chromophore at a sufficient energy to ablate the atherosclerotic plaque; and (c) thereby ablating the atherosclerotic plaque.

In the practice of this invention the atherosclerotic plaque to be ablated may be located in a blood vessel. In such an instance the above described method for ablating atherosclerotic plaque comprises:

(a) contacting the normal lumen with an antibody which specifically binds to normal intima or media and has bound thereto a moiety capable of reflecting radiation of the plaque ablating wavelength;

(b) contacting the atherosclerotic plaque with the above described reagent;

(c) exposing the atherosclerotic plaque to the radiation having plaque ablating wavelength; and (d) thereby ablating the atherosclerotic plaque present in a blood vessel.

In a preferred embodiment the above described method, the antibody which specifically binds to normal intima or media is a purified antibody which specifically binds to an antigen synthesized by or present in normal smooth muscle cells and normal connective tissue surrounding arteries. In a more preferred embodiment the antibody is a monoclonal antibody produced by hybridoma Q10E7 having ATCC Accession Number 10188.

The subject invention also provides a method for detecting in a sample an antigen indicative of the presence of atherosclerotic plaque, which comprises:

(a) contacting the sample with the above described chimeric antibody or fragment thereof under conditions such that the antibody or fragment binds to the antigen in the sample to form a detectable complex;

(b) detecting the complex so formed; and (c) thereby detecting in the sample an antigen indicative of the presence of atherosclerotic plaque.

The subject invention further provides a method for quantitatively determining in a sample the concentration of an antigen indicative of the presence of atherosclerotic plaque, which comprises:

(a) contacting a solid support with an excess of the above described chimeric antibody or fragment thereof under conditions permitting the antibody or fragment to attach to the surface of the solid support;

(b) removing unbound antibody or fragment;

(c) contacting the resulting solid support to which the antibody or fragment is bound with the sample under conditions such that any antigen present in the sample binds to the bound antibody or fragment and forms a complex therewith;

(d) removing any antigen which is not bound to the complex;

(e) contacting any complex so formed with an excess of a detectable reagent which specifically binds to any antigen present in the complex so as to form a second complex which includes the antibody or fragment, the antigen, and the detectable reagent;

(f) removing any detectable reagent which is not bound in the second complex;

(g) quantitatively determining the concentration of detectable reagent present in the second complex; and (h) thereby quantitatively determining in the sample the concentration of an antigen indicative of the presence of atherosclerotic plaque.

The subject invention further provides the above-described method wherein the detectable reagent comprises a monoclonal antibody or fragment thereof labeled with a detectable marker, wherein the monoclonal antibody is produced by hybridoma Z2D3 having ATCC Accession Number HB9840, hybridoma Z2D3/3E5 having ATCC Accession Number HB10485, rat myeloma cell line Z2D3 73/30 1D10 having ATCC Accession Number CRL 11203, or a CDR-grafted antibody comprising a CDR region from hybridoma Z2D3 or hybridoma Z2D3/3E5 and a framework and constant region from a human immunoglobulin.

The subject invention further provides a method for quantitatively determining in a sample the concentration of an antigen which is indicative of the presence of atherosclerotic plaque, which comprises:

(a) contacting a solid support with a predetermined amount of the above described chimeric antibody or fragment thereof under conditions permitting the antibody or fragment to attach to the surface of the solid support;

(b) removing any antibody or fragment not bound to the solid support;

(c) contacting the resulting solid support to which the antibody or fragment is bound with a predetermined amount of an antigen labeled with a detectable marker, and with the sample under such conditions that labeled and sample antigens competitively bind to the antibody or fragment bound to the solid support and forms a complex therewith;

(d) removing any labeled and sample antigens which are not bound to the complex;

(e) quantitatively determining the amount of labeled antigen bound to the solid support; and (f) thereby quantitatively determining in the sample the concentration of an antigen which is indicative of the presence of atherosclerotic plaque.

In the practice of the above described method step (e) may alternatively comprise quantitatively determining the amount of labeled antigen not bound to the solid support.

The subject invention also provides a method for quantitatively determining in a sample the concentration of an antigen which is indicative of the presence of atherosclerotic plaque, which comprises:

(a) contacting a solid support with a predetermined amount of the above described chimeric antibody or fragment thereof under conditions permitting the antibody or fragment to attach to the surface of the support;

(b) removing any antibody or fragment not bound to the solid support;

(c) contacting the resulting solid support to which the antibody or fragment is bound with the sample under conditions such that any antigen present in the sample binds to the bound antibody or fragment and forms a complex therewith;

(d) removing any antigen which is not bound to the complex;

(e) contacting the complex so formed with a predetermined amount of plaque antigen labeled with a detectable marker under conditions such that the labeled plaque antigen competes with the antigen from the sample for binding to the antibody or fragment;

(f) removing any labeled and sample antigens which are not bound to the complex;

(g) quantitatively determining the amount of labeled plaque antigen bound to the solid support; and (h) thereby quantitatively determining in the sample the concentration of an antigen which is indicative of the presence of atherosclerotic plaque.

In the practice of the above described method step (g) may alternatively comprise quantitatively determining the amount of labeled antigen not bound to the solid support.

The subject invention also provides the above described chimeric antibody or fragment thereof conjugated to an enzyme capable of digesting a component of atherosclerotic plaque. In the practice of this invention the enzyme may be a proteinase, an elastase, a collagenase, or a saccharidase.

In a separate embodiment the enzyme is a proenzyme which, when activated, is converted to an enzyme capable of digesting a component of atherosclerotic plaque. Examples of proenzymes useful in the practice of this invention include a proenzyme form of fibroblastic collagenase, gelatinase, polymorphonuclear collagenase, granolocytic collagenase, stromelysin I, stromelysin II, or elastase.

In the practice of this invention the above described chimeric antibody or fragment thereof conjugated to an enzyme or proenzyme may be genetically engineered so as to be expressed as a single molecule.

In a further preferred embodiment the above described antibody or fragment thereof is a bifunctional antibody or fragment comprising a binding site specific for the enzyme and a binding site specific for an antigen indicative of atherosclerotic plaque. In the practice of this invention such a bifunctional antibody or fragment thereof may be produced by a quadroma derived from the fusion of a hybridoma cell line Z2D3 having ATCC Accession Number HB9840, Z2D3/3E5 having ATCC Accession Number HB10485, or Z2D3 73/30 1D10 having ATCC Accession Number CRL 11203, with a hybridoma secreting a monoclonal antibody which specifically binds to the enzyme.

The subject invention also provides a pharmaceutical composition comprising the above described chimeric antibody or fragment thereof bound to an enzyme or proenzyme in an amount effective to digest a component of atherosclerotic plaque, and a physiologically acceptable carrier.

The subject invention further provides a method for reducing the amount of atherosclerotic plaque in a blood vessel, which comprises:

(a) contacting the atherosclerotic plaque with a reagent comprising the chimeric antibody or fragment thereof bound to the enzyme or proenzyme under conditions and in an amount such that the reagent binds to, and digests, a component of the plaque; and (b) thereby reducing the amount of atherosclerotic plaque in a blood vessel.

In one embodiment the above described method further comprises contacting the blood vessel with an antibody which specifically binds to normal tissue and has bound thereto an inhibitor of an enzyme capable of digesting a component of atherosclerotic plaque under conditions such that the antibody binds to the normal tissue. In a preferred embodiment the antibody which specifically binds to normal intima or media is a purified antibody which specifically binds to an antigen synthesized by or present in normal smooth muscle cells and normal connective tissue surrounding arteries. In a more preferred embodiment the antibody is a monoclonal antibody produced by hybridoma Q10E7 having ATCC Accession Number 10188.

The subject invention also provides the above described chimeric antibody or fragment thereof conjugated to cell growth inhibitors capable of preventing proliferation of atherosclerotic plaque.

The subject invention also provides a reagent for treating atherosclerosis, which comprises the above described chimeric antibody or fragment thereof bound to a drug useful in treating atherosclerosis.

The subject invention also provides a method of treating atherosclerosis in a subject, which comprises administering to the subject an amount of the above described reagent effective to treat atherosclerosis.

The subject invention also provides a CDR-grafted antibody, comprising the complimentarity determining region (CDR) amino acid sequence from hybridoma Z2D3 having ATCC Accession Number HB9840, or hybridoma Z2D3/3E5 having ATCC Accession Number HB10485 and the framework and constant region amino acid sequences from a human immunoglobulin.

The subject invention also provides biologically active fragments of the above described CDR-grafted antibody. In separate embodiments the fragment may comprise the F(ab')$_2$, Fab', Fab, F$_V$, V$_H$, or V$_L$ antibody fragment. In further embodiments, the fragments are capable of specifically binding to an antigen recognized by a monoclonal antibody produced by hybridoma Z2D3, Z2D3/3E5, or Z2D3 73/30 1D10.

The subject invention also provides the above described CDR-grafted antibody or fragment thereof labeled with a detectable marker. The choice of marker used will vary depending upon the application. However, the choice of marker is readily apparent to one skilled in the art. Examples of detectable markers useful in the practice of this invention have been described above.

The subject invention also provides the above described CDR-grafted antibody or fragment thereof bound to a solid support. Examples of solid supports useful in the practice of this invention have been described above.

The subject invention also provides a reagent for use in imaging atherosclerotic plaque, which comprises the above described CDR-grafted antibody or fragment thereof labeled with a detectable marker in an amount effective to image atherosclerotic plaque, and a physiologically acceptable carrier.

The subject invention further provides a method for imaging atherosclerotic plaque, which comprises:
  (a) contacting the atherosclerotic plaque to be imaged with the above described reagent under conditions such that the reagent binds to the atherosclerotic plaque; and
  (b) detecting the detectable marker labelling the antibody or fragment in the reagent bound to the atherosclerotic plaque;
thereby imaging the atherosclerotic plaque.

In one embodiment the above described method can be used to image atherosclerotic plaque located in blood vessel walls of a subject.

The subject invention also provides a method for differentially imaging atherosclerotic plaque and normal tissue in a lumen, which comprises:
  (a) contacting the lumen with an antibody which specifically binds to normal intima or media and which does not bind to atherosclerotic plaque, and which is labeled with a detectable marker;
  (b) contacting the lumen with the above described reagent under conditions such that the reagent binds to the atherosclerotic plaque;
  (c) detecting the detectable marker labeling the antibody of step (a) bound to the normal intima or media; and
  (d) detecting the detectable marker labeling the antibody or the fragment in the reagent of step (b) bound to the atherosclerotic plaque;
wherein the detectable marker labeling the antibody which specifically binds to normal intima or media is different from the detectable marker labeling the antibody or fragment in the reagent, thereby differentially imaging the atherosclerotic plaque and the normal tissue in the lumen.

In a preferred embodiment of the above described method the antibody which specifically binds to normal intima or media is a purified antibody which specifically binds to an antigen synthesized by or present in normal smooth muscle cells and normal connective tissue surrounding arteries. In a more preferred embodiment, the antibody is a monoclonal antibody produced by hybridoma Q10E7 having ATCC Accession Number 10188.

The subject invention also provides the above described CDR-grafted antibody or fragment thereof bound to a chromophore capable of absorbing radiation having a plaque ablating wavelength. In the practice of this invention the chromophore absorbs light having a wavelength from about 190 nm to about 1100 nm. Examples of chromophores useful in the practice of this invention include fluorescein, rhodamine, tetracycline, hematoporphyrin, or β-carotene.

The subject invention provides a reagent for ablating atherosclerotic plaque comprising the above described CDR-grafted antibody or fragment thereof bound to a chromophore capable of absorbing radiation having a plaque ablating wavelength in an amount effective to highlight the atherosclerotic plaque to be ablated and a physiologically acceptable carrier.

The subject invention further provides a method for ablating atherosclerotic plaque, which comprises:
  (a) contacting atherosclerotic plaque with an effective amount of the above described so that the CDR-grafted monoclonal antibody or fragment thereof present in the reagent binds to the atherosclerotic plaque forming an atherosclerotic plaque-CDR-grafted monoclonal antibody complex;
  (b) exposing the resulting complex to radiation having a plaque ablating wavelength under conditions such that the radiation is absorbed by the chromophore at a sufficient energy to ablate the atherosclerotic plaque; and
  (c) thereby ablating the atherosclerotic plaque.

In the practice of this invention the atherosclerotic plaque to be ablated may be located in a blood vessel. In such an instance the above described method for ablating atherosclerotic plaque comprises:
  (a) contacting the normal lumen with an antibody which specifically binds to normal intima or media and has bound thereto a moiety capable of reflecting radiation of the plaque ablating wavelength;
  (b) contacting the atherosclerotic plaque with the above described reagent;
  (c) exposing the atherosclerotic plaque to the radiation having plaque ablating wavelength; and
  (d) thereby ablating the atherosclerotic plaque present in a blood vessel.

In a preferred embodiment the above described method, the antibody which specifically binds to normal intima or media is a purified antibody which specifically binds to an antigen synthesized by or present in normal smooth muscle cells and normal connective tissue surrounding arteries. In a more preferred embodiment the antibody is a monoclonal antibody produced by hybridoma Q10E7 having ATCC Accession Number 10188.

The subject invention also provides a method for detecting in a sample an antigen indicative of the presence of atherosclerotic plaque, which comprises:
  (a) contacting the sample with the above described CDR-grafted antibody or fragment thereof under conditions such that the antibody or fragment binds to the antigen in the sample to form a detectable complex;
  (b) detecting the complex so formed; and
  (c) thereby detecting in the sample an antigen indicative of the presence of atherosclerotic plaque.

The subject invention further provides a method for quantitatively determining in a sample the concentration of an antigen indicative of the presence of atherosclerotic plaque, which comprises:
  (a) contacting a solid support with an excess of the above described CDR-grafted antibody or fragment thereof under conditions permitting the antibody or fragment to attach to the surface of the solid support;

(b) removing unbound antibody or fragment;

(c) contacting the resulting solid support to which the antibody or fragment is bound with the sample under conditions such that any antigen present in the sample binds to the bound antibody or fragment and forms a complex therewith;

(d) removing any antigen which is not bound to the complex;

(e) contacting any complex so formed with an excess of a detectable reagent which specifically binds to any antigen present in the complex so as to form a second complex which includes the antibody or fragment, the antigen, and the detectable reagent;

(f) removing any detectable reagent which is not bound in the second complex;

(g) quantitatively determining the concentration of detectable reagent present in the second complex; and (h) thereby quantitatively determining in the sample the concentration of an antigen indicative of the presence of atherosclerotic plaque.

The subject invention further provides the above-described method wherein the detectable reagent comprises a monoclonal antibody or fragment thereof labeled with a detectable marker, wherein the monoclonal antibody is produced by hybridoma Z2D3 having ATCC Accession Number HB9840, hybridoma Z2D3/3E5 having ATCC Accession Number HB10485, rat myeloma cell line Z2D3 73/30 1D10 having ATCC Accession Number CRL 11203, or a CDR-grafted antibody comprising a CDR region from hybridoma Z2D3 or hybridoma Z2D3/3E5 and a framework and constant region from a human immunoglobulin.

The subject invention further provides a method for quantitatively determining in a sample the concentration atherosclerotic plaque, which comprises:

(a) contacting a solid support with a predetermined amount of the above described CDR-grafted antibody or fragment thereof under conditions permitting the antibody or fragment to attach to the surface of the solid support;

(b) removing any antibody or fragment not bound to the solid support;

(c) contacting the resulting solid support to which the antibody or fragment is bound with a predetermined amount of an antigen labeled with a detectable marker, and with the sample under such conditions that labeled and sample antigens competitively bind to the antibody or fragment bound to the solid support and forms a complex therewith;

(d) removing any labeled and sample antigens which are not bound to the complex;

(e) quantitatively determining the amount of labeled antigen bound to the solid support;

(f) thereby quantitatively determining in the sample the concentration of an antigen which is indicative of the presence of atherosclerotic plaque.

In the practice of the above described method step (e) may alternatively comprise quantitatively determining the amount of labeled antigen not bound to the solid support.

The subject invention also provides a method for quantitatively determining in a sample the concentration of an antigen which is indicative of the presence of atherosclerotic plaque, which comprises:

(a) contacting a solid support with a predetermined amount of the above described CDR-grafted antibody or fragment thereof under conditions permitting the antibody or fragment to attach to the surface of the support;

(b) removing any antibody or fragment not bound to the solid support;

(c) contacting the resulting solid support to which the antibody or fragment is bound with the sample under conditions such that any antigen present in the sample binds to the bound antibody or fragment and forms a complex therewith;

(d) removing any antigen which is not bound to the complex;

(e) contacting the complex so formed with a predetermined amount of plaque antigen labeled with a detectable marker under conditions such that the labeled plaque antigen competes with the antigen from the sample for binding to the antibody or fragment;

(f) removing any labeled and sample antigens which are not bound to the complex;

(g) quantitatively determining the amount of labeled plaque antigen bound to the solid support; and (h) thereby quantitatively determining in the sample the concentration of an antigen which is indicative of the presence of atherosclerotic plaque.

In the practice of the above described method step (g) may alternatively comprise quantitatively determining the amount of labeled antigen not bound to the solid support.

The subject invention also provides the above described CDR-grafted antibody or fragment thereof conjugated to an enzyme capable of digesting a component of atherosclerotic plaque. In the practice of this invention the enzyme may be a proteinase, an elastase, a collagenase, or a saccharidase.

In a separate embodiment the enzyme is a proenzyme which, when activated, is converted to an enzyme capable of digesting a component of atherosclerotic plaque. Examples of proenzymes useful in the practice of this invention include a proenzyme form of fibroblastic collagenase, gelatinase, polymorphonuclear collagenase, granolocytic collagenase, stromelysin I, stromelysin II, or elastase.

In the practice of this invention the above described CDR-grafted antibody or fragment thereof conjugated to an enzyme or proenzyme may be genetically engineered so as to be expressed as a single molecule.

In a further preferred embodiment the above described antibody or fragment thereof is a bifunctional antibody or fragment comprising a binding site specific for the enzyme and a binding site specific for an antigen indicative of atherosclerotic plaque. In the practice of this invention such a bifunctional antibody may be produced by a quadroma derived from the fusion of a hybridoma cell line Z2D3 having ATCC Accession Number HB9840, Z2D3/3E5 having ATCC Accession Number HB10485, or Z2D3 73/30 1D10 having ATCC Accession Number CRL 11203, with a hybridoma secreting a monoclonal antibody which specifically binds to the enzyme.

The subject invention also provides a pharmaceutical composition comprising the above described CDR-grafted antibody or fragment thereof bound to an enzyme or proenzyme in an amount effective to digest a component of atherosclerotic plaque, and a physiologically acceptable carrier.

The subject invention further provides a method for reducing the amount of atherosclerotic plaque in a blood vessel, which comprises:

(a) contacting the atherosclerotic plaque with a reagent comprising the CDR-grafted antibody or fragment thereof bound to the enzyme or proenzyme under conditions and in an amount such that the reagent binds to, and digests, a component of the plaque; and (b) thereby reducing the amount of atherosclerotic plaque in a blood vessel.

In one embodiment the above described method further comprises contacting the blood vessel with an antibody which specifically binds to normal tissue and has bound thereto an inhibitor of an enzyme capable of digesting a component of atherosclerotic plaque under conditions such that the antibody binds to the normal tissue. In a preferred embodiment the antibody which specifically binds to normal intima or media is a purified antibody which specifically binds to an antigen synthesized by or present in normal smooth muscle cells and normal connective tissue surrounding arteries. In a more preferred embodiment the antibody is a monoclonal antibody produced by hybridoma Q10E7 having ATCC Accession Number 10188.

The subject invention also provides the above described CDR-grafted antibody or fragment thereof conjugated to cell growth inhibitors capable of preventing proliferation of atherosclerotic plaque.

The subject invention also provides a reagent for treating atherosclerosis, which comprises the above described CDR-grafted antibody or fragment thereof bound to a drug useful in treating atherosclerosis.

The subject invention also provides a method of treating atherosclerosis in a subject, which comprises administering to the subject an amount of the above described reagent effective to treat atherosclerosis.

The subject invention further provides a peptide having an amino acid sequence which is the same or substantially the same as the amino acid sequence of the variable region of the heavy chain of the above described murine-human chimeric monoclonal antibody. In one embodiment the peptide has the amino acid sequence of SEQ ID NO: 18. In another embodiment the peptide has the amino acid sequence of SEQ ID NO: 19.

The subject invention also provides a peptide having an amino acid sequence which is the same or substantially the same as the amino acid sequence of the variable region of the light chain of the above described human-murine chimeric monoclonal antibody. In one embodiment of the invention the peptide has the amino acid sequence of SEQ ID NO: 63.

The subject invention also provides a peptide which comprises an amino acid sequence or a combination of amino acid sequences, each of which amino acid sequences is the same or substantially the same as the amino acid sequence of a complimentarity determining region (CDR) of the above described human-murine chimeric monoclonal antibody.

In one embodiment of the peptide, the peptide comprises an amino acid sequence which is the same or substantially the same as the amino acid sequence of a complimentarily determining region of the variable region of the heavy chain of the chimeric monoclonal antibody. In separate embodiments the above described peptide has the amino acid sequence of SEQ ID NO: 22, SEQ ID NO: 25, or SEQ ID NO: 28.

In another embodiment of the peptide, the peptide comprises an amino acid sequence which is the same or substantially the same as the complimentarity determining region of the variable region of the light chain of the chimeric monoclonal antibody. In separate embodiments the above described peptide has the amino acid sequence of SEQ ID NO: 66, SEQ ID NO: 69, or SEQ ID NO: 72.

The subject invention also provides the above-described peptide recombinantly produced. In one embodiment the above described recombinant peptide can be modified by site-directed mutagenesis. Preferably, any of the aforementioned peptides have the same binding specificity as antibodies produced by hybrodimas Z2D3, Z2D3/3E5, or Z2D3 73/30 1D10.

The subject invention also provides an isolated nucleic acid molecule, having a nucleotide sequence encoding a peptide whose amino acid sequence is the same or substantially the same as the amino acid sequence of the variable region of the heavy chain of the above-described human-murine chimeric monoclonal antibody. The isolated nucleic acid molecule may be a RNA, DNA or cDNA molecule. In one embodiment the isolated nucleic acid molecule is a DNA molecule and may have the sequence of SEQ ID NO: 16 or SEQ ID NO: 17.

The subject invention also provides an isolated nucleic acid molecule having a nucleotide sequence encoding a peptide whose amino acid sequence is the same or substantially the same as the amino acid sequence of the variable region of the light chain of the above described human-murine chimeric monoclonal antibody. The isolated nucleic acid molecule may be a RNA, DNA or cDNA molecule. In one embodiment the isolated nucleic acid molecule is a DNA molecule and may have the sequence of SEQ ID NO: 61 or SEQ ID NO: 62.

The subject invention also provides an isolated nucleic acid molecule having a nucleotide sequence encoding an amino acid sequence which is the same or substantially the same as the amino acid sequence of a complimentarity determining region of the above described human-murine chimeric monoclonal antibody. The isolated nucleic acid molecule may be a RNA, DNA or cDNA molecule.

In one embodiment the above described nucleic acid molecule encodes an amino acid sequence which is the same as or substantially the same as the amino acid sequence of a complimentarity determining region of the variable region of the heavy chain of the chimeric monoclonal antibody. In separate embodiments the above described nucleic acid molecule is a DNA molecule and has the sequence of SEQ ID NO: 20, SEQ ID NO: 23, SEQ ID NO: 26, SEQ ID NO: 21, SEQ ID NO: 24, or SEQ ID NO: 27.

In another embodiment the above described nucleic acid molecule encodes an amino acid sequence which is the same or substantially the same as the amino acid sequence of a complimentarity determining region of the variable region of the light chain of the chimeric monoclonal antibody. In separate embodiments the above described nucleic acid molecule is a DNA molecule and has the sequence of SEQ ID NO: 64, SEQ ID NO: 67, SEQ ID NO: 70, SEQ ID NO: 65, SEQ ID NO: 68, or SEQ ID NO: 71.

Preferably, any of the aforementioned nucleic acid molecules encode for peptides which have the same or substantially the same binding specificity as antibodies produced by hybridomas Z2D3, Z2D3/3E5, or Z2D3 73/30 1D10.

As indicated above, the subject invention provides a peptide which comprises an amino acid sequence or combination of amino acid sequences, each of which amino acid sequences is the same or substantially the same as the amino acid sequence of a complimentarily determining region (CDR) of a murine-human chimeric monoclonal antibody produced by a rat myeloma cell line designated Z2D3 73/30 1D10.

The subject invention further provides a proteinaceous construct comprising a binding site which comprises an amino acid sequence or combination of amino acid sequences, each of which amino acid sequences is the same or substantially the same as the amino acid sequence of a complimentarity determining region (CDR) of a murine-human chimeric monoclonal antibody produced by a rat myeloma cell line designated Z2D3 73/30 1D10.

As used herein the term "proteinaceous construct" indicates any molecule which comprises amino acid moieties linked to one another by peptide bonds. Proteinaceous constructs therefore include peptides, polypeptides, as well as molecules comprising peptide and/or polypeptide subunits. Proteinaceous constructs are known to those of ordinary skill in the art. The proteinaceous construct of the subject invention is, in different non-limiting embodiments, a monoclonal antibody; a fragment of a monoclonal antibody; a "diabody", i.e. a proteinaceous construct which comprises two binding sites having either the same or different binding specificities from one another; a "single-stranded antibody", i.e. a genetically engineered strand of amino acids connected by peptide bonds, which strand comprises one or more sequences each of which corresponds to a variable region of a particular antibody; a polypeptide; and a peptide.

In one embodiment, the proteinaceous construct is the aforementioned peptide of the subject invention which comprises an amino acid sequence or combination of amino acid sequences, each of which amino acid sequences is the same or substantially the same as the amino acid sequence of a complimentarity determining region (CDR) of a murine-human chimeric monoclonal antibody produced by a rat myeloma cell line designated Z2D3 73/30 1D10.

As used herein, an amino acid sequence which is "substantially the same" as the amino acid sequence of a CDR of an antibody produced by the cell line Z2D3 73/30 1D10 is any sequence which has the same binding specificity as the CDR. In one embodiment, an amino acid sequence which is substantially the same as the amino acid sequence of such a CDR is an amino acid sequence which is at least about 90% homologous to the CDR. In another embodiment, the amino acid sequence is at least about 95% homologous to the CDR.

When an amino acid sequences of the proteinaceous construct of the subject invention is only substantially the same as, i.e. not identical to, the amino acid sequence of a complimentarity determining region of the monoclonal antibody produced by the rat myeloma cell line designated Z2D3 73/30 1D10, said substantially same sequence is, in one embodiment, obtained from a known antibody, such as the antibody CH34, the variable region sequence of which is set forth in Table 7. An amino acid sequence which is substantially the same as the sequence of a CDR of an antibody produced by Z2D3 73/30 1D10 may be obtained from a known antibody by any means known to those of ordinary skill in the art, for example, by excising the sequence from the known antibody, or by chemically synthesizing de novo from amino acid monomers a peptide which has the same sequence as the sequence from the known antibody.

This invention further provides the aforementioned proteinaceous construct of the subject invention labeled with a detectable marker. In one embodiment, the proteinaceous construct labeled with the detectable marker of the subject invention is a known antibody which comprises at least one amino acid sequence which is substantially the same as a CDR of the Z2D3 73/30 1D10 antibody, such as the antibody CH34, labeled with a detectable marker.

This invention also provides the aforementioned proteinaceous construct bound to a solid support. In one embodiment, the proteinaceous construct bound to the solid support of the subject invention is a known antibody which comprises an amino acid sequence which is substantially the same as a CDR of the Z2D3 73/30 1D10 antibody, such as CH34, bound to a solid support.

This invention also provides a reagent for use in imaging atherosclerotic plaque which comprises the aforementioned proteinaceous construct of the subject invention labeled with a detectable marker, in an amount effective to image atherosclerotic plaque, and a physiologically acceptable carrier.

This invention further provides a method for imaging atherosclerotic plaque, which comprises: (a) contacting the atherosclerotic plaque to be imaged with the above-described reagent, under conditions such that the reagent binds to the atherosclerotic plaque; and (b) detecting the detectable marker labelling the proteinaceous construct in the reagent bound to the atherosclerotic plaque; thereby imaging the atherosclerotic plaque.

This invention further provides a method for differentially imaging atherosclerotic plaque and normal tissue in a lumen, which comprises: (a) contacting the lumen with an antibody which specifically binds to normal intima or media and which does not bind to atherosclerotic plaque, and which is labeled with a detectable marker; (b) contacting the lumen with the above-described reagent of the subject invention under conditions such that the reagent binds to the atherosclerotic plaque; (c) detecting the detectable marker labeling the antibody of step (a) bound to the normal intima or media; and (d) detecting the detectable marker labeling the proteinaceous construct in the reagent of step (b) bound to the atherosclerotic plaque; wherein the detectable marker labeling the antibody which specifically binds to normal intima or media is different from the detectable marker labeling the proteinaceous construct in the reagent, thereby differentially imaging the atherosclerotic plaque and the normal tissue in the lumen.

In one embodiment of the above-described method, the antibody which specifically binds to normal intima or media is a purified antibody which specifically binds to an antigen synthesized by or present in normal smooth muscle cells and normal connective tissue surrounding arteries. In an embodiment wherein the antibody is a purified antibody which specifically binds to an antigen synthesized by or present in normal smooth muscle cells and normal connective tissue surrounding arteries, the antibody is a monoclonal antibody produced by hybridoma Q10E7 having ATCC Accession Number 10188.

This invention also provides the aforementioned proteinaceous construct of the subject invention, bound to a chromophore capable of absorbing radiation having a plaque ablating wavelength. In one embodiment, the chromophore absorbs light having a wavelength from about 190 nm to about 1100 nm. In different embodiments wherein the chromophore absorbs light having a wavelength from about 190 nm to about 1100 nm, the chromophore is fluorescein, rhodamine, tetracycline, hematoporphyrin, and β-carotene. In another embodiment, the proteinaceous construct is a known antibody, such as the antibody CH34, which comprises at least one amino acid sequence which is substantially the same as the amino acid sequence of a CDR of the Z2D3 73/30 1D10 monoclonal antibody bound to a chromophore capable of absorbing radiation having a plaque ablating wavelength.

Still further, this invention provides a reagent for ablating atherosclerotic plaque comprising the aforementioned proteinaceous construct of the subject invention bound to a chromophore capable of absorbing radiation having a plaque ablating wavelength in an amount effective to highlight the atherosclerotic plaque to be ablated and a physiologically acceptable carrier.

This invention also provides a method for ablating atherosclerotic plaque, which comprises: (a) contacting atherosclerotic plaque with an effective amount of the above-described reagent, so that the proteinaceous construct present in the reagent binds to the atherosclerotic plaque forming an atherosclerotic plaque-construct complex; (b) exposing the resulting complex to radiation having a plaque ablating wavelength under conditions such that the radiation is absorbed by the chromophore at a sufficient energy to ablate the atherosclerotic plaque; and (c) thereby ablating the atherosclerotic plaque.

This invention also provides a method for ablating atherosclerotic plaque in a blood vessel, which comprises: (a) contacting the normal lumen with an antibody which specifically binds to normal intima or media and has bound thereto a moiety capable of reflecting radiation of the plaque ablating wavelength; (b) contacting the atherosclerotic plaque with the above-described reagent; (c) exposing the atherosclerotic plaque to the radiation having plaque ablating wavelength; and (d) thereby ablating the atherosclerotic plaque present in a blood vessel.

In one embodiment of the above-described method of the subject invention, the antibody which specifically binds to normal intima or media is a purified antibody which specifically binds to an antigen synthesized by or present in normal smooth muscle cells and normal connective tissue surrounding arteries. In an embodiment wherein the antibody is a purified antibody which specifically binds to an antigen synthesized by or present in normal smooth muscle cells and normal connective tissue surrounding arteries, the antibody is a monoclonal antibody produced by hybridoma Q10E7 having ATCC Accession Number 10188.

This invention also provides a method for detecting in a sample an antigen indicative of the presence of atherosclerotic plaque, which comprises: (a) contacting the sample with the aforementioned proteinaceous construct of the subject invention, under conditions such that the construct binds to the antigen in the sample to form a detectable complex; (b) detecting the complex so formed; and (c) thereby detecting in the sample an antigen indicative of the presence of atherosclerotic plaque. In one embodiment of this method, the proteinaceous construct is a known antibody, such as CH34, which comprises one or more amino acid sequences each of which is substantially the same as a CDR of the Z2D3 73/30 1D10 monoclonal antibody.

This invention also provides a method for quantitatively determining in a sample the concentration of an antigen indicative of the presence of atherosclerotic plaque, which comprises: (a) contacting a solid support with an excess of the aforementioned proteinaceous construct of the subject invention, under conditions permitting the construct to attach to the surface of the solid support; (b) removing unbound proteinaceous construct; (c) contacting the resulting solid support to which the construct is bound with the sample under conditions such that any antigen present in the sample binds to the bound proteinaceous construct and forms a complex therewith; (d) removing any antigen which is not bound to the construct; (e) contacting any complex so formed with an excess of a detectable reagent which specifically binds to any antigen present in the complex so as to form a second complex which includes the proteinaceous construct, the antigen, and the detectable reagent; (f) removing any detectable reagent which is not bound in the second complex; (g) quantitatively determining the concentration of detectable reagent present in the second complex; and (h) thereby quantitatively determining in the sample the concentration of an antigen indicative of the presence of atherosclerotic plaque. In one embodiment of this method, the proteinaceous construct is a known antibody, such as CH34, which comprises one or more amino acid sequences each of which is substantially the same as a CDR of the Z2D3 73/30 1D10 monoclonal antibody.

In one embodiment of the above-described method, the detectable reagent comprises a monoclonal antibody or fragment thereof labeled with a detectable marker, wherein the monoclonal antibody is produced by hybridoma Z2D3 having ATCC Accession Number HB9840, hybridoma Z2D3/3E5 having ATCC Accession Number HB10485, rat myeloma cell line Z2D3 73/30 1D10 having ATCC Accession Number CRL 11203, or a CDR-grafted antibody comprising a CDR region from hybridoma Z2D3 or hybridoma Z2D3/3E5 and a framework and constant region from a human immunoglobulin.

This invention further provides a method for quantitatively determining in a sample the concentration of an antigen which is indicative of the presence of atherosclerotic plaque, which comprises: (a) contacting a solid support with a predetermined amount of the aforementioned proteinaceous construct of the subject invention, under conditions permitting the construct to attach to the surface of the solid support; (b) removing any proteinaceous construct not bound to the solid support; (c) contacting the resulting solid support to which the construct is bound with a predetermined amount of an antigen labeled with a detectable marker, and with the sample under such conditions that labeled and sample antigens competitively bind to the proteinaceous construct bound to the solid support and form a complex therewith; (d) removing any labeled and sample antigens which are not bound to the complex; (e) quantitatively determining the amount of labeled antigen bound to the solid support; and (f) thereby quantitatively determining in the sample the concentration of an antigen which is indicative of the presence of atherosclerotic plaque. In one embodiment of this method, the proteinaceous construct is a known antibody, such as CH34, which comprises one or more amino acid sequences each of which is substantially the same as a CDR of the Z2D3 73/30 1D10 monoclonal antibody. In another embodiment, step (e) of this method comprises quantitatively determining the amount of labeled antigen not bound to the solid support.

This invention also provides a method for quantitatively determining in a sample the concentration of an antigen which is indicative of the presence of atherosclerotic plaque, which comprises: (a) contacting a solid support with a predetermined amount of the aforementioned proteinaceous construct of the subject invention, under conditions permitting the construct to attach to the surface of the support; (b) removing any construct not bound to the solid support; (c) contacting the resulting solid support to which the proteinaceous construct is bound with the sample under conditions such that any antigen present in the sample binds to the bound construct and forms a complex therewith; (d) removing any antigen which is not bound to the complex; (e) contacting the complex so formed with a predetermined amount of plaque antigen labeled with a detectable marker under conditions such that the labeled plaque antigen competes with the antigen from the sample for binding to the proteinaceous construct; (f) removing any labeled and sample antigens which are not bound to the complex; (g) quantitatively determining the amount of labeled plaque antigen bound to the solid support; and (h) thereby quantitatively determining in the sample the concentration of an antigen which is indicative of the presence of atherosclerotic plaque. In one embodiment of this method, the proteinaceous construct is a known antibody, such as CH34, which comprises one or more amino acid sequences each of which is substantially the same as a CDR of the Z2D3 73/30 1D10 monoclonal antibody. In another embodiment, step (g) of this method comprises quantitatively determining the amount of labeled antigen not bound to the solid support.

Still further, this invention provides the aforementioned proteinaceous construct of the subject invention conjugated to an enzyme capable of digesting a component of atherosclerotic plaque. In one embodiment, the proteinaceous construct conjugated to the enzyme capable of digesting a component of atherosclerotic plaque is a known antibody, such as the antibody CH34, which comprises one or more amino acid sequences which are substantially the same as the sequence of a CDR of the Z2D3 73/30 1D10 monoclonal antibody.

In a further embodiment, the proteinaceous construct is conjugated to a proenzyme which, when activated, is converted to an enzyme capable of digesting a component of atherosclerotic plaque.

In another embodiment, the proteinaceous construct and the enzyme comprise a single molecule.

In still another embodiment, the proteinaceous construct is a bifunctional peptide comprising a binding site specific for the enzyme and a binding site specific for the antigen.

In different embodiments of the subject invention, the enzyme capable of digesting a component of atherosclerotic plaque is a proteinase, an elastase, a collagenase, and a saccharidase.

In different embodiments of the subject invention when the enzyme is a proenzyme, the proenzyme is a proenzyme form of fibroblastic collagenase, gelatinase, polymorphonuclear collagenase, granolocytic collagenase, stromelysin I, stromelysin II, and elastase.

Still further, this invention provides a reagent useful for reducing atherosclerotic plaque which comprises the above-described proteinaceous construct conjugated to an enzyme capable of digesting a component of atherosclerotic plaque.

This invention also provides a method for reducing the amount of atherosclerotic plaque in a blood vessel, which comprises: (a) contacting the atherosclerotic plaque with a above-described reagent comprising the aforementioned proteinaceous construct of the subject invention conjugated to an enzyme capable of digesting a component of atherosclerotic plaque under conditions and in an amount such that the reagent binds to, and digests, a component of the plaque; and (b) thereby reducing the amount of atherosclerotic plaque in a blood vessel.

In one embodiment of the above-described method for reducing the amount of atherosclerotic plaque in a blood vessel, the method further comprising contacting the blood vessel with an antibody which specifically binds to normal intima or media and has bound thereto an inhibitor of an enzyme capable of digesting a component of atherosclerotic plaque under conditions such that the antibody which specifically binds to normal intima or media binds to the normal intima or media in the blood vessel. The antibody which specifically binds to normal intima or media may be a purified antibody which specifically binds to an antigen synthesized by or present in normal smooth muscle cells and normal connective tissue surrounding arteries. In an embodiment wherein the antibody which specifically binds to normal intima or media is a purified antibody which specifically binds to an antigen synthesized by or present in normal smooth muscle cells and normal connective tissue surrounding arteries, the antibody is a monoclonal antibody produced by hybridoma Q10E7 having ATCC Accession Number 10188.

This invention further provides the aforementioned proteinaceous construct of the subject invention conjugated to cell growth inhibitors capable of preventing proliferation of atherosclerotic plaque. In one embodiment, the proteinaceous construct conjugated to such cell growth inhibitors is a known antibody, such as the antibody CH34, which comprises one or more amino acid sequences which are substantially the same as the sequence of a CDR of the Z2D3 73/30 1D10 monoclonal antibody. The subject invention also provides a reagent comprising the aforementioned proteinaceous construct conjugated to cell growth inhibitors capable of preventing proliferation of atherosclerotic plaque.

This invention further provides a pharmaceutical composition for treating atherosclerosis which comprises the aforementioned proteinaceous construct of the subject invention bound to a drug useful in treating atherosclerosis. In one embodiment of this pharmaceutical composition, the proteinaceous construct bound to the drug is a known antibody, such as the antibody CH34, which comprises one or more amino acid sequences which are substantially the same as the sequence of a CDR of the Z2D3 73/30 1D10 monoclonal antibody.

Finally, this invention provides a method of treating atherosclerosis in a subject, which comprises administering to the subject an amount of the above-described pharmaceutical composition comprising the proteinaceous construct of the subject invention bound to a drug useful in treating atherosclerosis effective to treat atherosclerosis.

This invention is further illustrated in the Experimental Details section which follows. The Experimental Details section and Examples contained therein are set forth to aid in an understanding of the invention, and are not intended, and should not be interpreted, to limit in any way the invention set forth in the claims which follow thereafter.

Experimental Details

The Experimental Details Section is organized as follows:

I. Development Of Anti-Human Atherosclerotic Plaque Monoclonal Antibody, Z2D3

II. Development Of Anti-Human Atherosclerosis Plaque Monoclonal Antibody, Z2D3/3E5

III. Immunohistological Staining With The Z2D3 Monoclonal Antibody

IV. Characterization Of Human Atherosclerotic Plaque Antigen Recognized By Monoclonal Antibody Z2D3

V. Development Of Chimeric Z2D3 Monoclonal Antibody

VI. Development Of Monoclonal Antibodies Using Surrogate Antigens As The Immunogens VII. Imaging Of Atherosclerotic Plaque VIII. Treatment Of Atherosclerotic Plaque I. Development Of Anti-Human Atherosclerotic Plaque Monoclonal Antibody, Z2D3

I-I. Preparation Of Human Atherosclerotic Plaque Immunogen

Human arterial sections containing significant fibro-fatty atherosclerotic plaque were harvested at autopsy within six hours of death and quickly frozen at −80° C. At the time of processing, the arterial samples were thawed at room temperature and washed three times with 10 mM phosphate buffered saline pH 7.3 (PBS) containing 0.02% sodium azide to remove blood and other particulates. The atherosclerotic plaque was carefully dissected from the surrounding normal-appearing artery, and the artery discarded. Significant calcification was dissected away. The remaining fibro-fatty plaque was cut into 2 mm pieces and added to a two-fold volume of cold PBS with 5 $\mu$M of the protease inhibitor phenylmethylsulfonyl fluoride (PMSF), (Sigma Chemical Co., St. Louis, Mo.), and 13 mM ethylenediaminetetraacetic acid (EDTA). This suspension was homogenized on ice in a small Virtis® homogenizer (The Viritis Company, Gardiner, N.Y.) for 2 minutes. The homogenized suspension was passed through two layers of loose mesh gauze to remove large particulates. It was then centrifuged at 40,000×g for 30 minutes at 6° C. The plaque supernatant was carefully removed and the precipitate was discarded.

The protein content of the plaque supernatant was estimated spectrophotometrically using an extinction coefficient of 1.0 at 280 nm for a 1 mg/mL solution. In order to separate and identify molecular fractions possessing antigens which are highly specific for the atherosclerotic plaque, the plaque supernatant was fractionated by high performance liquid chromatography (HPLC) on a 55×200 mm Bio-Gel® TSK DEAE 5 PW anion exchange column (Bio-Rad, Richmond, Calif.). The DEAE column was equilibrated with 20 mM sodium phosphate buffer, pH 7.2 at a flow rate of 6 mL/minute and the plaque supernatant, containing approximately 500 mg of total protein, was applied. After washing the column with equilibration buffer, the bound plaque components were eluted with a linear gradient of 0 to 500 mM sodium chloride in phosphate buffer in a total volume of 1.4 L. Fraction volume was 6 mL.

In order to determine which fractions contained specific atherosclerotic antigens, the fractions were assayed using an enzyme-linked immunosorbent assay (ELISA). For a review of ELISA techniques, see Voller, A., et al., ["The Enzyme-Linked Immunosorbent Assay (ELISA)", vols. 1 and 2, Micro Systems, Guernsey, U.K.].

The plaque antigen ELISA was performed as follows. Duplicate aliquots, 100 μL each, were removed from each fraction and were applied to separate wells in black Immulon II microtiter plates (Dynatech, Chantilly, Va.). The plates were covered and incubated overnight at 4° C. The following morning, the aliquoted samples were removed and the plates blocked for one hour at room temperature with a 1% solution of bovine serum albumin (BSA) (Sigma) in PBS. The plates were then washed four times, 200 μL per well, with PBS containing 0.1% Triton-X-100 (Sigma) and 0.05% TWEEN-20 (Polyoxyethylenesorbitan monolaurate) (Sigma) (wash buffer).

Serum samples had previously been collected from approximately 100 patients with severe atherosclerotic disease. These sera were pooled and an aliquot was diluted 100-fold in PBS containing 5% BSA. Aliquots of this solution, 100 μL per well, were applied to one of the duplicate wells for each ion-exchange fraction. As a control, a serum pool was collected from approximately 100 males and females under age 20. A 100-fold dilution of this pool was prepared in PBS containing 5% BSA. A 100 μL aliquot of this diluted normal serum pool was applied to the second of the duplicate wells for each ion-exchange fraction. The diluted sera were incubated in the wells for two hours at ambient temperature. The plates were then washed four times with wash buffer.

Alkaline phosphatase conjugated goat anti-human IgG (Zymed, So. San Francisco, Calif.) was diluted 2000-fold in 20 mM 2-amino-2-hydroxymethyl-1,3-propanediol (Tris) chloride, 150 mM sodium chloride pH 7.5 containing 0.02% sodium azide. This solution was applied to the ELISA plate, 100 μL per well, and incubated for two hours at ambient temperature. The wells were then washed four times with wash buffer and 100 μL of 4-methylumbelliferyl phosphate substrate solution (3M Diagnostics, Santa Clara, Calif.) applied to each well. The plates were read at five minute intervals with a Fluorofast 96-well fluorometer (3M Diagnostics). Each pair of wells corresponding to individual fractions from the ion-exchange chromatography step above were evaluated for the ratio of fluorescent signal between the well having been incubated with pooled atherosclerotic patients and the well incubated with pooled sera from young healthy individuals.

Only one group of fractions was positive, exhibiting a signal ratio greater than 3:1. The contents of these tubes were pooled and dialyzed against PBS using 3500 MW cut-off Spectrapor® dialysis tubing (Spectrum Medical Industries, Los Angeles, Calif.). To obtain a more purified antigen fraction the dialyzed pool was reprocessed by ion-exchange chromatography as outlined above and the resulting fractions again assayed by ELISA. Those tubes whose contents possessed antigen activity with a signal ration of 4:1 or greater were retained and their contents pooled. The pooled solution was dialyzed against PBS with PMSF and then concentrated in a Diaflo concentrating system with a 1000 MW cutoff filter (Amicon Div., W. R. Grace, Danwere, Mass.) to attain a protein content of approximately 1 mg/mL. This solution, extract I, was stored at 4° C.

Monoclonal antibody 15H5 (ATCC Accession No. HB9839) is specific for an extracellular atherosclerotic antigen. The 15H5 antigen is, in part, responsible for the generation of autoantibodies during the development of atherosclerotic lesions. In order to further purify the antigen in extract I, the following procedure was performed. Purified 15H5 monoclonal antibody was coupled to cyanogen bromide activated Sepharose® 4 B (Pharmacia LKB Biotechnology, Uppsala, Sweden) at a ratio of approximately 5 mg of antibody per mL of gel in accordance with the manufacturers instructions ["Affinity Chromatography", Pharmacia]. A column was prepared with this resin. A portion of extract I was applied to the column and the column washed with PBS. The bound antigen was eluted with potassium thiocyanate and the antigen dialyzed against PBS. The dialyzed solution, extract II, was stored at 4° C.

I-2. Immunization Of Mice With Human Plaque Immunogen

Balb/c mice (Simonsen Labs, Gilroy, Calif.) seven weeks old were immunized over a six-month period with human plaque immunogen, extracts I and II, obtained as described in section I-1. At Day 0, for each mouse, 100 μg of the antigen extract I were emulsified with Freund's Complete Adjuvant, (Difco Laboratories, Detroit, Mich.), and injected subcutaneously at multiple sites. At Day 16, 42 and 82, 50 μg of antigen extract I were emulsified in Freund's Incomplete Adjuvant (Difco) and injected subcutaneously into each mouse. At days 153, 184, and 191, 50 μg of antigen extract II were emulsified in Freund's Incomplete Adjuvant and injected subcutaneously into each mouse. At day 213, 50 μg of extract II in saline was injected intravenously into mouse number 2. Three days later, the spleen of the mouse number 2 was taken for fusion.

I-3. Development Of Hybridoma Cell Line Producing Monoclonal Antibodies Targeted Against Human Plaque Antigen A fusion was carried out between $SP_2$ cells (non-secreting fusion line SP2/01-Ag14, ATCC Accession No. CRL 8006) and the mouse spleen from the above immunization protocol. A single cell suspension of the immunized spleen was prepared in 5 mL Dulbecco's Modified Eagle Medium (DMEM) (Gibco Laboratories, Grant Island, N.Y.), containing 15% fetal calf serum (FCS), using the frosted ends of two glass slides. The total number of cells was $2.4 \times 10^8$. $SP_2$ myeloma cells, $1.67 \times 10^8$ cells, in log phase growth were added. The cells were washed once with DMEM containing 15% FCS (Hyclone Defined FCS, Hyclone Laboratories Inc., Logan, Utah) and once with DMEM without FCS.

Polyethyleneglycol (PEG) (PEG 1450, J. T. Baker Inc. Phillipsburg, N.J.), 2 mL, was added to the pellet. After gently resuspending the cells, they were centrifuged for six minutes at 230×g and three minutes at 190×g. The supernatant was removed and the cells were resuspended in 5 mL of DMEM without FCS. This suspension was centrifuged for seven minutes at 230×g. The cells were resuspended in 240 mL DMEM with high glucose (DMEM with 4.5 g/L glucose, Gibco), containing $10^{-4}$M hypoxanthine (Sigma), 2 µg/mL azaserine (Sigma) and 20% FCS containing Pen strep (Gibco) and L-glutamine (Gibco). Twenty-four flat bottom 96-well tissue culture plates (Becton Dickinson Labware, Oxnard, Calif.) were previously filled with 150 µL/well of the above resuspension medium. The fusion suspension was added to the plates, 100 µL/well. The plates were incubated in a 7% $CO_2$ humidified incubator at 37° C.

Hybrids were detected on Day 5 and on Day 13, 150 µL of the culture supernatant was collected from each well having a growing hybrid. This fusion was plated out to give no more than 20% of the wells with growing hybrids. This allows for easier characterization of specific hybrids. The hybrids continued to grow in complete medium, the azaserine was discontinued after two weeks. As the hybrids were selected, they were expanded into flasks, then frozen in liquid Nitrogen. The supernatant collected from wells with growing hybrids were screened by the following ELISA method.

Black Immulon II microtiter plates (Dynatech) were coated with plaque antigen extract II (Section I-1), 0.1 µg of extracted protein in 100 µL PBS pH 8.5 per well. The plates were covered and incubated at 4° C. for 12 to 18 hours and then washed once with PBS containing 1% BSA (wash buffer). The plates were blocked with wash buffer for one hour at ambient temperature and then washed four times with buffer. The supernatants collected from wells with growing hybrids above were added to the antigen coated plates, 100 µL/well. The plates were incubated for two hours at ambient temperature, then washed four times with wash buffer. Peroxidase conjugated goat anti-mouse IgM and IgG, heavy and light chain specific (Tago Inc., Burlingame, Calif.) diluted in 20 mM Tris chloride, 150 mM sodium chloride pH 7.5 containing 5% BSA was added 100 µL/well, and the plates incubated for two hours at ambient temperature. The plates were washed four times with wash buffer and 100 µL of 4-methylumbelliferyl phosphate substrate solution (3M Diagnostics) were added to each well. The plates were read at intervals in a Fluorofast 96-well fluorometer (3M Diagnostics). Clone Z2D3 was found to be positive in this assay.

Using a Hyclone Sub-Isotyping Kit, the Z2D3 monoclonal antibody was identified as an IgM. Using an ELISA format similar to that outlined above with human complement factors as the coated antigen, the Z2D3 monoclonal antibody was found not to bind to human complement factors $Cl_q$, $C_3$ or $C_4$. Immunohistology using human atherosclerotic tissue sections (see section III) demonstrated that the Z2D3 monoclonal antibody binds specifically to the atherosclerotic lesion, and not to surrounding normal tissue.

II. Development Of Anti-Human Atherosclerotic Plaque Monoclonal Antibody, Z2D3/3E5

Hybridoma cell line Z2D3/3E5 (ATCC Accession No. HB10485) producing an IgG-class monoclonal antibody against the Z2D3 atherosclerotic antigen, was isolated as a result of sequential subcloning of the hybridoma cell line, Z2D3 (ATCC Accession No. HB9840). Z2D3 cells in DMEM medium, with 15 FCS, were plated in 96-well Falcon Tissue Culture plates (Becton Dickinson), 1000 cells/well, ten plates total. The cells were incubated in a 7% $CO_2$ humidified incubator at 37° C. At day 8, media samples were collected and tested for IgG using the following ELISA.

Black Immulon II microtiter plates (Dynatech) were coated overnight at 4° C. with 50 µL/well goat antimouse IgG, gamma chain specific (Zymed). The plates were washed four times with PBS containing 0.05% Tween-20 (Sigma) (wash buffer) and 50 µL of media from each well of the tissue culture plates above added to individual wells of the ELISA plates. The plates were incubated for two hours at ambient temperature. The plates were washed four times with wash buffer and 50 µL of a 1000-fold dilution of alkaline phosphatase conjugated goat anti-mouse IgG, gamma chain specific (Zymed) in wash buffer were added to each well. The plates were incubated for two hours at ambient temperature. The plates were washed four times with wash buffer and 100 µL of 4-methylumbelliferyl phosphate substrate solution (Sigma) were added. After one hour at ambient temperature, the plates were read using a Fluorofast 96-well fluorometer (3M Diagnostics)

The sensitivity of the assay enabled one positive cell in 1000 to be detected easily. Three positive wells were detected. Well 8G2, which produced the highest signal, was further enriched by plating as follows:

The cells in well 8G2 were resuspended in 100 mL of DMEM medium containing 9% FCS, and plated in five, 96-well plates at 200 µL/well. Supernatants from these wells were tested as above, eight days later. Seventy percent of the wells were positive for IgG. The well (1A12) with the highest signal for IgG was chosen for additional subcloning. Cells in this well were suspended by pipetting and 20 µL of the suspension was diluted into 100 mL of DMEM medium with 9% FCS. The suspension was plated 200 µL/well in five plates, yielding approximately 3 cells/well.

After eight days, the supernatants were tested for IgM and IgG using the ELISA protocol described above. To assay IgM, the plates were coated with goat anti-mouse IgM, µ chain specific (Tago), at 500 ng/well and alkaline phosphatase conjugated goat anti-mouse IgM, µ chain specific (Tago) was used as the conjugate. The three supernatants with the highest IgG signal were retested using serial dilutions to more accurately determine amounts of µ and γ chains. Well 7D10 had the highest γ and the lowest µ. This well (7D10) was then subcloned at 0.5 cells/well in six plates for the final derivation of a cloned line.

Single clones were identified visually and tested with IgM and IgG reagents. Several γ producing clones were chosen, of which 3E5 was further grown and studied. This clone was designated Z2D3/3E5. The IgG class was confirmed and subclass determined using a Sub-Isotyping Kit (Hyclone). Monoclonal antibody Z2D3/3E5 is an IgG1.

The specificities of monoclonal antibodies Z2D3 IgM and Z2D3/3E5 IgG are identical. By means of immunohistological staining (Section III) of sequential frozen tissue sections of human and rabbit atherosclerotic plaque, it was shown that these two antibodies exhibit identical localization in the lesions and give identical negative results in normal tissues. In addition both antibodies bind to antigens coated on microtiter plates in an ELISA (Section IV-2-(c) and IV-2-(d)) whereas non-specific antibodies of the same class do not bind under identical conditions.

III. Immunohistological Staining With The Z2D3 Monoclonal Antibody

Figure 1B:
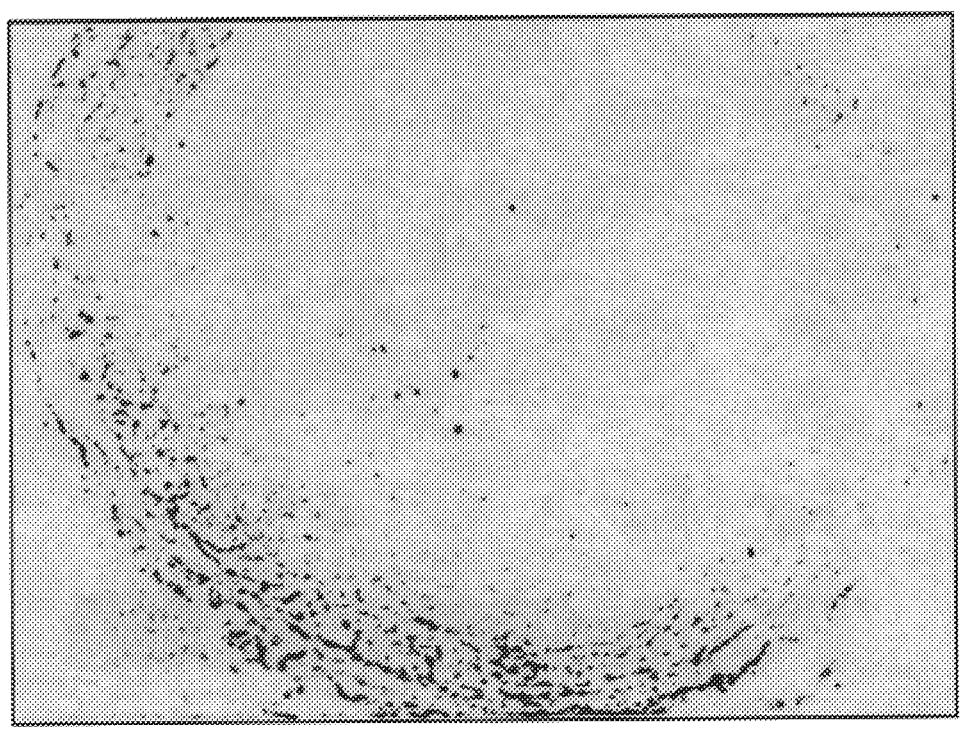
Figure 2A:
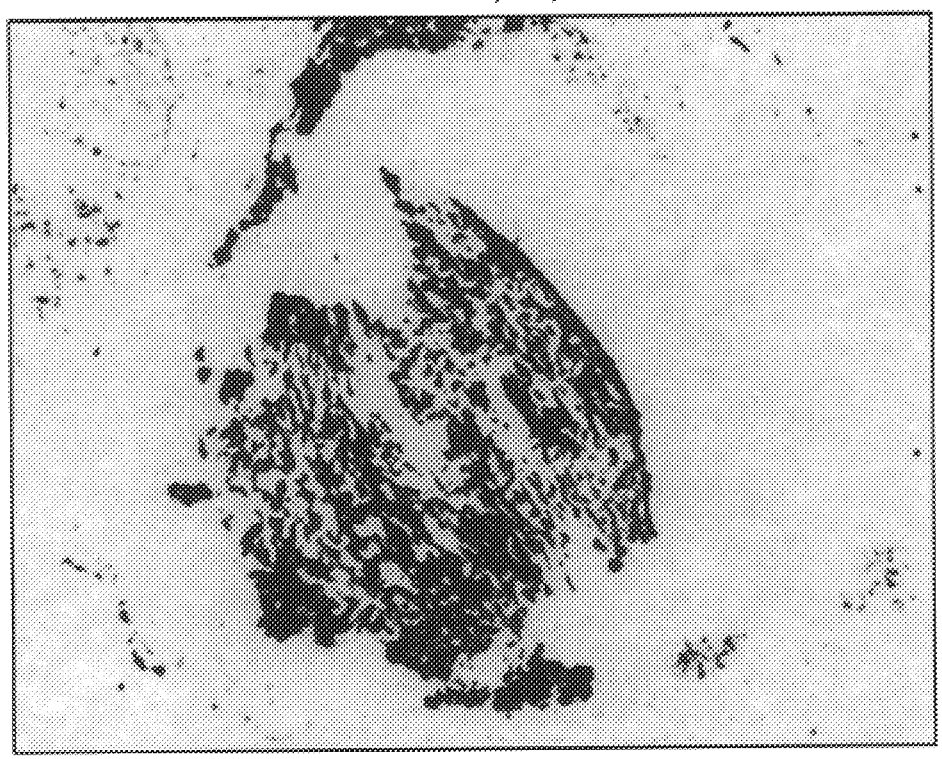
Figure 2B:
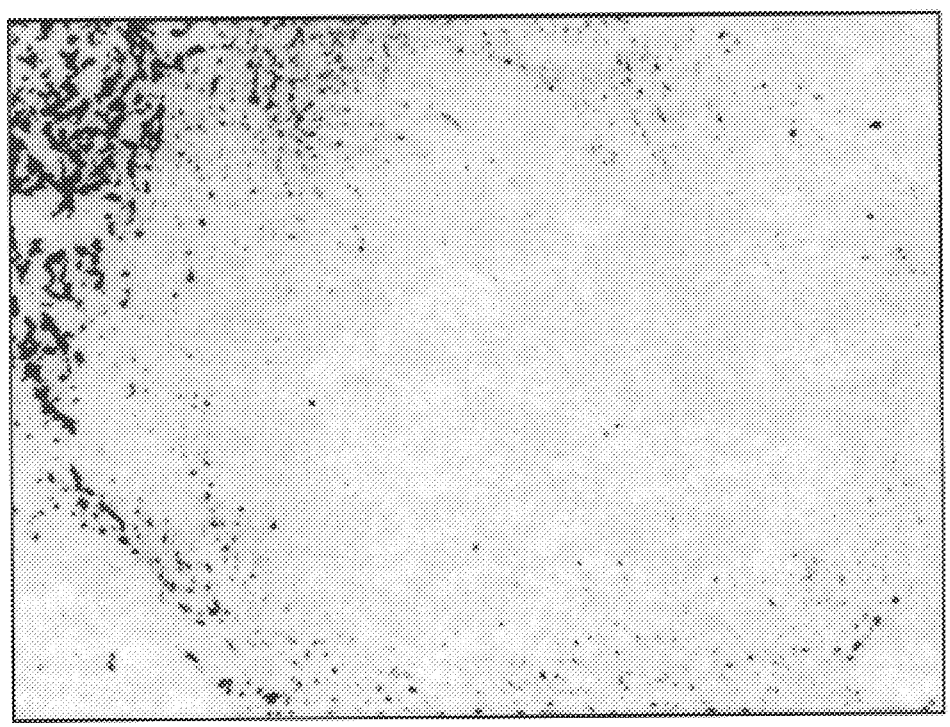
Figure 3A:
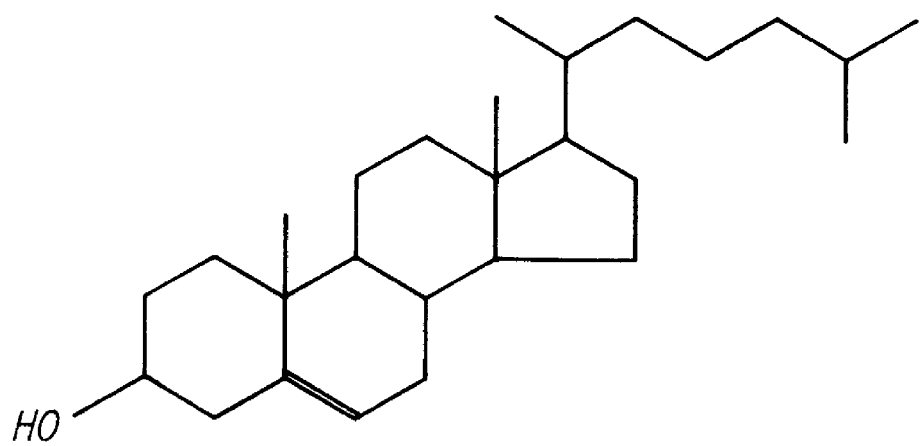
Figure 3B:
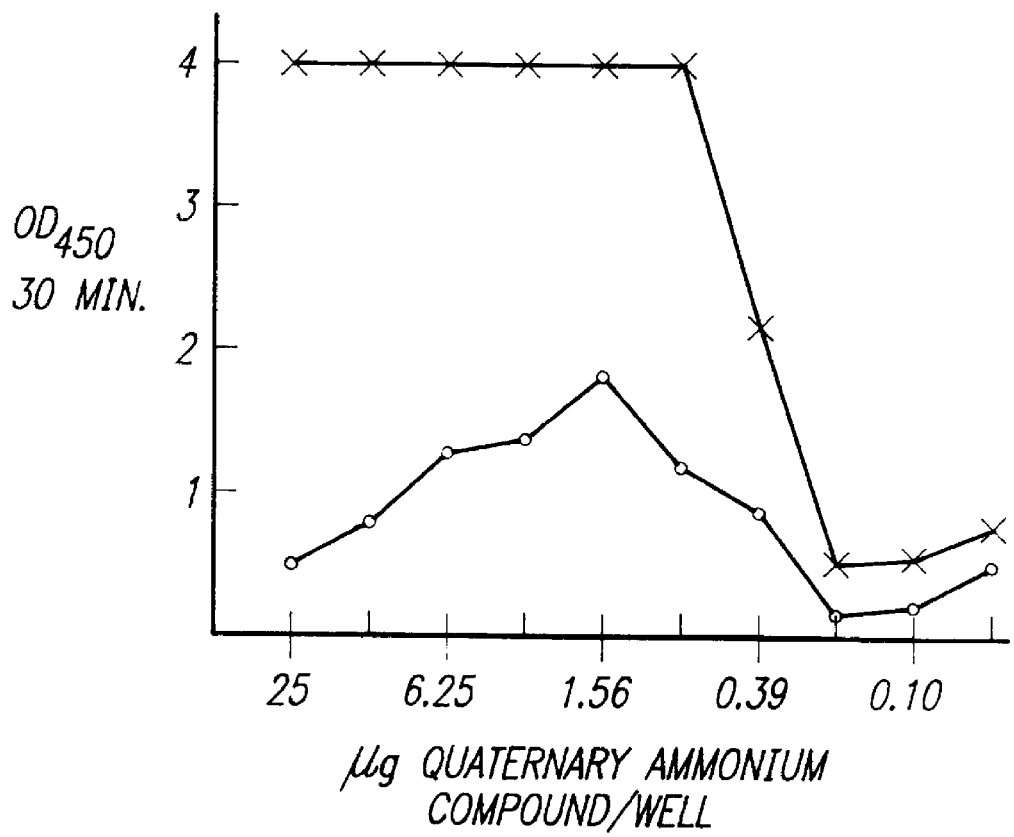
Figure 4A:
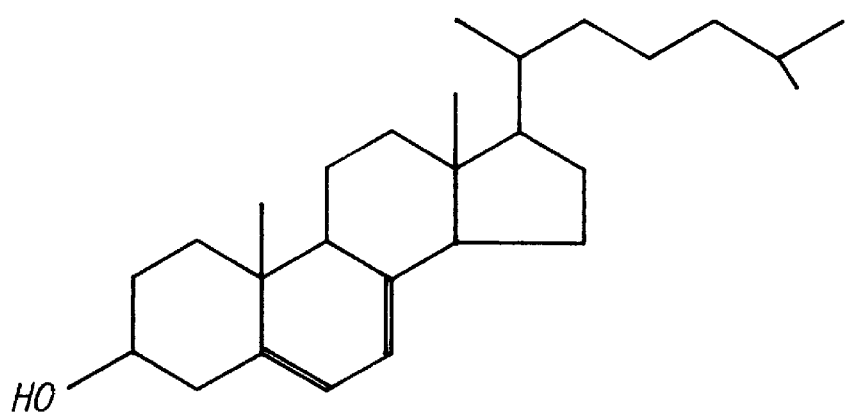
Figure 4B:
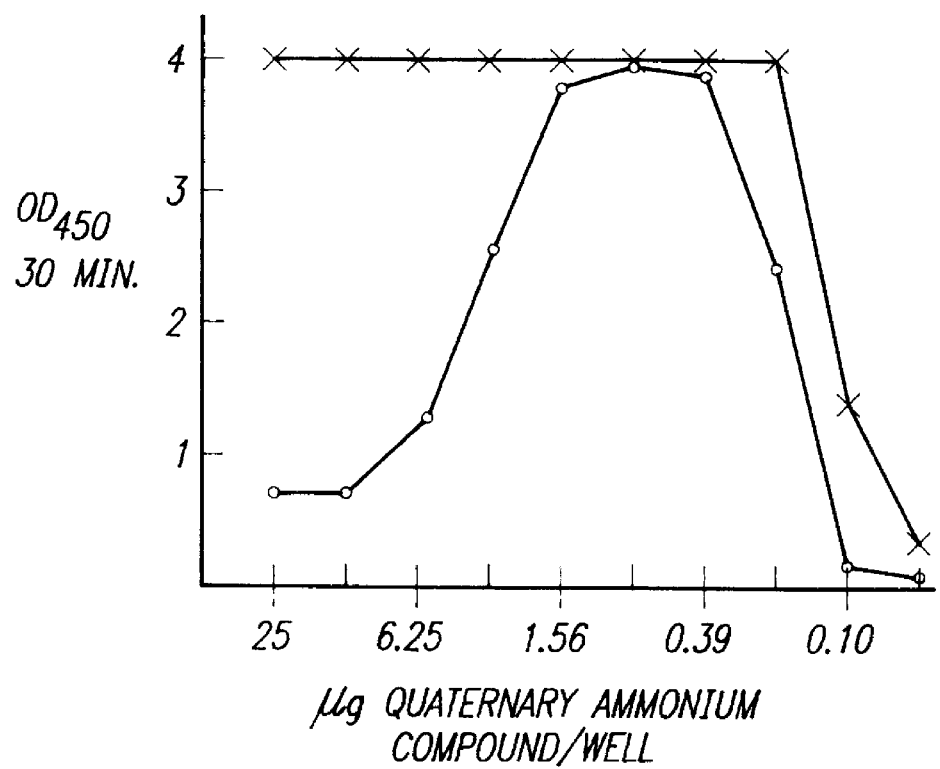
Figure 5A:
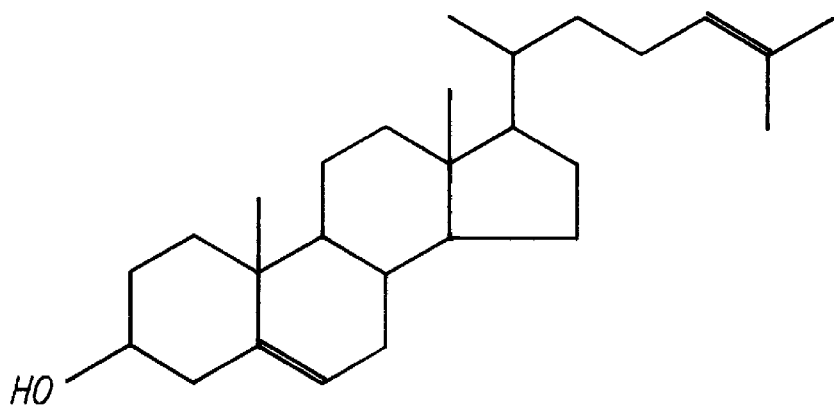
Figure 5B:
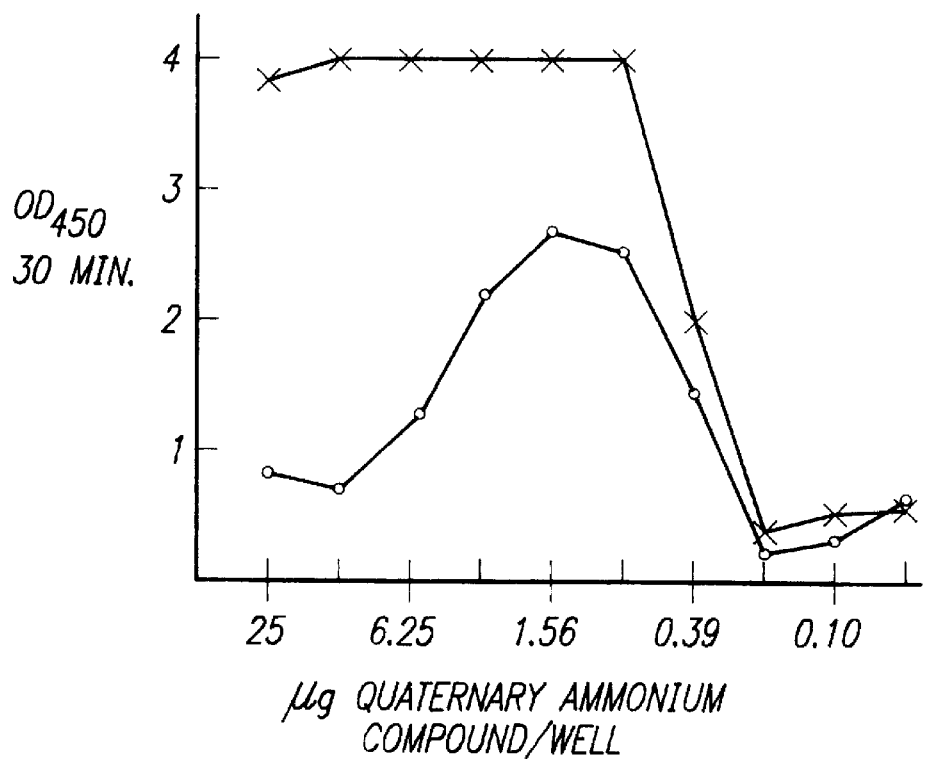
Figure 6A:
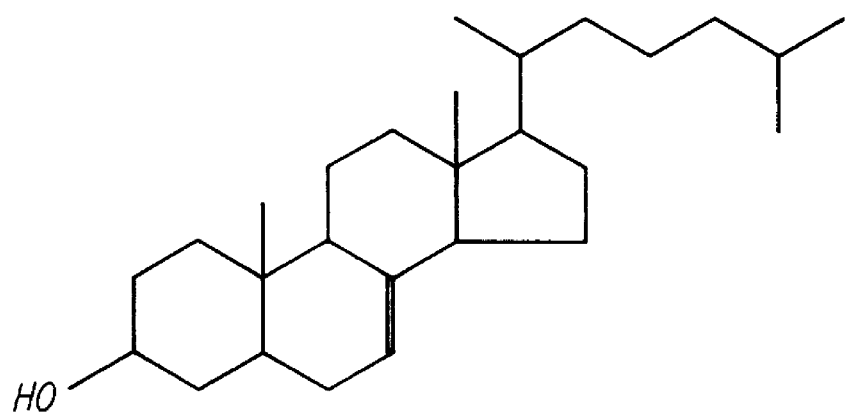
Figure 6B:
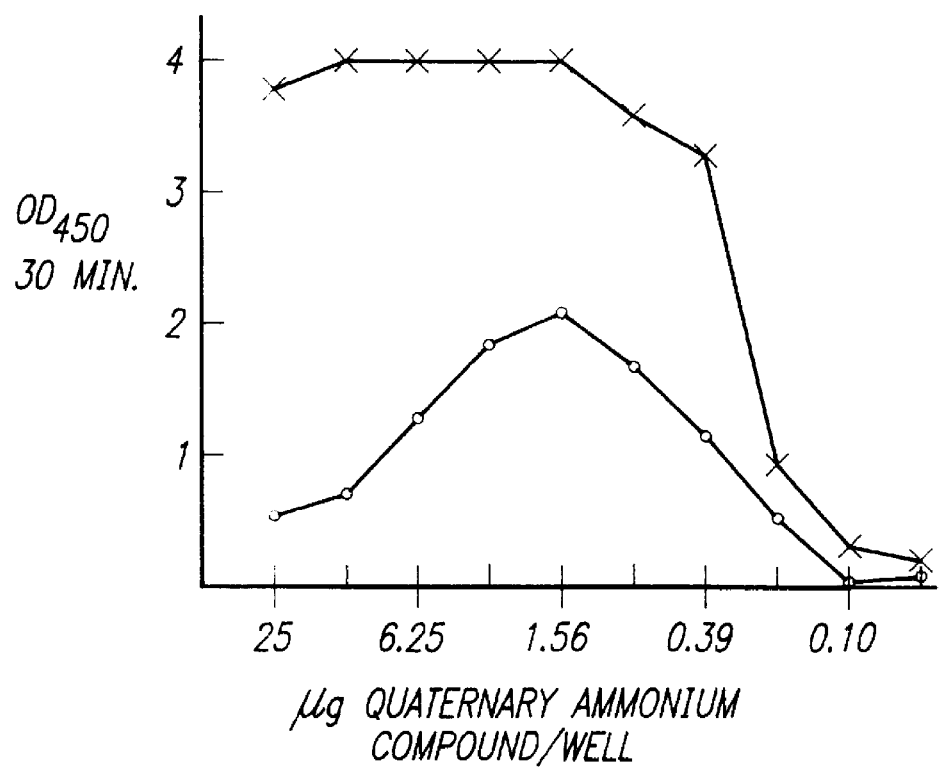
Figure 7A:
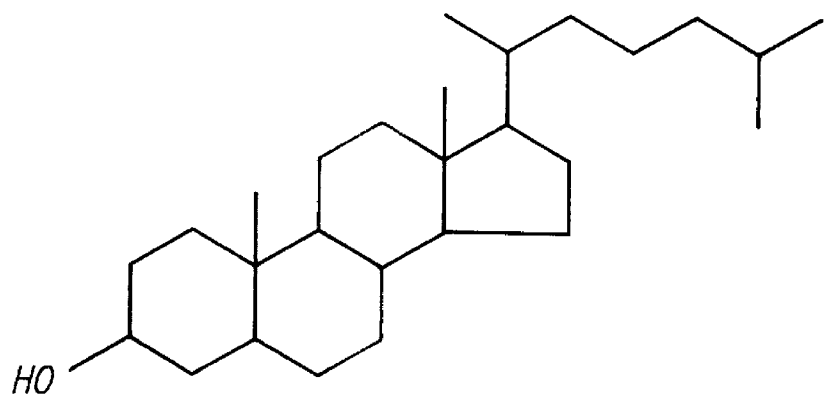
Figure 7B:
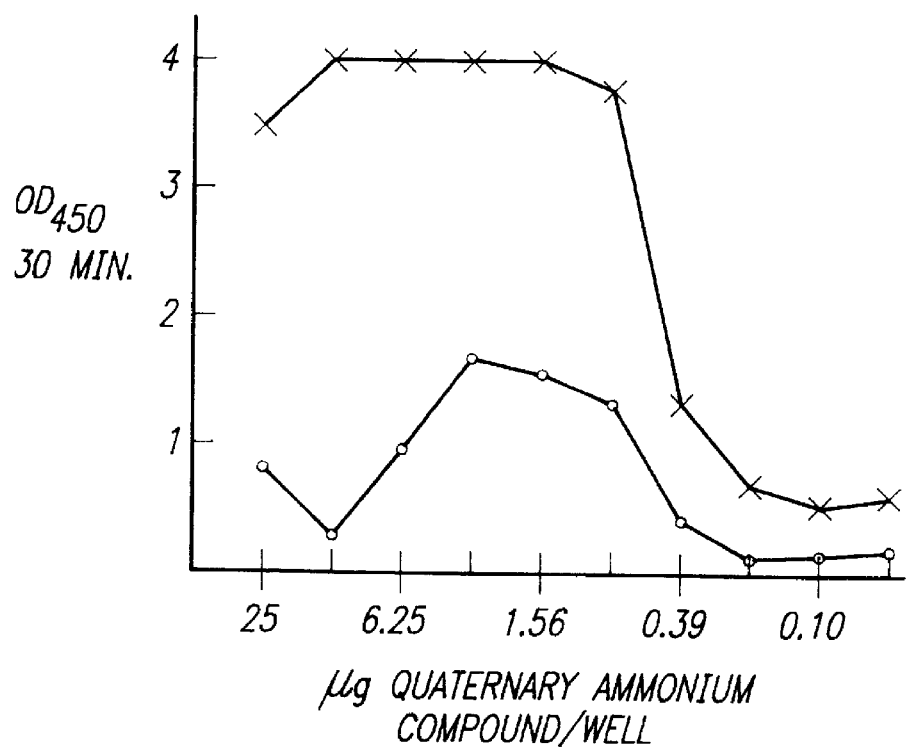
Figure 8A:
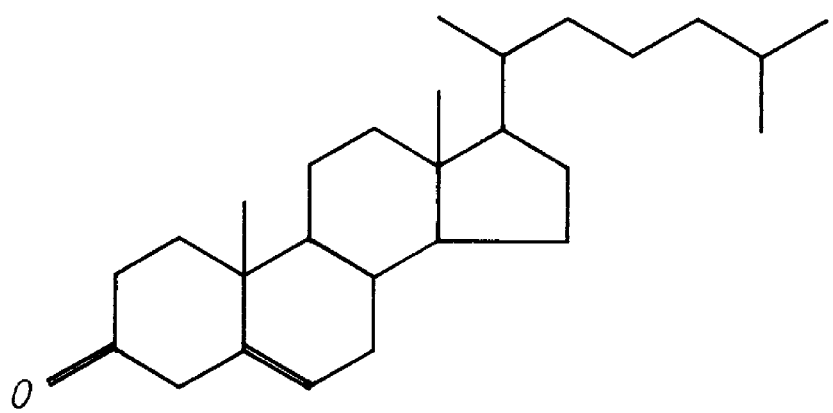
Figure 8B:
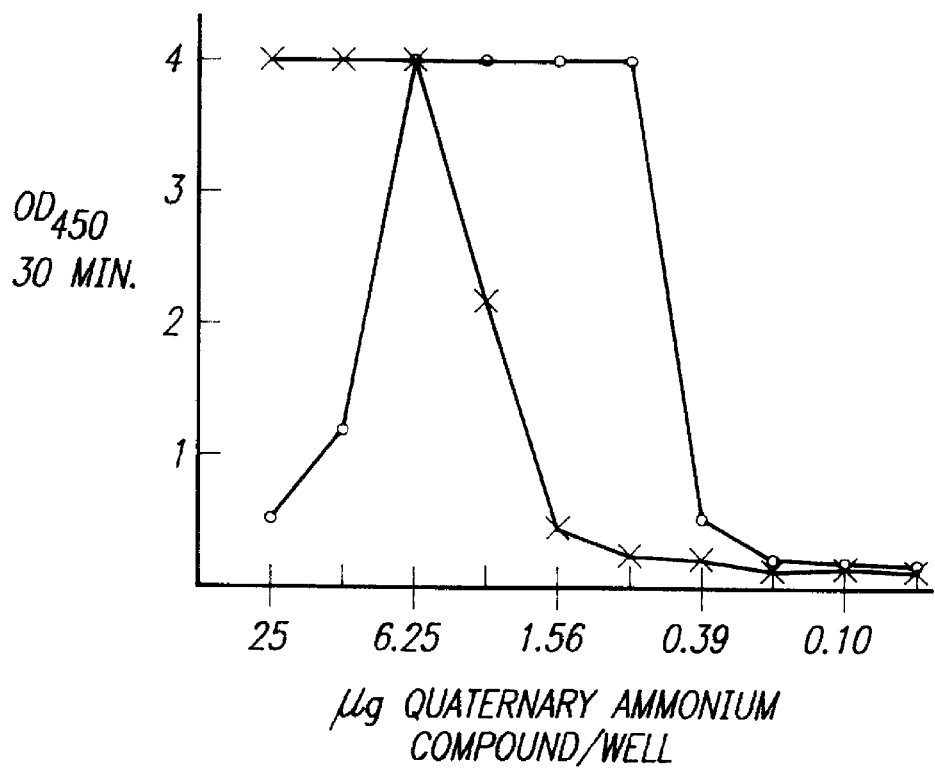
Figure 9A:
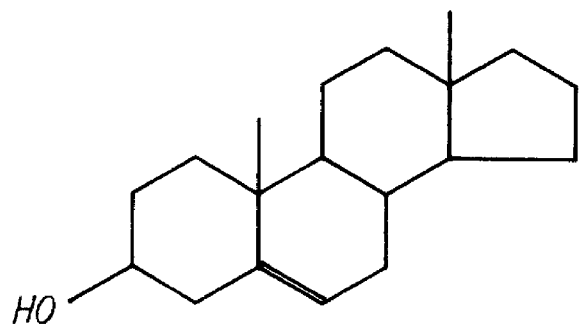
Figure 9B:
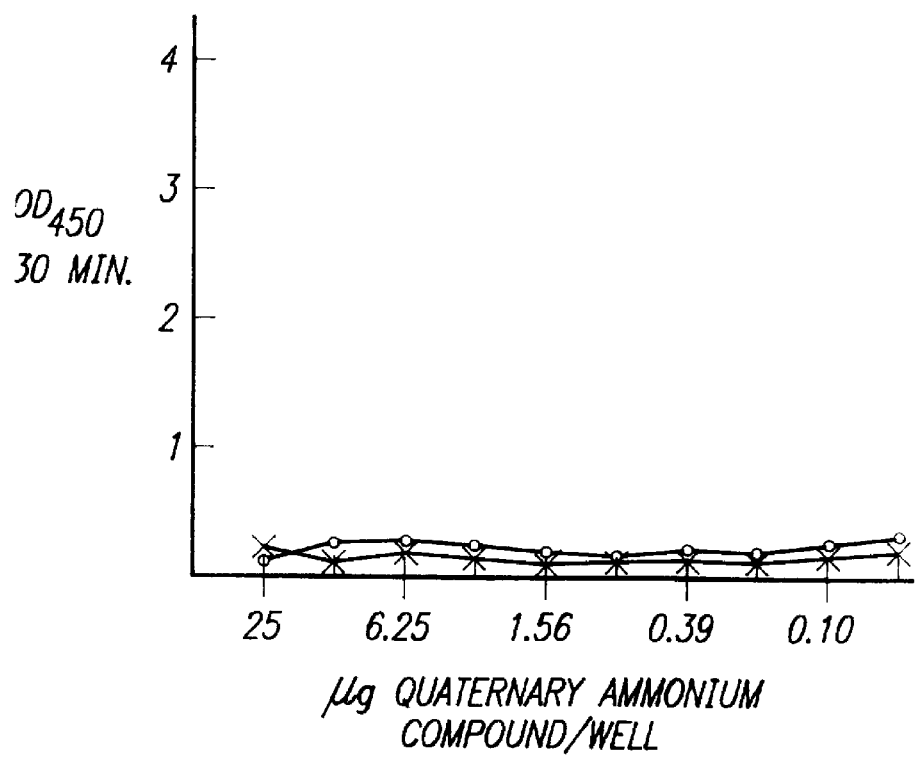
Figure 10A:
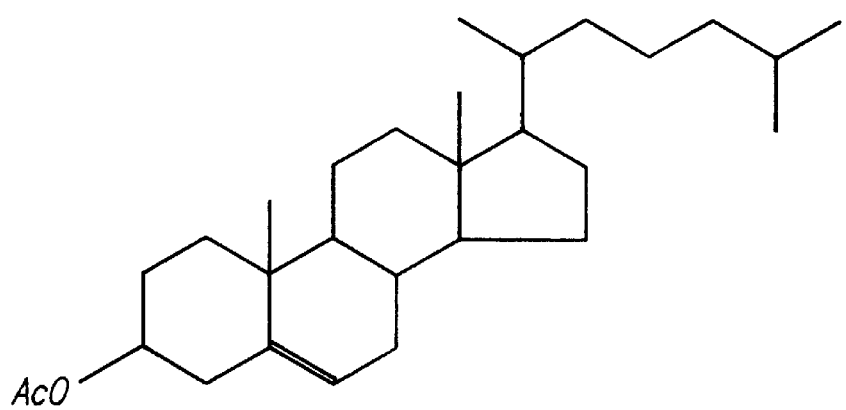
Figure 10B:
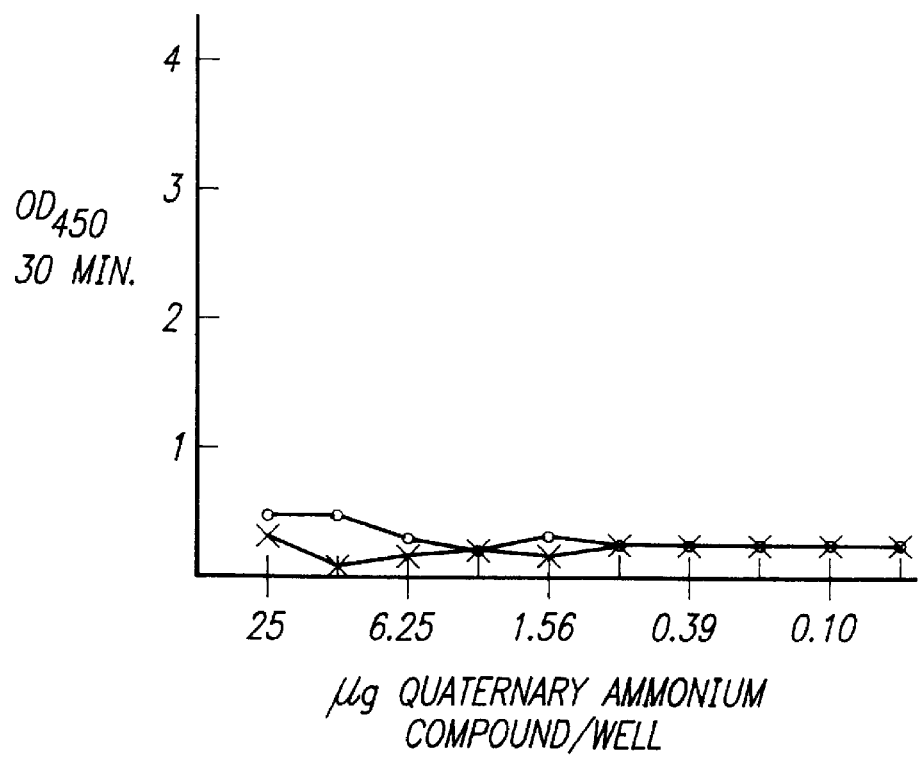
Figure 11A:
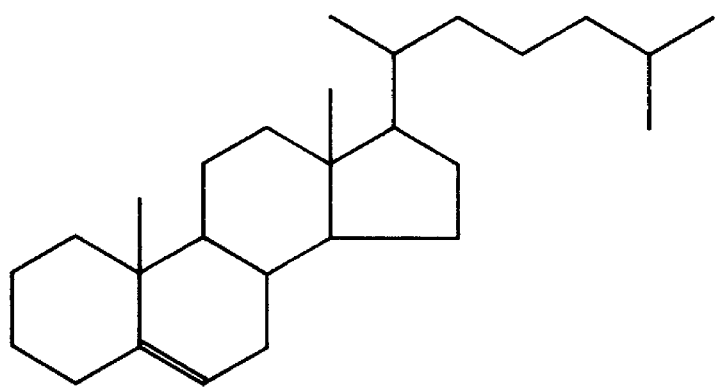
Figure 11B:
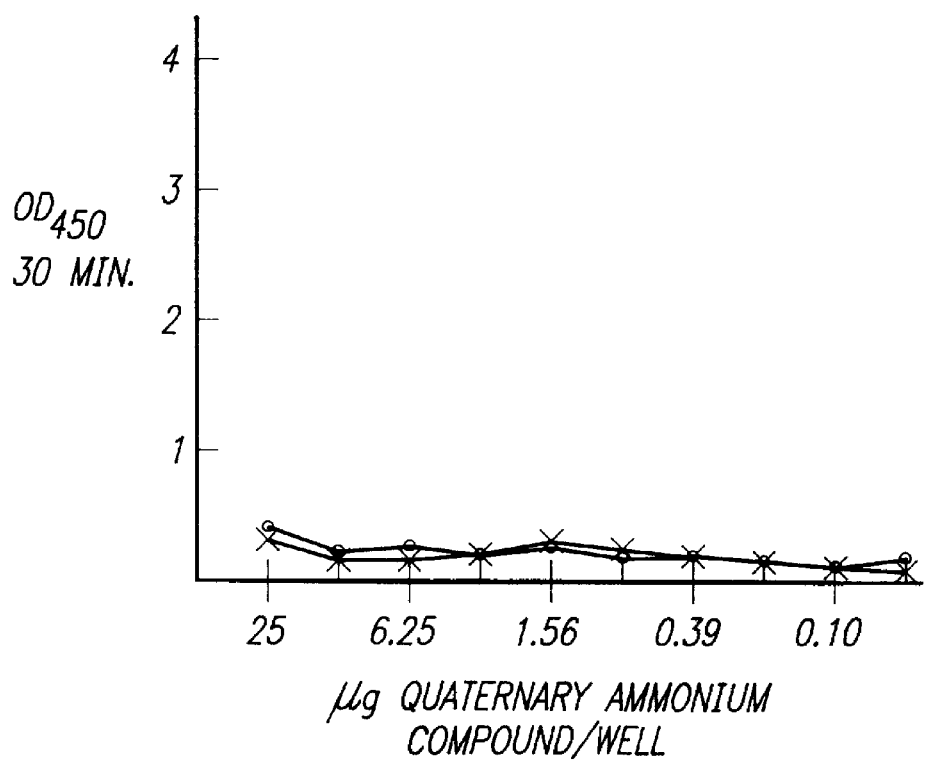
Figure 12A:
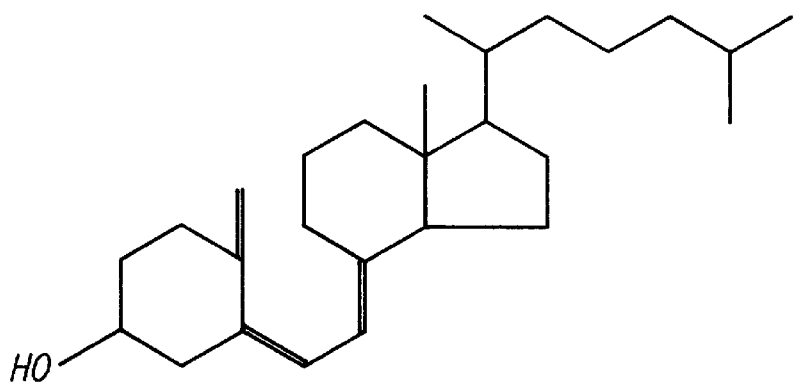
Figure 12B:
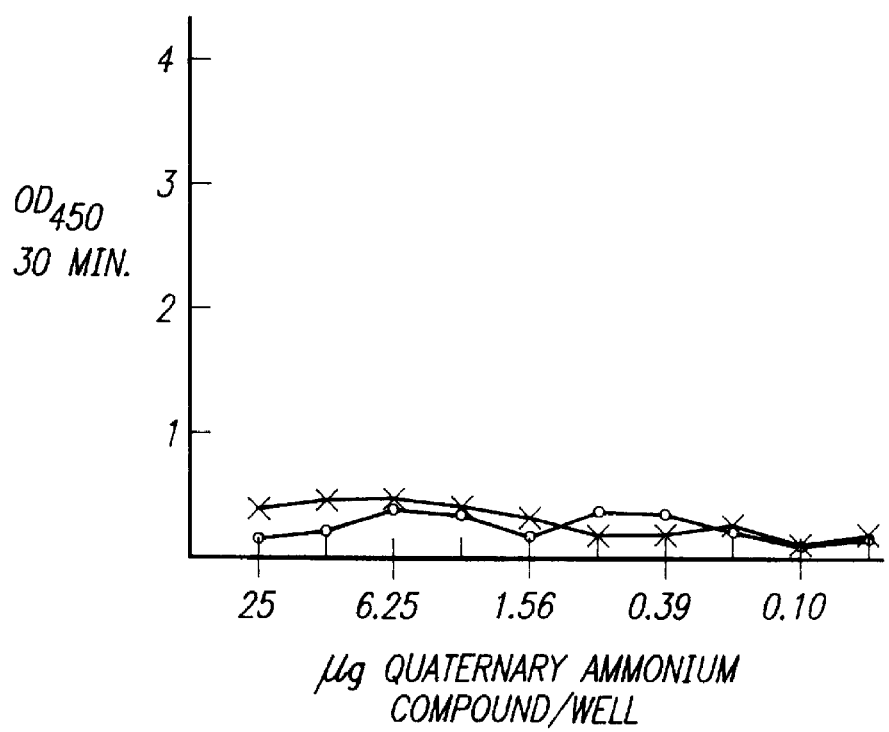

The binding of the Z2D3 monoclonal antibody to human atherosclerotic plaque sections was demonstrated by immunohistology. Unfixed frozen human atherosclerotic tissue sections, 5 μm thick, were mounted on glass slides. An appropriate dilution of the Z2D3 antibody, usually 10 to 100 μg/mL, in PBS containing 1% BSA was applied to the sections and incubated for an appropriate time at ambient temperature. The sections were washed with PBS/BSA and then processed with a Vectostain ABC Reagent Kit (Vector Laboratories, Burlingame, Calif.), an immunoperoxidase staining kit containing a biotinylated anti-mouse IgM conjugate, in accordance with the manufacturer's instructions. A precipitating peroxidase substrate, 3,3'-diaminobenzidine (Sigma) was used as instructed. The slides were washed with water and then counterstained with hematoxylin (Lerner Laboratories, Pittsburgh, Pa.). The Z2D3 monoclonal antibody gave extensive staining of the plaque matrix without staining the surrounding normal tissues, FIGS. 1 and 2.

The Z2D3 antibody was further screened on a variety of human tissues using 5 μm unfixed frozen tissue sections. The lesion areas of all diseased human coronary arteries and aortae tested were stained with the Z2D3 antibody. All normal tissues with the exception of spleen fibromyocytes and focal cell clusters of ovary and sebaceous glands failed to stain with this antibody (Table 1). The staining in ovary and sebaceous tissue was confined to the cytosol without extracellular manifestations. In contrast, the vast portion of staining within atherosclerotic plaque was extracellular, diffusely manifest throughout the connective tissue matrix in addition to staining the cytosol of the plaque smooth muscle cells. In fibrofatty lesions, areas of macrophage involvement stained less strongly than areas with only connective tissue or smooth muscle cell involvement.

In addition to human atherosclerotic lesions, the Z2D3 antibody also stained the atherosclerotic lesions of all animal models studied, including macaque monkey, New Zealand white rabbit and pig. In the case of the macaque monkey tissues, several phases of lesion growth were studied. In monkeys that had been maintained on a 2% cholesterol diet for a period exceeding one year the plaques stained strongly with the Z2D3 antibody. More interesting, however, was the observation that beneath the early fatty streaks of monkeys that had been maintained on the cholesterol diet for only months, the Z2D3 antibody stained the cytoplasm and immediate pericellular regions of the medial smooth muscle cells located immediately beneath the elastic lamina of those areas of the artery wall that were thus involved. This appeared within the time sequence corresponding to the migration of both macrophages and lymphocytes to this early lesion [Rapacz, J., et al., Science 234: 1573 (1986)]. Slightly later in time, the smooth muscle cells were seen to penetrate the elastic lamina and migrate into the fatty streak area.

IV. Characterization Of Human Atherosclerotic Plaque Antigen Recognized By Monoclonal Antibody Z2D3

As outlined in Section III, the Z2D3 monoclonal antibody binds to a specific antigen epitope present in atherosclerotic plaque. The chemical nature of this antigen has been partially determined.

IV-1. Modification Of The Immunohistological Staining Properties Of Monoclonal Antibody Z2D3 Antigen As A Result Of Various Pretreatments Of Atherosclerotic Tissue IV-1-(a) Treatment Of Tissue Sections With Organic Solvents All of the immunohistological results outlined above were obtained using unfixed frozen tissue sections. In immunohistology, tissue sections are usually fixed prior to performing the staining procedure. Commonly used fixing agents include methanol, ethanol and acetone (Hopwood, D., "Fixation and Fixatives" in *Theory and Practice of Histological Techniques*, Bancroft, J. D. and Stevens, A., Eds., 3rd Ed., 1990, Churchill Livingston, N.Y.). However, when atherosclerotic plaque sections are fixed with organic solvents, such as those above, prior to performing immunohistology with the Z2D3 monoclonal antibody, no staining of the lesion is observed.

This loss of staining due to treatment with solvents has been interpreted as an indication that the Z2D3 antigen, or a portion thereof, is soluble in organic solvents. That is, the antigen is, at least in part, a lipid.

IV-1-(b) Treatment Of Tissue Sections With Enzymes

Unfixed frozen tissue sections of human atherosclerotic lesions have been treated with solutions of various enzymes just prior to performing immunohistology with the Z2D3 monoclonal antibody. From the known specificity of the individual enzymes and their effect on the binding of the Z2D3 antibody to the antigen in the lesion, conclusions can be drawn about the chemical nature of the antigen.

Proteases. Tissue sections were incubated in buffered solutions of trypsin, collagenase or dispase under conditions suitable for the respective enzymes. After washing the section to remove the enzyme, histology with the Z2D3 monoclonal antibody was performed as described in Section III. Under conditions where the enzyme did not cause significant visible damage to the tissue section, no diminution of lesion staining was observed. These results are interpreted as indicating a lack of protease labile bonds in the antigen molecule(s). That is, the antigen does not appear to be a protein.

Cholesterol Oxidase. Cholesterol oxidase [EC 1.1.36] is a 59,000 MW enzyme which catalyzes the oxidation of cholesterol to 4-cholesten-3-one via the intermediate 5-cholesten-3-one. Cholesterol oxidase is most active with cholesterol, but will also oxidase several compounds with structures similar to cholesterol [Biochemica Information, Boehringer Manheim, Indianapolis, Ind.).

Human atherosclerotic tissue sections were incubated with a solution of cholesterol oxidase (Sigma), 2.8 mg/mL in 0.5M potassium phosphate pH 7.5, for two hours. After washing the sections to remove the enzyme, histology with the Z2D3 monoclonal antibody was performed as in Section III. Under these conditions, the staining of the lesion was almost completely eliminated.

In order to confirm that this result was due to the enzymatic activity of cholesterol oxidase and not to the mere presence of the enzyme, cholesterol oxidase was preincubated with mercury (II) chloride (Sigma), a potent inhibitor of cholesterol oxidase. The enzyme was dissolved at 2.8 mg/mL in 0.5M potassium phosphate buffer pH 7.5 containing 10 mM mercury (II) chloride. This enzyme solution, including the inhibitor, was then incubated on human atherosclerotic tissue sections for two hours. After washing the sections to remove the enzyme, histology was performed with the Z2D3 monoclonal antibody as in Section III. Under these conditions, significant staining of the lesion, about 90% of that of the nonenzymatically treated control occurred.

Taken together, the results above strongly indicate that the Z2D3 antigen or a portion thereof is susceptible to degradation by cholesterol oxidase. Which, in turn, can be interpreted as an indication that the Z2D3 antigen or a portion thereof is cholesterol or a steroid similar in structure to cholesterol which can be oxidized by cholesterol oxidase.

Acetylcholinesterase. Acetylcholinesterase [EC 3.1.1.7] is a 230,000 MW protein which catalyzes the hydrolysis of acetylcholine. It is fairly specific for choline esters, but will hydrolyze the acetic acid esters of some other alcohols [Biochemica Information, Boehringer Manheim, Indianapolis, Ind.]. The active site of acetylcholinesterase binds to the acetic acid portion of its substrate. Propionic acid esters are hydrolysed slowly if at all. The esters of higher acids are not hydrolysed by acetylcholinesterase [Soreq H., Gnatt, A., Loewenstein, Y., and Neville, L. F., Trends Biochem Sci., 17; 353–358, 1992].

Human atherosclerotic tissue sections were incubated with a solution of acetylcholinesterase (Sigma), 0.32 mg/mL in 50 mM 2-amino-2-hydroxymethyl-1,3-propanediol (Tris) chloride (U.S. Biochemical Corp., Cleveland, Ohio), pH 8.0, for two hours. After washing the sections to remove the enzyme, histology with the Z2D3 monoclonal antibody was performed as described in Section III. Under these conditions, the staining of the lesion was almost completely eliminated. The reduction in staining was uniform over the extent of the lesion.

In order to determine that these results were due to the enzymatic activity of the enzyme, acetylcholinesterase was preincubated in 5.7 $\mu$M PMSF (Sigma), a potent inhibitor of acetylcholinesterase, in Tris buffer. This enzyme solution including the inhibitor was then incubated on human atherosclerotic tissue sections for two hours. After washing the sections to remove the enzyme, histology was performed with the Z2D3 monoclonal antibody. Under these conditions, nearly complete recovery of the staining in advanced lesion areas was observed.

These results strongly suggest that the Z2D3 antigen in atherosclerotic plaque contains an essential ester, possibly a choline ester, and that hydrolysis of this ester significantly reduces antigen recognition by the Z2D3 monoclonal antibody.

Butyryl Cholinesterase. Also known as serum cholinesterase, butyryl cholinesterase [EC 3.1.1.8] is a tetrameric glycoprotein with a molecular weight of approximately 110,000. Butyryl cholinesterase hydrolyzes butyrylcholine more rapidly than it does acetylcholine. However, butyryl cholinesterase is not specific for choline esters as it hydrolyses a variety of different esters [Merck Index, 11th Ed., entry 2211, Merck and Co., Rahway, N.J.].

Human atherosclerotic tissue sections were incubated with a solution of butyryl cholinesterase 0.6 mg/mL in 50 mM Tris chloride pH 8.0, for two hours. After washing the section to remove the enzyme, normal histology with the Z2D3 monoclonal antibody was performed. Under these conditions, the staining of the lesion was not affected by the enzyme treatment.

These results indicate that the essential ester, demonstrated by the effect of acetylcholinesterase on human atherosclerotic lesions, is not hydrolysed by butyryl cholinesterase. Given the known substrate specificity of the two cholinesterases [Soreq, H., Gnatt, A., Loewenstein, Y., and Neville, L. F., Trends Biochem Sci. 17: 353–358, 1992], the essential ester would appear to be an ester of acetic acid.

Porcine Esterase. Porcine esterase is a 165,000 molecular weight protein isolated from pork liver which hydrolyses a wide variety of esters.

Human atherosclerotic tissue sections were incubated with esterase solutions in the concentration range of 10–100 $\mu$g/mL in 50 mM Tris chloride pH 7.5. After washing the sections to remove the enzyme, normal histology with the Z2D3 monoclonal antibody was performed. Under these conditions the binding of the Z2D3 antibody was reduced in proportion to the concentration of esterase used. At high concentrations of esterase, the binding of the antibody was almost completely eliminated.

These results confirm the presence of an essential ester in the Z2D3 antigen found in human atherosclerotic plaque. The broad substrate specificity of porcine esterase does not permit any further definition of the exact chemical nature of this ester.

Phospholipases. Phospholipases are a group of enzymes which hydrolyse specific bonds of phosphoglycerides. Phosphoglycerides are complex lipids which characteristically are major components of cell membranes. Only very small amounts of phosphoglycerides occur elsewhere in cells. Human atherosclerotic tissue sections have been treated with a variety of phospholipases to determine the enzymatic effects, if any, upon the binding of the Z2D3 monoclonal antibody.

Phospholipase $A_2$. Phospholipase $A_2$ [EC 3.1.1.4] specifically hydrolyses the fatty acid from position 2 of phosphoglycerides. This enzyme is monomeric with a molecular weight of about 14,500 [Biochemica Information, Boehringer].

Phospholipase $A_2$ from Crotalus atrox (Sigma) was dissolved in 50 mM Tris chloride pH 8.9 as directed by the supplier. Human atherosclerotic tissue sections were incubated with solutions of phospholipase $A_2$ at concentrations in the range of 10–100 $\mu$g/mL for two hours. After washing the sections to remove the enzyme, normal histology with the Z2D3 monoclonal antibody was performed. Under these conditions no diminution of the binding of the Z2D3 monoclonal antibody was observed.

Phospholipase B. Phospholipase B [EC 3.1.1.5] is a mixture of phospholipases $A_1$ and $A_2$ which hydrolyses the fatty acid esters from positions 1 and 2 of phosphoglycerides.

Phospholipase B from Vibrio species (Sigma) was dissolved in 50 mM Tris chloride pH 8.0 as directed by the supplier. Human atherosclerotic tissue sections were incubated with solutions of phospholipase B at concentrations in the range of 4–30 $\mu$g/mL for two hours. After washing the sections to remove the enzyme, normal histology with the Z2D3 monoclonal antibody was performed. Under these conditions no diminution of the binding of the Z2D3 monoclonal antibody was observed.

Phospholipase C. Phospholipase C [EC 3.1.4.3] specifically hydrolyses the bond between phosphoric acid and glycerol in phosphoglycerides. This enzyme is monomeric metalloenzyme with a molecular weight of about 22,500. Phospholipase C is relatively specific for phosphatidylcholine, other phosphoglycerides are hydrolysed at much slower rates [Biochemica Information, Boehringer].

Phospholipase C from C. perfringens (Sigma) was dissolved in 50 mM Tris chloride pH 7.3 as directed by the supplier. Human atherosclerotic tissue sections were incubated with solutions of phospholipase C at concentrations in the range of 10–80 $\mu$g/mL for two hours. After washing the sections to remove the enzyme, normal histology with the Z2D3 monoclonal antibody was performed. Under these conditions the binding of the Z2D3 monoclonal antibody to the atherosclerotic antigen was significantly reduced.

Phospholipase D. Phospholipase D [EC 3.1.4.4] specifically hydrolyses the bond between the polar head group and the phosphoric acid of phosphoglycerides. Two forms of this enzyme were used below, cabbage leaf phospholipase D has a molecular weight of about 112,500 while the Streptomyces chromofuscus enzyme has a molecular weight in the range of 50,000–57,000 [Biochemica Information, Boehringer].

Phospholipase D from cabbage leaf (Sigma) was dissolved in 50 mM Tris chloride pH 5.6 as directed by the supplier. Phospholipase D from Streptomyces chromofuscus (Sigma) was dissolved in 50 mM Tris pH 8.0 also as directed by the supplier. These enzymes were incubated separately on frozen human atherosclerotic tissue sections in the concentration range of 25–1000 µg/mL for two hours. After washing the sections to remove the enzyme, normal histology with the Z2D3 monoclonal antibody was performed. Under these conditions no diminution of the binding of the Z2D3 monoclonal antibody was observed.

Sphingomyelinase. Sphingomyelinase [EC 3.1.4.12] catalyzes the hydrolysis of sphingomyelin to phosphorylcholine and ceramide. Three forms of this enzyme, all monomers, were used below, Staphylococcus aureus sphingomyelinase, with a molecular weight of about 33,000, Streptomyces sp. sphingomyelinase, with a molecular weight of about 36,000, and Bacillus cereus sphingomyelinase with a molecular weight of about 23,000 [Sigma Technical Service].

The sphingomyelinases (all from Sigma) were dissolved individually in 50 mM Tris pH 7.4 as directed by the supplier. These enzymes were incubated separately on frozen human atherosclerotic tissue sections to remove the enzyme, normal histology with the Z2D3 monoclonal antibody was performed. Under these conditions no diminution of the binding of the Z2D3 monoclonal antibody was observed.

IV-1-(c) Summary Of Results With Enzymatic Treatment Of Atherosclerotic Plaque Lesions Prior To Immunohistological Staining With The Z2D3 Monoclonal Antibody The lack of any diminution of staining in immunohistology sections treated with proteases indicates that the naturally occurring Z2D3 antigen is not a protein. The efficacy of cholesterol oxidase, acetylcholinesterase, porcine esterase, and Phospholipase C in reducing the staining of atherosclerotic lesions with the Z2D3 antibody provides strong evidence that the naturally occurring Z2D3 antigen is comprised of several essential components. The first of these essential components is cholesterol or a steroid of similar structure which can be oxidized by cholesterol oxidase. A second of these essential components in the naturally occurring antigen is a phosphatidylcholine or another molecule whose chemical structure is subject to modification by the enzymatic action of phospholipase C. A third of these essential components is an ester whose hydrolysis is catalyzed by the actions of acetylcholinesterase or porcine esterase. At present, it is unknown whether these essential components of the naturally occurring antigen are found as portions of one or more separate molecules in atherosclerotic plaque. It is clear, however, that the naturally occurring antigen is comprised of a combination of a steroid, whose structure permits oxidation by cholesterol oxidase, and a quaternary ammonium salt, probably a salt of choline, either as an ester or as a polar head of a phosphoglyceride.

Further information regarding the structure of the Z2D3 antigen has been obtained using an ELISA assay system and a surrogate, that is, model, antigen, comprised of a steroid and a quaternary ammonium salt, section IV-2. Finally, monoclonal antibodies with specificities identical to that of the original murine Z2D3 monoclonal IgM have been generated using the surrogate antigen as an immunogen, section VI.

IV-2. Characterization Of The Atherosclerotic Antigenic Epitope Recognized Z2D3 Monoclonal Antibodies Using Enzyme-Linked Immunosorbent Assay System With Model Compounds IV-2-(a) Antibody-Antigen Interaction The binding of an antibody to its antigen is a highly specific reaction. This binding is also very tight, with binding constants in the range of $10^{-9}$ to $10^{-12}$ in many cases. Yet the binding of an antibody to the antigen against which it is directed occurs without the formation of any covalent chemical bonds. Only such attractive forces as charge interactions, hydrophobic interactions, or hydrogen bonds are involved. These forces are only efficacious over very short distances. The steric or structural fit of the antigen into the antibody binding site is therefore extremely important to the binding reaction. That is, the antigen must fit precisely into the antibody binding site so that the various portions of both molecules involved in the binding reaction are brought close enough together for binding to occur. The antigen must fit into the antibody binding site as a key fits into its lock. The exquisite specificity of antibody-antigen binding is therefore a consequence of this fit. Even a slight modification of the chemical structure of an antigen can greatly reduce or even completely eliminate antibody binding. For an extensive discussion of the structural aspects of antibody-antigen interaction, see Pressman, D., and Grossburg, A. L. ["The Structural Basis of Antibody Specificity", W. A. Benjamin, N.Y.]. The specificity of antibody-antigen binding can be exploited to elucidate precise structural information about the chemical nature of an antigen.

IV-2-(b) Surrogate Antigens For The Z2D3 Monoclonal Antibodies

The Z2D3 monoclonal antibodies do not bind to is atherosclerotic plaque sections which have been treated with acetone or alcohol [Section IV-1-(a)]. This is an indication that the antigen or a portion thereof is a lipid molecule, for example, a sterol. Immunohistology of atherosclerotic plaque sections which were treated with various enzymes [Section IV-1-(b)], in particular with cholesterol oxidase, acetylcholinesterase, and phospholipase C, indicate that the antigen is, at least in part, comprised of cholesterol or a steroid of similar structure and a quaternary ammonium salt, which is probably a salt of choline, either as an ester or as a polar head of a phosphoglyceride. Indeed, as will be explained further below, cholesterol and palmitoyl choline, a choline ester, when dried onto a microtiter wellplate, form a model or surrogate antigen to which the Z2D3 monoclonal antibodies, both the mouse IgM and the chimeric mouse-human IgG and the F(ab')$_2$ fragment thereof, specifically bind. This binding is readily demonstrated by means of an enzyme-linked immunosorbent assay (ELISA). By varying the chemical nature of the components of the surrogate antigen, conclusions can be drawn regarding the chemical structural requirements for Z2D3 monoclonal antibody binding. Because of the extreme structural specificity of the antibody binding reaction, conclusions drawn regarding the chemical structure of a surrogate antigen must also apply to the chemical structure of the Z2D3 antigen formed in vivo in atherosclerotic lesions.

IV-2-(c) Enzyme-linked Immunosorbent Assay System For Characterizing The Z2D3 Monoclonal Antibody Antigen Epitope ELISA's can be developed in a variety of different configurations [Voller, A., et al., "The Enzyme-Linked Immunosorbent Assay (ELISA)", Vols. 1 and 2, MicroSystems, Guernsey, U.K.]. In the ELISA used to study the Z2D3 antigen epitope, the chemical compound or compounds of choice are immobilized on polystyrene Immulon 2 microtiter plates (Dynatech, Chantilley, Va.). The remainder of the assay is a non-competitive antibody capture ELISA format. The primary antibody is either the mouse monoclonal Z2D3 IgM or the chimeric mouse-human Z2D3 IgG. The secondary antibody is a peroxidase conjugated antibody appropriate for binding to the primary antibody. A calorimetric peroxidase substrate is used in the final step.

Color development in an ELISA indicates the presence of the conjugated secondary antibody which can only be present if it is bound to the primary antibody. The primary antibody can only be present if it is bound to one or a combination of the compounds originally coated in the well. Given the high degree of specificity of the antibody-antigen binding reaction (section IV-2-(a)], the primary Z2D3 monoclonal antibody can bind to the chemicals in the well only if the coated chemicals present a structure which the primary antibody "recognizes" as being very similar or possibly identical in structure to the human atherosclerotic plaque antigen with which the Z2D3 monoclonal antibody was created. Thus, color in an ELISA well indicates that the compounds coated in that well function as a model or surrogate antigen for the Z2D3 monoclonal antibody.

Conversely, a lack of color development in an ELISA will indicate that the compounds coated in the well do not present a structure to which the primary Z2D3 monoclonal antibody can bind. Therefore, such compounds or combination of compounds do not function as surrogate Z2D3 antigens.

By varying the chemical nature of the compounds coated on ELISA plates, it can be determined which chemical structures are required for binding to the Z2D3 monoclonal antibody. Such chemical structures are extremely likely to be found in the Z2D3 atherosclerotic plaque antigen in vivo. Also, it can be determined which chemical structures prevent binding of the Z2D3 antibody. Such structures are extremely unlikely to be found in the Z2D3 antigen in vivo.

In addition, by varying the amounts or the ratio of the compounds coated on the ELISA plates, the relative strengths of the binding of the Z2D3 monoclonal antibody to the various surrogate antigens can be determined. Strong bonding is an indication of significant similarity of the surrogate antigen to the atherosclerotic plaque antigen.

IV-2-(d) ELISA Reagents And Procedure

All ELISA wash steps were performed with casein wash buffer (CWB) prepared as follows: 13 mM Tris-chloride (U.S. Biochemical Corp.), 154 mM sodium chloride (Sigma) and 0.5 mM Thimerosal (Sodium ethylmercurithiosalicylate) (Sigma) were dissolved in purified water and the pH of the solution adjusted to 7.6 with reagent grade hydrochloric acid. Bovine casein (Sigma) 2 g/L or 0.2%, was dissolved in the Tris buffer by gentle heating to 38°–40° C. After cooling slowly to ambient temperature, the pH was again adjusted to 7.6 with either reagent grade hydrochloric acid or reagent grade sodium hydroxide. After filtering through a medium grade fluted paper filter (Fisher Scientific, Pittsburgh, Pa.) the buffer is ready to use. CWB can also be prepared at four times the concentration given, and the concentrate be stored at 4° C. for up to six weeks.

The compound or compounds to be assayed were dissolved in absolute ethanol (Gold Shield Chemical Co., Hayward, Calif.) at the desired concentration [see section IV-2-(e)]. Aliquots of these solutions were applied to microtiter plate wells and the solvent removed by evaporation in a stream of air. Non-specific binding sites on the wells were blocked by incubating the plates in CWB for one hour at ambient temperature.

The Z2D3 monoclonal antibody was diluted in CWB to the desired concentration, generally in the range of 1 to 10 $\mu$g/mL. All of the results shown in FIGS. 3–12, FIGS. 14 and 15, as well as in Tables 2 and 3, were obtained with an antibody concentration of 5 $\mu$g/mL in CWB. The antibody solution was added to the blocked microtiter plate wells, 100 $\mu$L per well and the plates covered with Parafilm® (American National Can, Greenwich, Conn.). The covered plates were incubated at 37° C. for one hour.

Suitable conjugated secondary antibodies from a variety of species are available from several commercial suppliers. All of the ELISA results discussed in this application were obtained with the following. For ELISA's using the mouse monoclonal Z2D3 IgM as the primary antibody, the secondary antibody was horseradish peroxidase conjugated $F(ab')_2$ fragment of rabbit anti-mouse IgM obtained from Zymed Laboratories, Inc., So. San Francisco, Calif. This conjugate was diluted 500 fold in CWB prior to use. For ELISA's using the mouse-human chimeric monoclonal Z2D3 IgG as the primary antibody, the secondary antibody was horseradish peroxidase conjugated goat anti-human IgG, heavy and light chain specific, obtained from Lampire Biological Laboratories, Pipersville, Pa. This conjugate was diluted 1000 fold in CWB prior to use. Conjugate performance was very consistent from these two suppliers. However, any given lot of conjugate may require a dilution adjustment for optimal performance. Such adjustments are obvious to one skilled in the art of ELISA.

The primary antibody solution was removed from the wells and the wells washed four times with CWB. The appropriate conjugate at a suitable dilution in CWB was added to the wells, 100 $\mu$L per well. The plates were covered with Parafilm and incubated at 37° C. for one hour.

All ELISA results in this application were obtained with the tetramethylbenzidine peroxidase substrate system produced by Kirkegaard and Perry Laboratories, Inc. Gaithersburg, Md., mixed according to the suppliers instructions.

The secondary antibody solution was removed from the wells, and the wells washed five times with CWB. The substrate was added, 100 $\mu$L per well, and the plates incubated at ambient temperature. Color development was monitored at 650 nm with a Vmax® microtiter plate reader (Molecular Devices, Palo Alto, Calif.). After 30 minutes, color development was stopped by the addition of 50 $\mu$L 1M hydrochloric acid and the plate read at 450 nm. Because of the greater range of sensitivity, the results obtained at 450 nm are used throughout this application.

IV-2-(e) Chemicals Used As The Surrogate Antigen In The ELISA Assay System

The binding of the Z2D3 monoclonal antibody, both the mouse IgM and the chimeric mouse-human IgG, to a wide variety of combinations of chemical compounds were examined by the ELISA method outlined in section IV-2-(c). These combinations include, but are not limited to, the various combinations discussed in this application.

Steroids, the highest grade available, were purchased from one of the following: Sigma Chemical Co., St. Louis, Mo.; Research Plus, Inc., Bayonne, N.J.; or Steraloids, Inc., Wilton, N.H. Unless otherwise directed by the supplier, steroids were stored desiccated over phosphorous pentoxide, (Aldrich Chemical Co., Milwaukee, Wis.) at −20° C. Unless otherwise stated, all steroids were dissolved in absolute ethanol at a concentration of 500 $\mu$g/mL. In some cases, sonication in a Branson® 2200 sonicator (Branson Ultrasonics Corp., Danbury, Conn.) was required for complete dissolution. The steroid solutions were pipetted into the microtiter plate wells, 50 $\mu$L per well, which is equivalent to 25 $\mu$g of steroid per well. Unless stated otherwise, all assays discussed in the applications were performed at 25 $\mu$g steroid per well.

Quaternary ammonium compounds, the highest grade available, were purchased from one of the following: Sigma Chemical Co., St. Louis, Mo.; Research Plus, Inc., Bayonne, N.J.; Aldrich Chemical Co., Milwaukee, Wis. These compounds were stored as directed by the supplier. The quaternary ammonium compounds were dissolved in absolute ethanol at a concentration of 500 µg/mL. In some cases, sonication was required for complete dissolution. Dilution series of the quaternary ammonium solutions were prepared in absolute ethanol. Aliquots, 50 µL per well, of the appropriate dilutions were applied to the appropriate microtiter plate wells. Generally, the steroid solution was applied to the wells first. The quaternary ammonium compound solution at the appropriate dilution was then added second. However, the order of addition has no effect on assay results. The wells were then dried and the ELISA performed as outlined in IV-2-(d).

IV-2-(f) ELISA Results With Surrogate Antigens

A variety of combinations of chemical compounds have been coated onto microtiter plates and the ELISA [IV-2-(d)] run to determine if the Z2D3 monoclonal antibodies would bind to the coated compounds. Two specific types of compound are required for binding of the Z2D3 monoclonal antibodies. The first of these is a steroid with a structure very similar to cholesterol. The second is a quaternary ammonium compound with one of its substituents being a chain of at least twelve atoms in length. These are the minimal requirements for the formation of a surrogate antigen. Not all quaternary ammonium compounds, and by no means all steroids, form functional model antigens when dried on microtiter plates. The detailed requirements for surrogate antigen formations will be discussed below.

Steroid Component

Using the ELISA system, and the Z2D3 monoclonal antibodies, a wide variety of steroids and other components have been tested in the presence of one or more quaternary ammonium salts. These results are outlined in Table 2.

Regarding Table 2, the following should be noted. All of the values given are activities relative to the activity of cholesterol with the quaternary ammonium salt at the head of the column. For example, the ELISA activity with 5,7-cholestadien-3β-ol and benzalkonium chloride is twice that obtained with 5-cholesten-3β-ol and benzalkonium chloride. Table 2 does not, however, indicate the relative ELISA activities of the three quaternary ammonium salts shown. The relative ELISA activities of quaternary ammonium compounds will be discussed below.

The chemical structure of many of the steroids in Table 2 are very similar. Although only the highest available grades of steroid were used, the question of purity becomes an issue due to the sensitivity of the ELISA. With some of the steroids tested, a slight ELISA activity was noted at high concentrations of quaternary ammonium salt. Such activity could be attributed to the steroid being tested. However, such low levels of activity could also be due to contamination with small amounts of one of the highly active steroids. Consequently, none of the steroids tested were assigned a value of zero reactivity. Rather, non-reactive steroids are listed as exhibiting less than 5% of the activity of cholesterol. In most cases, such activity was significantly less than 5%. Also note that "nt" indicates that a given combination of steroid and quaternary ammonium salt has not been tested.

Results of ELISA's With Steroid Compounds

None of the triglycerides or other non-steroid compounds tested exhibit any ELISA activity. Of the many steroids tested, only a small number exhibit significant ELISA activity.

The chemical structures and ELISA activities of the six most active steroid compounds are shown in FIGS. 3–8. Of all steroids tested, 5,7-cholestadien-3β-ol, FIG. 4, exhibited the greatest ELISA activity in combination with nearly all of the quaternary ammonium salts tested. The chemical structures and ELISA activities of four non-reactive steroids are shown in FIGS. 9–12.

The high degree of specificity of the Z2D3 monoclonal antibodies is seen by comparing these figures. For example, comparing FIGS. 3 and 9, 5-androsten-3β-ol has exactly the same ring structure and hydroxy group positioning as 5-cholesten-3β-ol (cholesterol) but lacks the aliphatic "tail" at position 17 on the D ring. This structural change results in the complete loss of ELISA reactivity indicating that the aliphatic tail is essential for Z2D3 monoclonal antibody binding.

Several steroids with ring structures identical to cholesterol, but with differences in the chemical structure of the tail at position 17 were tested. Of these, only two, 5,24-cholestadien-3β-ol (Demosterol) with a double bond at position 24 in the tail and the non-mammalian sterol 5,24 (28)-stigmastedien-3β-ol with an ethylene group attached to carbon 24, exhibit significant ELISA activity. All other variations of the cholesterol tail tested, such as double bond at carbon 22 (5,22-stigmastadien-3β-ol), a hydroxy group at position 25 (5-cholesten-3β, 25-diol) or a keto group at position 25 (5-cholesten-3β-ol-25-one (27 nor)) show significantly reduced ELISA activity. Thus, the chemical structure of the aliphatic tail must meet certain conditions for binding of the Z2D3 monoclonal antibody to occur. Again comparing FIG. 3 to FIGS. 10 and 11, esterification or removal of the 3β hydroxy group completely eliminates ELISA activity. Several cholesterol esters are listed in Table 2, none exhibited activity in the ELISA. The 3β hydroxy group is, however, not essential for Z2D3 monoclonal antibody binding since significant ELISA activity was observed with 5-cholesten-3-one, a 3-keto steroid and palmitoyl choline. Significant activity was also detected with 5-cholesten-3α-ol (epicholesterol), a 3α sterol, and palmitoyl choline.

Chemical modification, the breaking of the 9–10 bond, of 5,7-cholestadien-3β-ol (7-dehydrocholesterol) (see FIG. 4) by ultraviolet light to form cholecalciferol (vitamin D3), FIG. 12, a process used by the human body, results in the loss of all ELISA activity. Several other steroids, which represent slight modifications of the structures of cholesterol, and which exhibit insignificant ELISA activity, are listed in Table 2.

Although each of the chemical structures of the six most active steroid compounds, FIGS. 3–8, are distinct form each of the other five, they are all closely related biochemically. FIG. 13 shows a small portion of the biochemical pathway of cholesterol biosynthesis and metabolism. All six of the highly active compounds in Table 2 are either immediate precursors or metabolites of cholesterol. All other commercially available precursors or metabolites of the six steroids in FIG. 13 have been found to give insignificant activity in the ELISA. It appears, therefore, that the steroid component of the Z2D3 monoclonal antibody antigen is cholesterol, a biological precursor or metabolite of cholesterol, for example, 5,7-cholestadien-3β-ol, or a combination of these.

Quaternary Ammonium Component. A number of quaternary ammonium salts have been tested in the presence of sterols using the ELISA assay and the Z2D3 monoclonal antibody. These results are outlined in Table 3.

The greatest ELISA activity is found with quaternary ammonium detergents, particularly the benzyldimethylalkyl detergents. A long chain substituent on the ammonium ion is required for ELISA activity. The degree of activity increases with the length of this chain.

Among the naturally occurring quaternary ammonium compounds tested, only choline esters exhibit any significant ELISA activity. A long chain substituent, in this case a fatty acid ester, is required for activity. The longer the fatty acid, the greater the ELISA activity, FIGS. 14 and 15.

These results, while demonstrating that a quaternary ammonium salt is essential for antibody binding, do not give a clear indication of the nature of the quaternary ammonium salt present in the naturally occurring antigen.

IV-2-(g) Summary Of Surrogate Antigen ELISA Results

Figure 13:
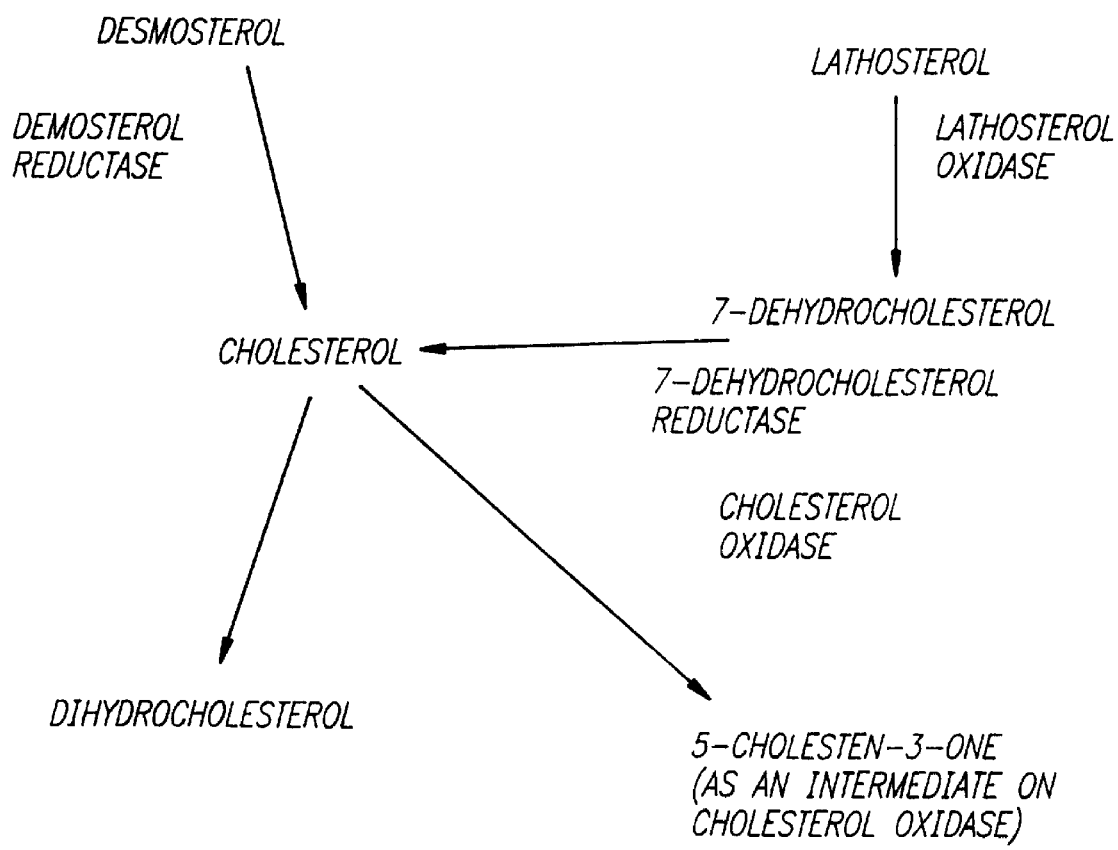
Figure 14:
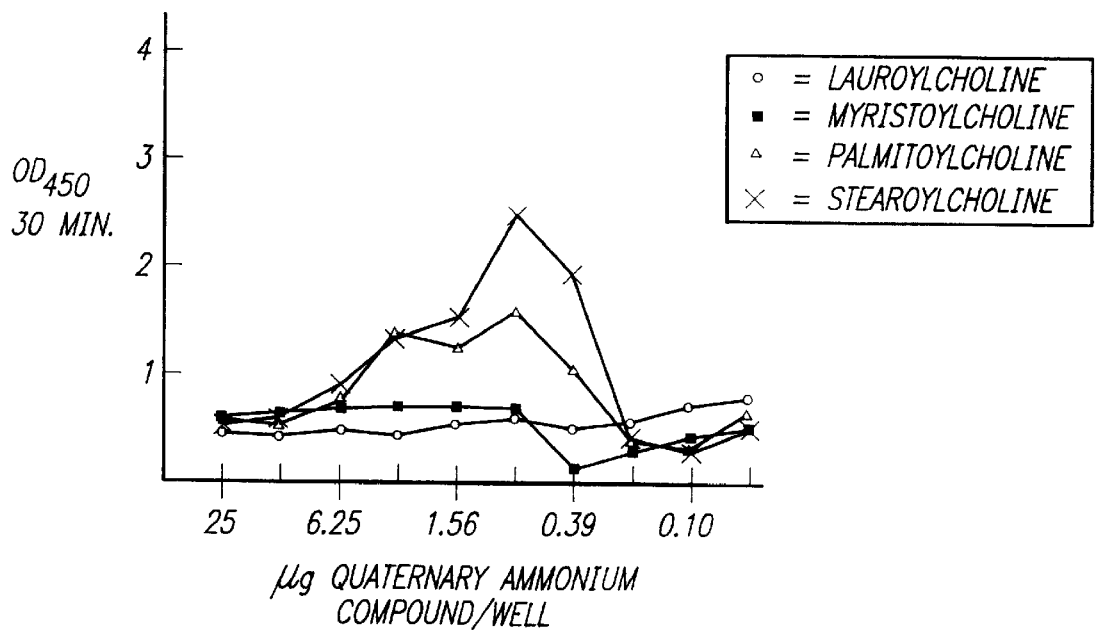
Figure 15:
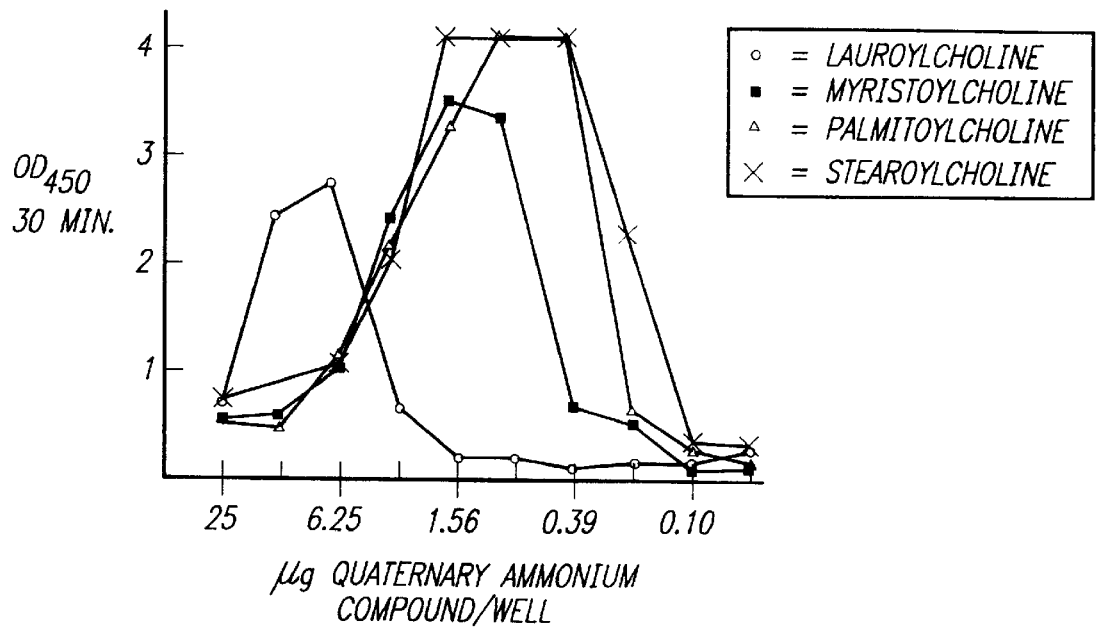

The results of surrogate antigen ELISA studies with the Z2D3 monoclonal antibody have shown that this antibody binds selectively to a combination of a steroid and a quaternary ammonium salt. Both components must be present for antibody binding to occur. Only a very limited number of steroids function as surrogate antigens, that is, facilitate the binding of the Z2D3 monoclonal antibody to the coated ELISA plate. In order to function as a surrogate antigen, a steroid must be either cholesterol or an immediate biochemical precursor or metabolite of cholesterol, FIG. 13. Of all steroids tested, 5,7 cholestadien-3β-ol (7-dehydrocholesterol), FIG. 4, consistently exhibited the greatest ELISA activity. A number of quaternary ammonium salts can function as a surrogate antigen, the majority being quaternary ammonium detergents.

The structural specificity of the antibody binding reaction (see section IV-2-(a)), implies that structural features known to be present in a surrogate antigen are probably also present in the naturally occurring antigen as found in human atherosclerotic lesions. Thus, it is very likely that the naturally occurring atherosclerotic antigen is, at least in part, comprised of a combination of a steroid, with a structure similar to cholesterol, and a quaternary ammonium salt.

To date, the surrogate antigen ELISA studies have yielded little information about the exact chemical nature of the naturally occurring quaternary ammonium salt. However, as discussed above (section IV-1-(b)), the naturally occurring antigen in human atherosclerotic tissue sections is destroyed or altered by the enzymatic action of phospholipase C. Phospholipase C hydrolyses phosphatidylcholine, a quaternary ammonium lipid component of animal cell membranes. It is therefore likely that phosphatidylcholine or a similar compound is involved in the formation of the naturally occurring antigen.

Phosphatidylcholine has not been found to function as the quaternary ammonium component of a surrogate antigen, Table 3. However, not all phosphatidylcholines have been tested. Antibody binding may be dependent upon one specific type of phosphatidylcholine. In addition, it may be that phosphatidylcholine is unable to bind properly to the ELISA plate so as to form a surrogate antigen. Therefore, the fact that phosphatidylcholine does not function as a surrogate antigen does not exclude it as a candidate for the quaternary ammonium component of the naturally occurring antigen in human atherosclerotic lesions.

V. Development Of Chimeric Z2D3 Monoclonal Antibody

This section will describe the work performed to produce a chimeric version of the mouse Z2D3 IgM antibody. The work has included: establishment of the hybridoma Z2D3; RNA isolation; immunoglobulin variable (V) region cDNA synthesis and subsequent amplification; cloning and sequencing of $V_H$ and $V_K$ cDNAs. The V regions were cloned into vectors for the expression of a mouse V/human IgG1 chimeric antibody from the rat myeloma cell line YB2/0 (ATCC Accession No. CRL 1662).

V-1. Cells And RNA Isolation

The hybridoma Z2D3.2B12, a subclone of the original Z2D3 was established and stocks frozen in liquid nitrogen. Total cytoplasmic RNA (130 μg) was isolated from approximately $10^7$ cells in the late logarithmic phase of growth. The medium in which the cells were grown at the time of RNA isolation was assayed and the presence of an antibody of isotype IgM Kappa, was confirmed. Furthermore, the secreted antibody was shown to bind to atherosclerotic plaque antigen in an ELISA.

V-2. cDNA Synthesis

Ig V cDNAs were made from Z2D3 RNA via reverse transcription initiated from primers based on sequences at the 5' ends of the murine IgM and kappa constant regions. The sequences of these primers, CM1FOR and K2FOR, are shown in Table 4.

V-3. Amplification Of $V_H$ And $V_K$ cDNA

Figure 16:
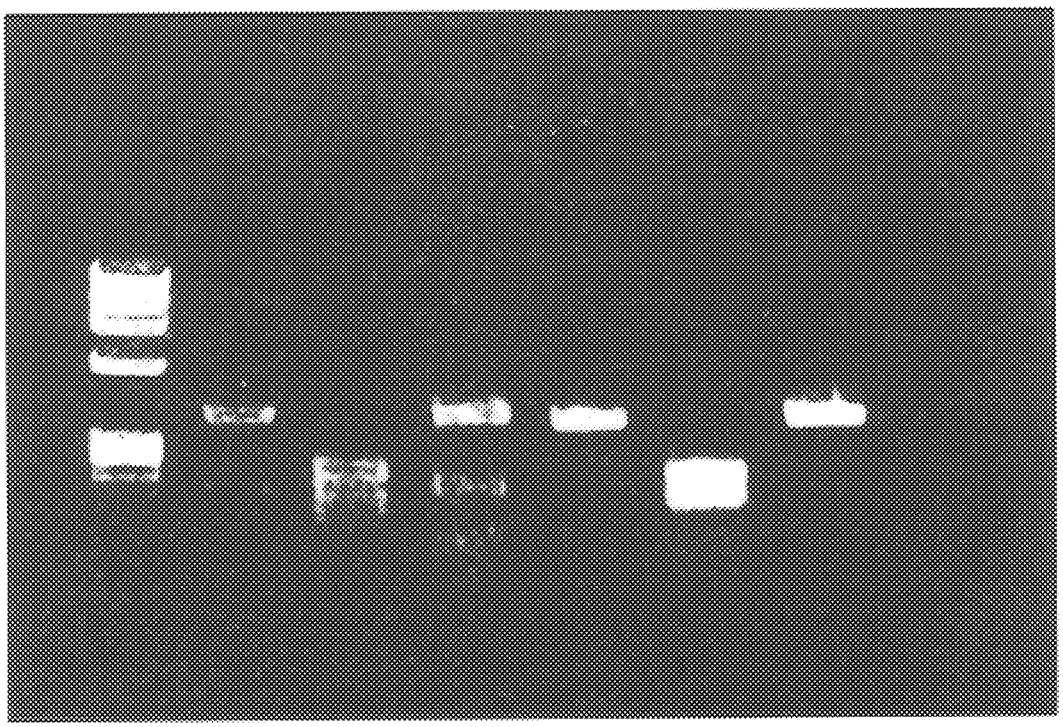

Ig VH and VK cDNAs were amplified by the polymerase chain reaction (PCR) [Saiki, R. K., Scharf, S., Faloona, F., Mullis, K. B., Horn, G. T., Ehrlich, H. A. and Arnheim, N. (1988) Science, 239: 487–491.] [Orlandi, R., Gussow, D. H., Jones, P. T., and Winter, G. (1989) Pro. Nat'l. Acad. Sci. USA 86: 3833–3837.] The same 3' oligonucleotides used for cDNA synthesis were used in conjunction with appropriate 5' oligonucleotides, VH1BACK and VK1BACK (Table 4), which are based on consensus sequences of relatively conserved regions at the 5' end of each V region [Orlandi, R., Gussow, D. H., Jones, P. T., and Winter, G. (1989) Pro. Nat'l. Acad. Sci. USA 86: 3883–3837.] The product of amplification of VH DNA using VH1BACK and CM1FOR primers is shown in FIG. 16 where a DNA species of the expected size (~400 bp) can be seen. For cloning VH DNA into vectors for the expression of Fab fragment or the chimeric antibody, another primer, VH1FOR (Table 4) in concert with VH1BACK, was used to introduce a BstEII site at the 3' end of the V region.

FIG. 16 also shows amplified DNA obtained using VK1BACK and CK2FOR primers in a PCR. This fragment is of the anticipated size (~350bp). VK DNA was also amplified using VK4BACK and VK2FOR, or VK1BACK and VK1FOR to introduce restriction enzyme sites necessary for cloning into bacterial Fab expression vectors or chimeric expression vectors respectively.

V-4. Cloning And Sequencing VH DNA

The primers used for the amplification of VH DNA contain the restriction enzyme sites PstI and HindIII. One or more internal PstI sites was found within the amplified VH DNA (FIG. 16). The DNA was cloned as PstI-PstI and PstI-HindIII fragments in M13 mp18 and mp19. The resulting collection of clones were sequenced and the extent of sequence determined from each clone is shown in FIG. 17. Apart from the occasional Taq polymerase-induced error, the sequences obtained were unambiguous. The contiguity of the two fragments was demonstrated after sequencing the entire VH region obtained after a partial PstI digest and cloned into the Fab bacterial expression vector.

The Z2D3 VH DNA sequence and its translation product are shown in FIG. 18. It should be noted that the first eight amino acids are dictated by the oligonucleotides use in the PCR and are not necessarily identical to those of the murine antibody. Computer-assisted comparisons indicate that Z2D3 VH is most closely related to Kabat subgroup IIIB [Kabat, E. A., Wu, T. T., Reid-Miller, M., Perry, H. M. and Gottesman, K. S. (1987) Sequences of proteins of immunological interest. U.S. Dept. of Health & Human Services, U.S. Government Printing Office.] (FIG. 19). Four residues in framework 1 viz Arg18, Gly19, Glu23, Gly24 are unusual for the positions. All three CDRs are unique and have not been reported in any other murine VH.

V-5. Cloning And Sequencing VK DNA

The primers used for the amplification of VK DNA contain the restriction enzyme sites PvuII and HindIII. One or more HindIII sites was found within the amplified VK DNA (FIG. 16). The VK DNA was cloned as PvuII-HindIII and HindIII-HindIII fragments in M13 mp18 and VK2FOR (which introduce SacI and XhoI restriction sites) were also cloned and sequenced to ensure contiguity around the HindIII site. The extent of sequence determined from 18 clones is shown in FIG. 20. Apart from a few errors arising during the PCR, the sequence obtained was unambiguous. No clones containing any other kappa chain sequence were found.

During the sequencing of VH clones, three clones were noted to contain framework 1 of VK together with a putative signal sequence. The likely explanation for this is that CM1FOR is quite similar in sequence to CDR1 of VK and with VH1BACK, which must have annealed in the 5'-untranslated region, amplified this part of the kappa chain gene.

FIG. 21 shows the entire VK DNA sequence, including the signal sequence, and its translated product. Computer-assisted comparisons indicate that Z2D3 VK is a member of the Kabat family V [Kabat, E. A., Wu, T. T., Reid-Miller, M., Perry, H. M. and Gottesman, K. S. (1987) Sequences of proteins of immunological interest. U.S. Dept. of Health & Human Services, U.S. Government Printing Office.] FIG. 22 shows a comparison between the Z2D3 VK and a family V consensus sequence. The only unusual residue is at position 42 (Kabat position 41) which is often glycine; there is no reported example of tryptophan at this position.

V-6. Z2D3 Chimeric Antibody

The Z2D3 VH and VK genes were first cloned as PstI-BstEII and PvuII-BglII fragments into M13 vectors containing the heavy chain immunoglobulin promoter, signal sequence and appropriate splice sites. For VH this necessitated introduction of a BstEII site into the 3' end of VH and was accomplished by subjecting cDNA primed with CM1FOR to a second PCR using VH1FOR with VH1BACK. Similarly, a BglII site was introduced into the 3' end of VK using VK1BACK in a second PCR. In retrospect, the use of VH1BACK was not necessary as a naturally occurring BstEII site was present. However, the introduction of the BglII site changed Leu106 to Ile in VK.

Figure 23:
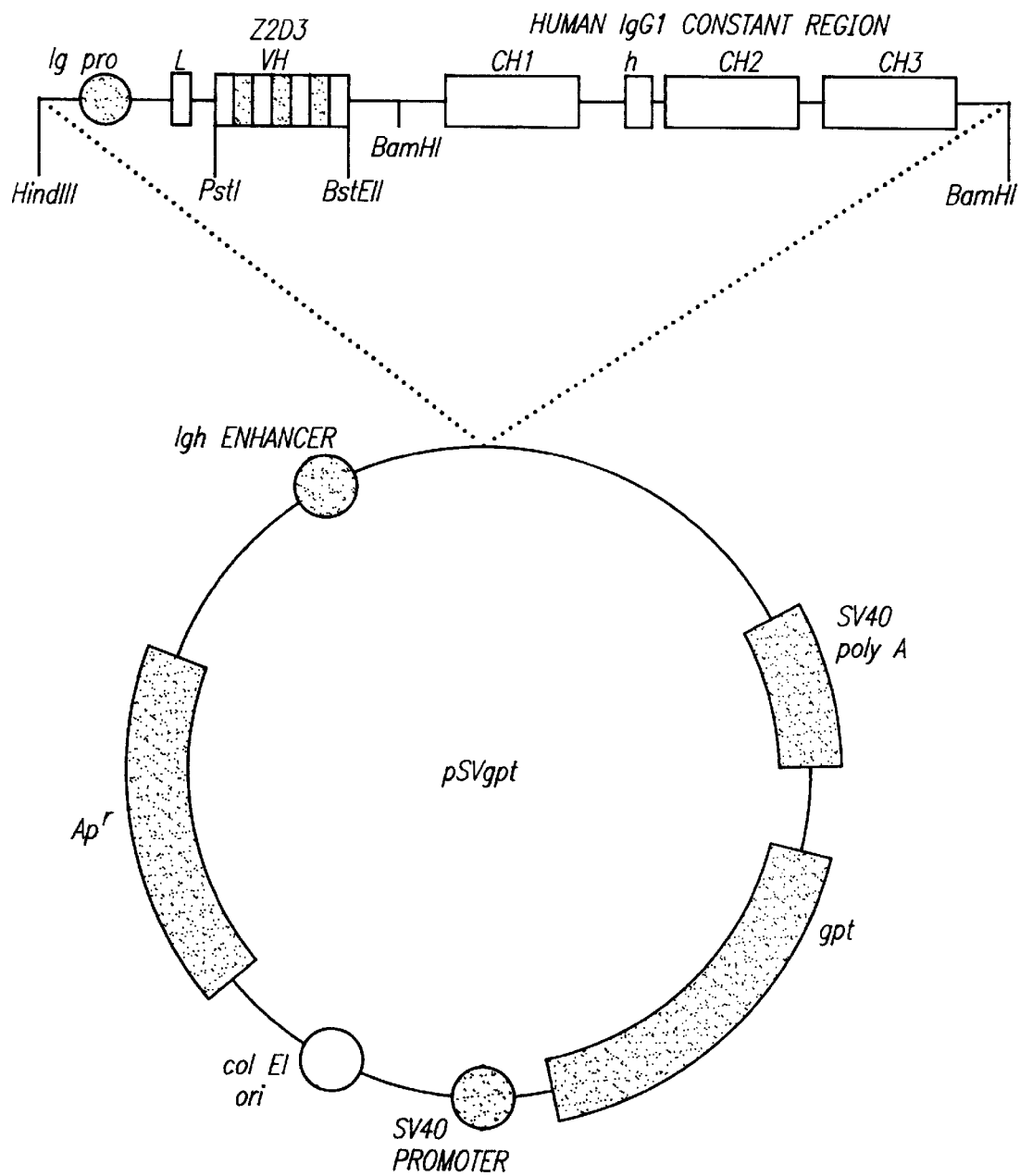
Figure 24:
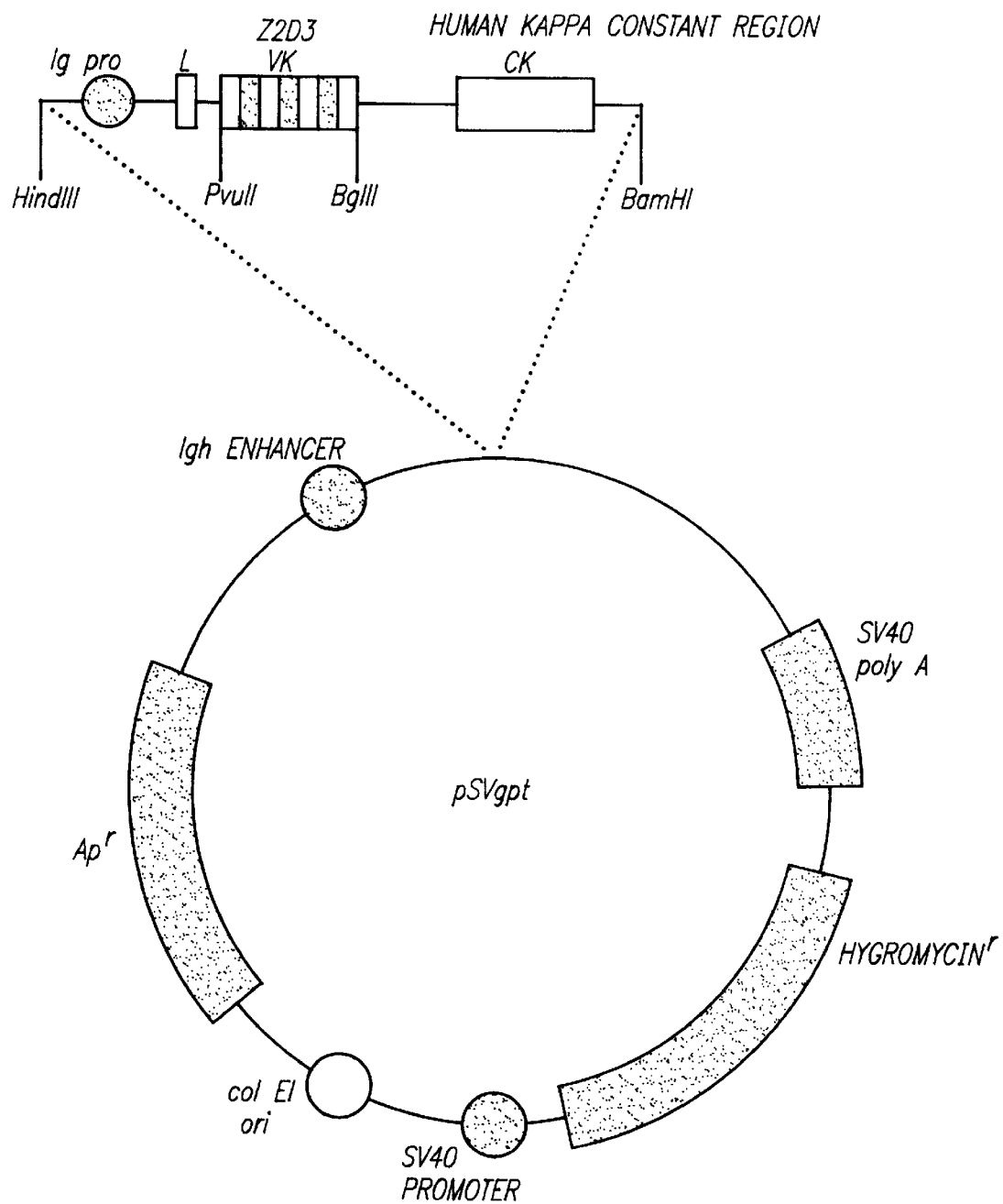

The VH and VK genes together with appropriate expression elements were excised from their respective M13 vectors as HindIII-BamHI fragments and cloned into pSVgpt and pSVhyg [Orlandi, R., Gussow, D. H., Jones, P. T., and Winter, G. (1989) Pro. Nat'l. Acad. Sci. USA 86: 3883–3837.] (FIGS. 23 and 24). pSVgpt contains an immunoglobulin enhancer sequence, an SV40 origin of replication, the gpt gene for selection and genes for replication and selection in E.coli. Finally, a human IgG1 constant region [Takahashi, N. Veda, S., Obatu, M., Nikaido, T., Nakai, S., and Honjo, T. (1982) Cell 29: 671–679] was added as a BamHI fragment. The pSVhyg vector for the expression of the light chain is essentially the same, except that the gpt gene is replaced with the hygromycin resistance gene and a human kappa chain constant region was added [Heiter, P. A., Max, E. E., Seidman, J. G., Meizel, J. V. Jr., and Leder, P. (1980) Cell 22: 197–207.]

10 µg of the heavy chain expression vector and 20 µg of the kappa chain expression vector were digested with PvuI and cotransfected by electroporation into approximately 10% YB2/0 rat myeloma cells (ATCC accession Number CRL 1662) [Kilmartin, J. W., Wright, B., and Milstein, C. (1982) Jour. Cell Biol. 93: 576–582]. After 48 hour recovery in non-selective medium, the cells were distributed into a 24-well plate and selective medium applied (DMEM, 10% fetal calf serum, 0.8 µg/ml mycophenolic acid, 250 µg/ml xanthine). After 3–4 days, medium and dead cells were removed and replaced with fresh selective medium. gpt+ transfects were visible with the naked eye 8–10 days later. Uptake of the kappa chain expression vector (resistance to hygromycin) was not selected because of high proportion (50–100 %) of mycophenolic acid resistant clones were cotransfected with the kappa chain expression vector.

The presence of chimeric antibody in the medium of wells containing transfected clones were measured by ELISA. Wells of a micro-titre plate were coated with goat anti-human IgG (gamma chain specific) antibodies. Culture medium was applied and any human antibody bound was detected with peroxidase conjugated goat anti-human IgG and peroxidase conjugated goat anti-human kappa chain antibodies. 24/24 wells were positive for human IgG and human CK.

Figure 25:
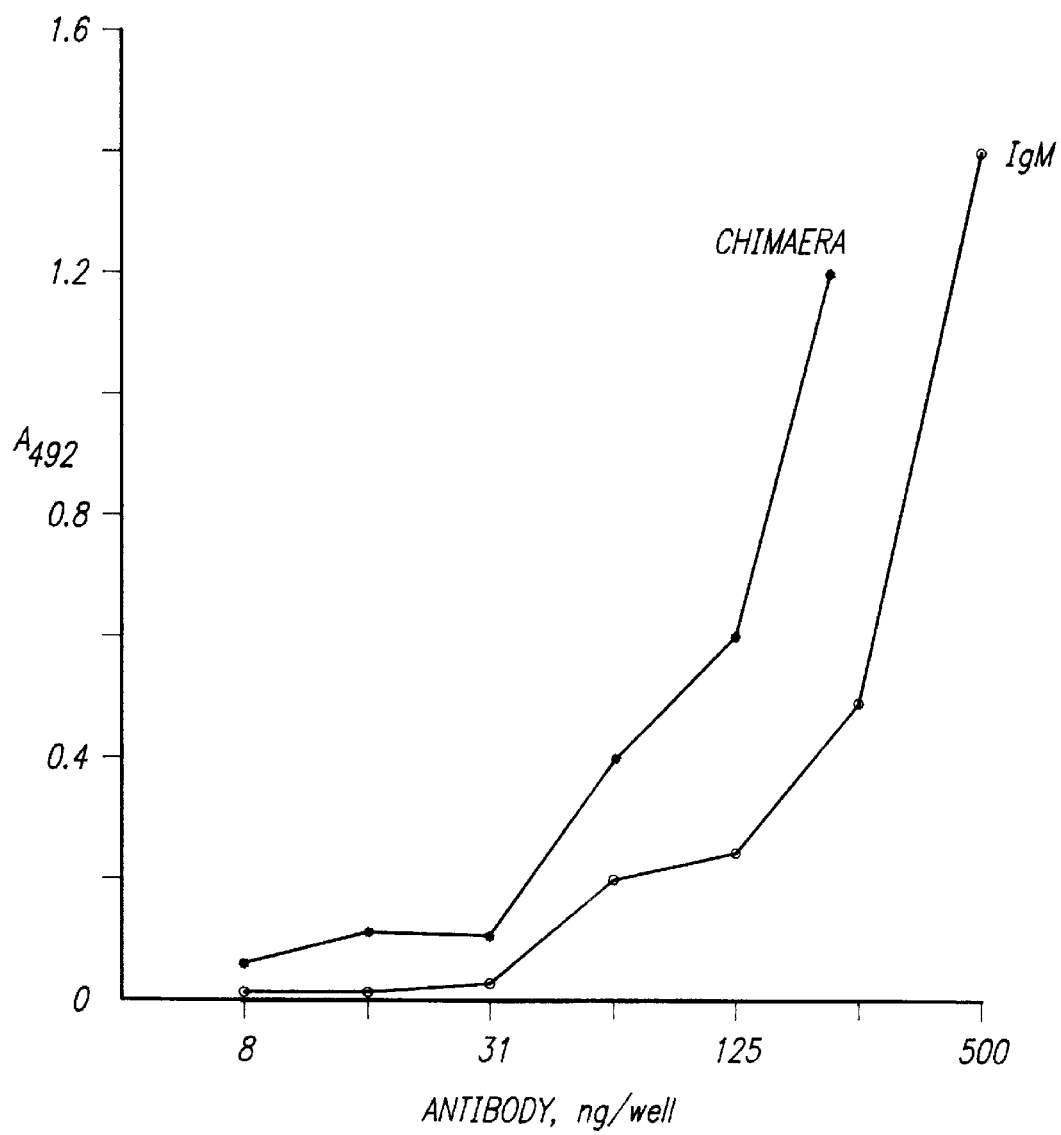

Cells from wells showing the highest ELISA readings were expanded and antibody purified from culture medium by protein A affinity chromatography. The ability of the chimeric antibody to bind to antigen was measured by ELISA protocol. FIG. 25 shows that the Z2D3 mouse/human IgG1 chimeric antibody is able to bind to antigen with similar efficiency to the progenitor Z2D3 mouse IgM antibody.

V-7. Tissue Culture Production Of Z2D3 Chimeric Antibody

A subclone of the chimeric cell line Z2D3M Vh/M VK 73/30 identified as 1D10 was used for the production of the antibody in tissue culture. The cells (3–4×10$^6$ cells per mL) were grown in RMPI 1640 medium (with L-glutamine) with a supplement of 1.5% fetal calf serum at 36°±1° C. in the presence of 5% $CO_2$. After 6–8 days, the cells were removed from the medium by centrifugation and the supernatant was stored at 4° C.

V-8. Purification Of Z2D3 Chimeric Antibody

The tissue culture supernatant (Section V-7) was concentrated about 100-fold by tangential flow ultrafiltration using a Minitan Concentrator (Millipore, Bedford, Mass.) equipped with a 30,000 MW cut-off polysulfone membrane. The pH of the resultant concentrate was adjusted to 7.6±0.1 with dilute sodium hydroxide, and centrifuged at 15,000×g for 35 minutes to remove residual cells. The concentrate was then applied to a PBS-equilibrated Prosep A® column (Bioprocessing, Ltd., Consett Co., England) 1 mL of Prosep A for each 50 mL of concentrate, at a flow rate of approximately 1 mL/minute. The column was washed with ten column volumes of PBS.

The bound chimeric antibody was eluted from the column with 100 mM sodium citrate buffer, pH 4.0. Fractions of a suitable size were collected. The antibody containing fractions were identified by $OD_{280}$, pooled, and dialyzed against PBS at 4° C. The antibody was then aseptically filtered and stored at 4° C.

V-9. Preparation Of Immunologically Active F(ab')$_2$ Fragments Of The Chimeric Z2D3 Antibody Chimeric Z2D3 antibody, at a concentration of approximately 4 mg/mL, was dialyzed extensively against 25 mM sodium citrate buffer, pH 3.50. Porcine pepsin (Sigma) was added to a final ratio of 1 µg of pepsin for each 175 µg of antibody. This solution was incubated at 37° C. for 2 hours.

The pH of the reaction mixture was adjusted to 7.6 by the addition of 1M Tris base. This solution was then applied to a Prosep A column (BioProcessing Ltd., Durham, England) to remove undigested whole antibody molecules. The column was washed with PBS. The flow through fractions containing the F(ab')$_2$ fragments were pooled and concentrated to a small volume in a stir cell concentrator (Amicon Div., W. R. Grace, Beverly, Mass.). The F(ab')$_2$ fragments were separated from small peptides and other low MW reactants by size exclusion HPLC on a SEC-250 column (Bio-Rad) equilibrated in 100 mM potassium phosphate pH 7.0. The F(ab')$_2$ containing fractions were pooled and stored at 4° C.

V-10. Immunohistological Staining With The Chimeric Z2D3 Monoclonal Antibody

Purified Z2D3 chimeric antibody in PBS was conjugated to biotin (sulfosuccinimidyl-6-(biotinamido) hexaneate, Pierce) in an ice-bath. Twenty micrograms of biotin (in dry DMSO (Dimethyl sulfoxide), at a concentration of 10 mg/mL) was added for each milligram of antibody. The reaction mixture was incubated at 0° C. for 2 hours with occasional mixing. Unreacted biotin was removed by extensive dialysis in PBS and the biotin-antibody conjugate was then filtered aseptically and stored at 4° C.

The biotinylated Z2D3 chimeric antibody was used to stain unfixed, frozen human atherosclerotic tissue sections (5–6 $\mu$m thick) by immunohistology using a procedure similar to that of Section III. The tissue sections were incubated with the biotinylated antibody for 2 hours at ambient temperature in a humidified container. The sections were washed with PBS/BSA and endogenous peroxidases were blocked with 0.3% hydrogen peroxide in methanol. The sections were then incubated with avidin-biotinylated horseradish peroxidase complex (Vectostain ABC reagent, Vector PK-6100) for 20 minutes; washed with PBS/BSA, incubated with a buffered solution of 3,3'-Diaminobenzidine, washed with water, and counter-stained with hematoxylin.

Figure 26A:
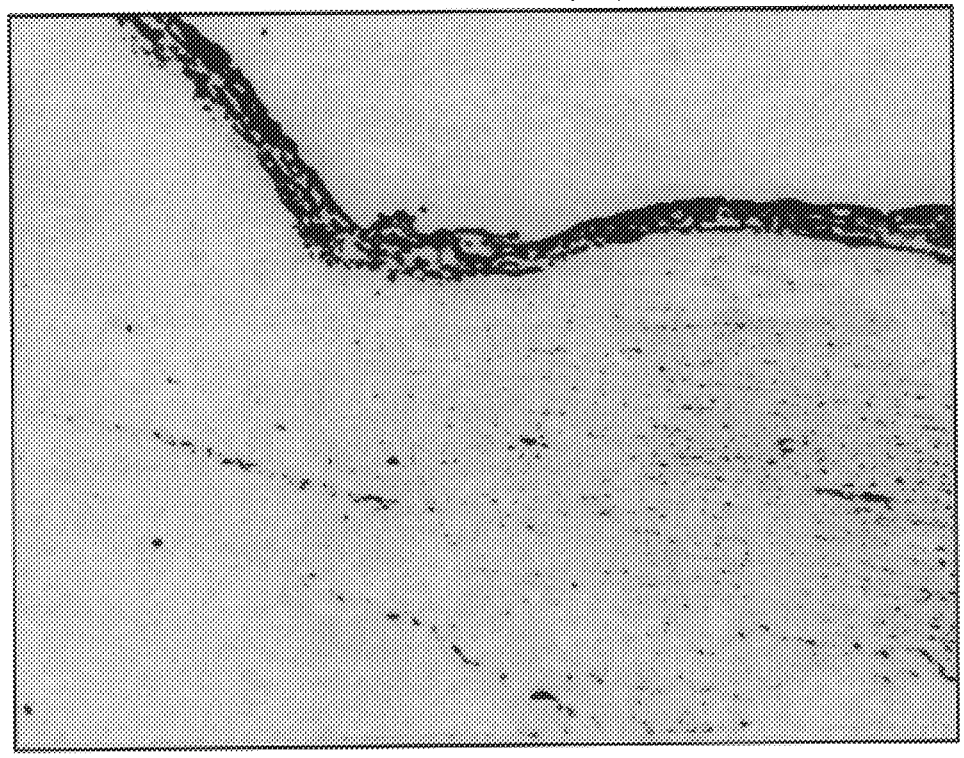
Figure 26B:
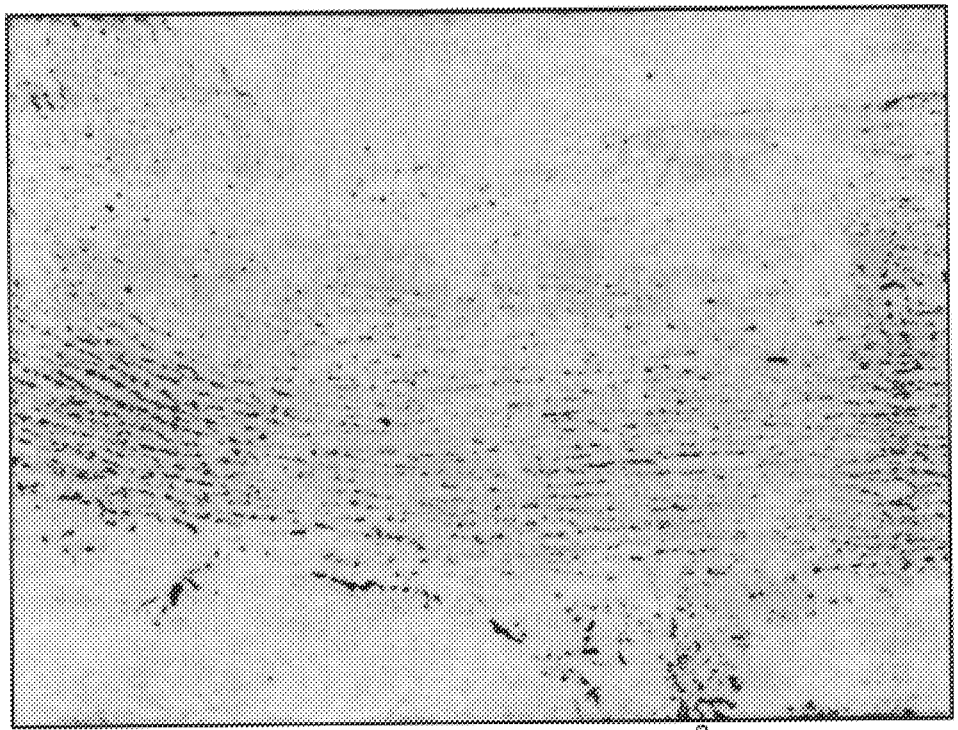
Figure 27A:
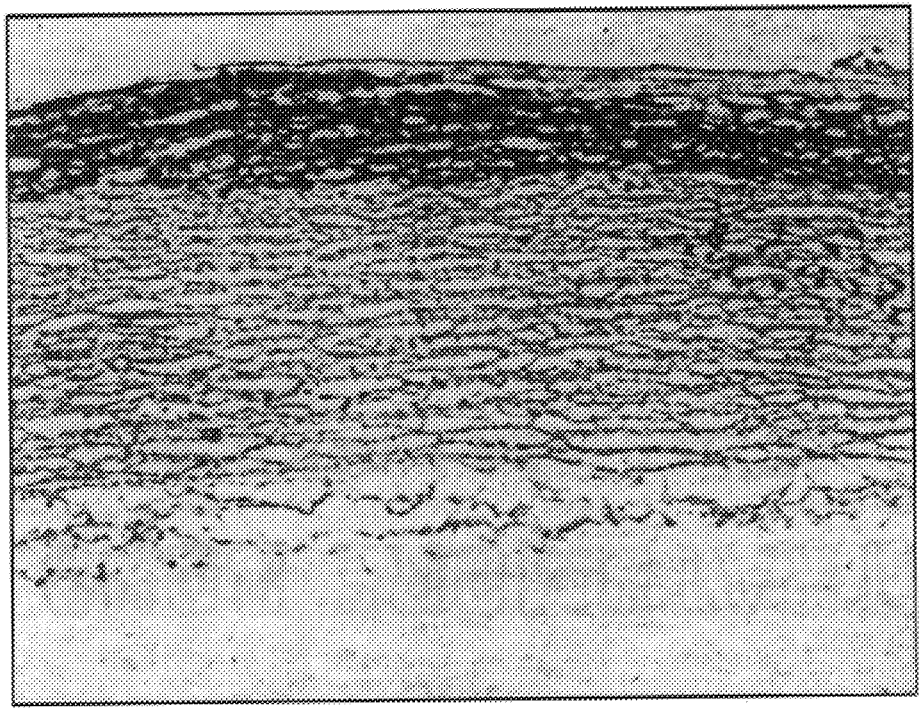
Figure 27B:
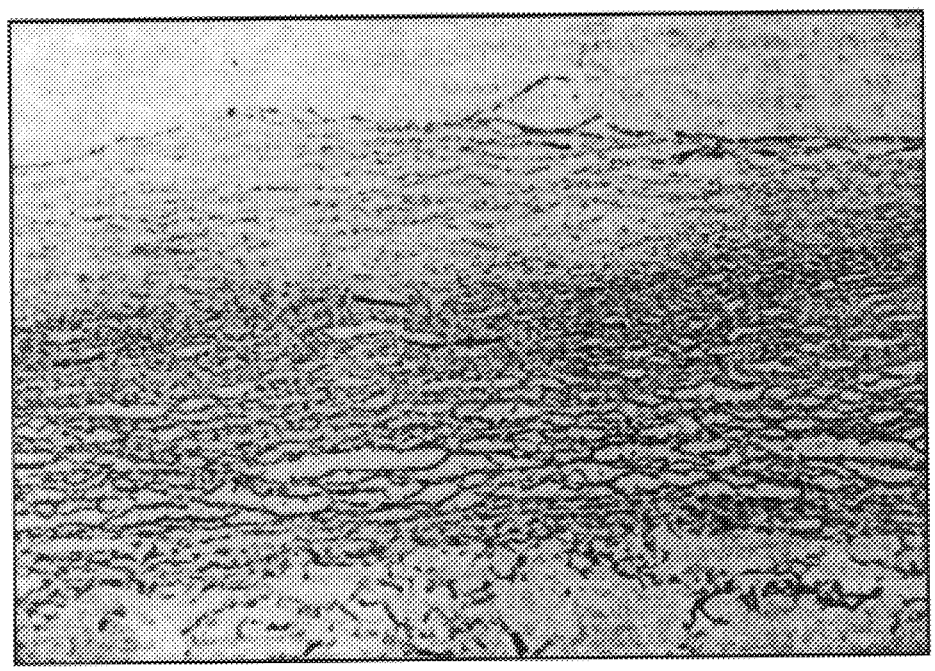
Figure 28A:
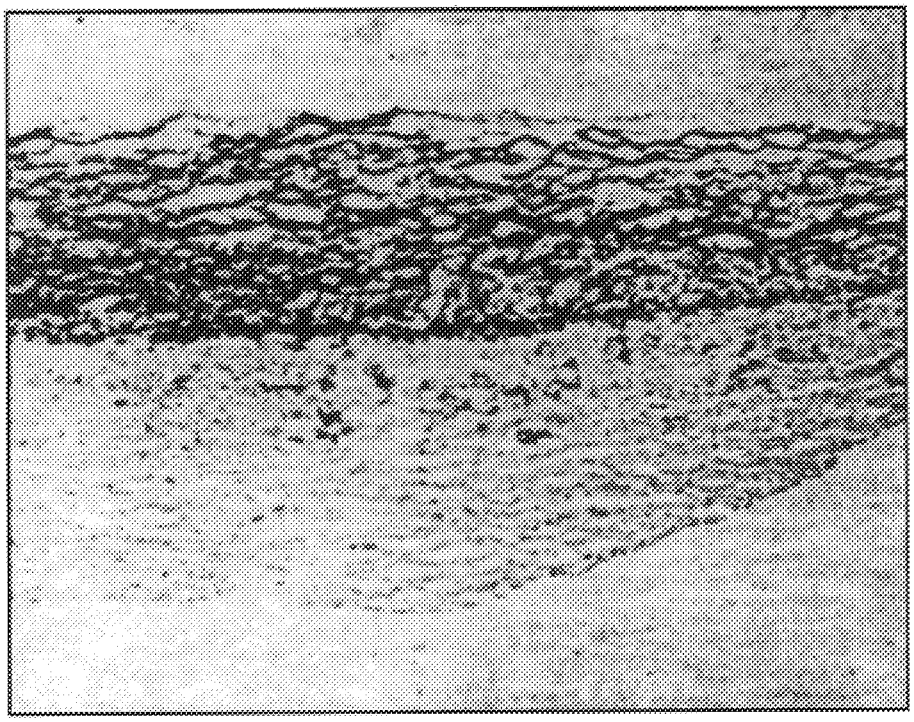
Figure 28B:
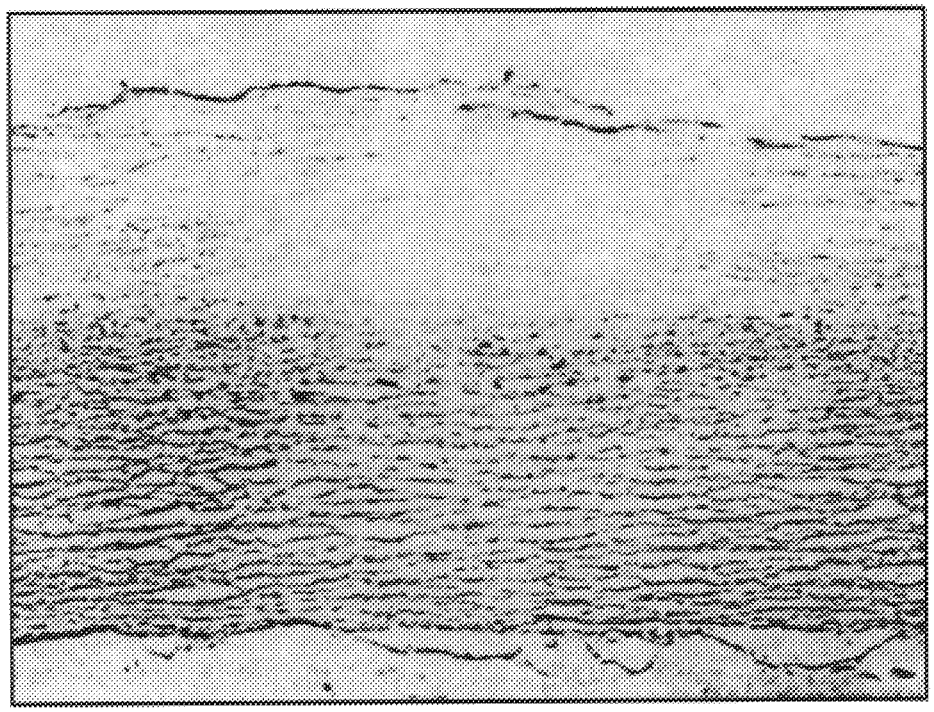

The Z2D3 chimeric antibody specifically stains atherosclerotic lesion and not any of the surrounding normal artery (see FIGS. 26, 27, 28) in exactly the same manner as the mouse Z2D3 monoclonal antibody. The chimeric antibody is highly specific for the lesion areas of atherosclerotic tissue sections and does not stain tissues from any other organs tested (see Table 5).

VI. Development Of New Monoclonal Antibodies Using Surrogate Antigens As The Immunogen As outlined in section IV-2(b), an immunologically reactive model or surrogate of the Z2D3 antigen can be created by coating cholesterol or a related steroid and a specific type of quaternary ammonium compound onto polystyrene. Surrogate antigens have been used to generate new monoclonal antibodies with specificities very similar to the original Z2D3 monoclonal antibody.

VI-1. Preparation Of Polystyrene Beads Coated With The Surrogate Antigen

Polystyrene beads, average diameter 11.9 $\mu$m (Sigma cat.# LB-120) were washed and resuspended in absolute ethanol. The resulting suspension was separated into aliquots each containing approximately 4 $\mu$g of beads. Individual aliquots of beads were then coated with the surrogate antigens, each a combination of a steroid and a quaternary ammonium salt, listed below.

Surrogate Antigen Combination #1: 7-Dehydrocholesterol And Benzyldimethylhexadecylammonium Chloride.

Five hundred micrograms of 7-Dehydrocholesterol (Sigma) (250 $\mu$L of a 2 mg/mL solution in ethanol) and 31 $\mu$g of Benzyldimethylhexadecylammonium chloride (Sigma) (31 $\mu$L of a 1 mg/mL solution in ethanol) were added to each aliquot receiving this combination. Each aliquot was thoroughly mixed and the solvent was then allowed to evaporate at ambient temperature. The coated beads were stored at 4° C. until use.

Surrogate Antigen Combination #2: 7-Dehydrocholesterol And Palmitoylcholine.

Five hundred micrograms of 7-Dehydrocholesterol (Sigma) (250 $\mu$L of a 2 mg/mL solution in ethanol) and 15.5 $\mu$g palmitoylcholine (Sigma) (15.5 $\mu$L of a 1 mg/mL solution in ethanol) were added to each aliquot receiving this combination. The beads were processed and stored as for combination #1.

Surrogate Antigen Combination #3: Cholesterol And Benzyldimethylhexadecylammonium Chloride.

Five hundred micrograms of cholesterol (Sigma) (250 $\mu$L of a 2 mg/mL solution in ethanol) and 31 $\mu$g of Benzyldimethylhexadecylammonium chloride (Sigma) (31 $\mu$L of a 1 mg/mL solution in ethanol) were added to each aliquot receiving this combination. The beads were processed and stored as for combination #1.

Surrogate Antigen Combination #4: Cholesterol And Palmitoylcholine.

Five hundred micrograms of cholesterol (Sigma) (250 $\mu$L of a 2 mg/mL solution in ethanol) and 15.5 $\mu$g palmitoylcholine (Sigma) (15.5 $\mu$L of a 1 mg/mL solution in ethanol) were added to each aliquot receiving this combination. The beads were processed and stored as for combination #1.

Surrogate Antigen Combination #5: 5-Cholesten-3-one And Benzyldimethylhexadecylammonium Chloride.

Five hundred micrograms of 5-cholesten-3-one (Sigma) (250 $\mu$L of a 2 mg/mL solution in ethanol) and 31 $\mu$g of Benzyldimethylhexadecylammonium chloride (Sigma) (31 $\mu$L of a 1 mg/mL solution in ethanol) were added to each aliquot receiving this combination. The beads were processed and stored as for combination #1.

Surrogate Antigen Combination #6: 5-Cholesten-3-one And Palmitoylcholine.

Five hundred micrograms of 5-cholesten-3-one (Sigma) (250 $\mu$L of a 2 mg/mL solution in ethanol) and 15.5 $\mu$g palmitoylcholine (Sigma) (15.5 $\mu$L of a 1 mg/mL solution in ethanol) were added to each aliquot receiving this combination. The beads were processed and stored as for combination #1.

VI-2. Immunization Of Mice With Surrogate Antigen Coated On Polystyrene Beads

For each mouse to be immunized with a surrogate antigen, two aliquots, or about 8 $\mu$g of beads, were suspended in saline and emulsified in Freund's Complete Adjuvant (Difco). The emulsified beads were injected subcutaneously at multiple sites. Two weeks after the initial injections, each mouse was boosted. Two aliquots of beads were suspended in saline and emulsified in Freund's Incomplete Adjuvant (Difco). The emulsified beads were injected subcutaneously. Two weeks after the first boost, each mouse was boosted again, receiving one aliquot of beads emulsified in Freund's Incomplete Adjuvant and injected intraperitoneally.

Using this method, six groups of mice, fourteen mice in all, were prepared. Three mice received surrogate antigen combination #1, three mice received surrogate antigen combinations #2, and two mice each received surrogate antigen combinations #3, 4, 5 and 6.

Seven days after the final boost, the mice were bled. The resulting sera were tested by ELISA (Section IV-2). All fourteen mice exhibited a strong IgM response to the immunizing antigen. None of the mice exhibited an IgG response. The sera were also tested by immunohistology as outlined in section III using a peroxidase conjugated anti-mouse IgM as the secondary antibody. Specific staining of human atherosclerotic lesions was observed with all fourteen sera at a 1:25 dilution.

One mouse, number R-2, was selected for fusion based on a higher titer in the ELISA and on a slightly more intense staining of the lesion areas with its serum. Mouse R-2 was immunized with surrogate antigen combination #1, 7-dehydrocholesterol and benzyldimethylhexadecylammonium chloride.

Nine days after the preliminary bleed, mouse R-2 was boosted again with 4 μg of surrogate antigen-coated beads suspended in saline, injected interperitoneally. Three days later, the spleen was taken for fusion.

VI-3 Fusion Procedure

SP2 myeloma cells (non-secreting fusion line SP2/01-Ag 14, ATCC\ Accession No. CRL8006) were grown in RPMI medium (Gibco) with 15% FCS (Hyclone) pen strep and L-glutamine (Gibco) in a 5% carbon dioxide atmosphere. At least $5 \times 10^7$ SP2 cells were collected in log phase from petri dishes and centrifuged at 230×g for eight minutes. The pellet was resuspended in 40 mL RPMI medium and the suspension placed in a 50 mL polypropyline centrifuge tube.

A single cell suspension of the immunized spleen from mouse R-2 was prepared in 5 mL of RPMI medium by maceration with the frosted ends of two sterile glass slides. The cell suspension was transferred to a sterile 15 mL tube and any clumps allowed to settle for one minute. The cell suspension was then carefully removed from the settled clumps and transferred to the SP2 cells in the 50 mL tube. Hybridoma cloning factor (Igen) was then added to a final concentration of 10%. This mixture was incubated at 37° C. for two hours.

The cell suspension was centrifuged at 275×g for eight minutes. The supernatant was removed and 2 mL of 40% PEG (pre-warmed to 37° C.) were added. The pellet was gently resuspended in the 40% PEG. This suspension was centrifuged at 275×g for six minutes. The supernatant was carefully removed and 6 mL of RPMI medium was added. The cells were gently mixed and centrifuged at 230×g for six minutes. The supernatant was removed and 10 mL of growth medium, RPMI with 15% FCS, was added. The cells were gently mixed without disrupting clumps. This suspension was incubated at 37° C. for 30 minutes to allow for completion of the fusion reaction.

Fusion medium was prepared as follows: 50 mL Hybridoma Cloning Factor (Igen), 90 mL FCS (Hyclone), 5 mL of pen strep (Gibco), 1.5 mL L-glutamine (Gibco) and 1 vial of azaserine/hypoxanthine (Sigma) were combined. The total volume was then adjusted to 500 mL with RPMI medium containing L-glutamine (Gibco).

Twenty-eight 96-well plates (Becton Dickinson Labware) were labeled for identification. Freshly prepared fusion medium, 500 mL, was sterile filtered into a sterile 750 mL flask and warmed to 37° C. The fused cells were transferred to the 750 mL flask containing sterile fusion medium and gently mixed. This suspension was transferred to the labeled 96-well plates, 200 μL per well. The plates were then incubated in an atmosphere of 5% $CO_2$ at 37° C.

Twelve days after the fusion, growing hybrids were identified by examining the plates with a microscope. When the growing hybrids had expended the nutrients in the medium, approximately 13–14 days after fusion, 200 μL of medium were removed from each well and saved for assay. The removed volume was replaced with Fusion Medium without Azaserine. As positive clones were identified by assay, the cells were harvested from the appropriate wells and expanded using standard cell culture techniques.

VI-4 Results

From the initial fusion of a surrogate antigen immunized mouse spleen described in the previous section, seven new monoclonal antibodies with specificities identical to the original Z2D3 monoclonal IgM have been identified. All seven of these clones produce IgM monoclonal antibodies.

Immunohistology with frozen atherosclerotic tissue sections, as in Section III, has demonstrated that each of the seven antibodies developed by surrogate antigen immunization binds specifically to the atherosclerotic lesion area. No detectable binding to surrounding normal tissues was observed.

The binding properties of the seven new monoclonal antibodies have also been studied by ELISA (Section III). Twelve different combinations of steroid (Table 2) and quaternary ammonium compounds (Table 3) were coated on ELISA plates and the ELISA performed as in Section IV-2-(d). No significant differences between the original Z2D3 monoclonal antibody developed with human atherosclerotic plaque extract and any of the seven monoclonal antibodies developed with the surrogate antigen were observed. For example, the original Z2D3 IgM binds to a combination of 5,7-cholestadien-3β-ol and benzyldimethylhexadecylammonium chloride. Likewise, each of the seven new monoclonal antibodies binds readily to this combination. The original Z2D3 does not bind to a combination of 5-cholesten-3β-ol acetate and benzyldimethylhexadecylammonium chloride. None of the seven new monoclonal antibodies binds to this combination.

Finally, the binding specificity of the surrogate antigen monoclonal antibodies was studied by immunohistology using a competitive immunoassay format. Individual solutions of the surrogate antigen monoclonal antibodies were incubated on frozen human atherosclerotic tissue sections for 1 hour in a humidified atmosphere. The sections were then washed and a solution of biotinylated Z2D3 IgM monoclonal antibody was added. The remainder of the procedure was as described in section V-10.

Under these conditions, no staining of the human atherosclerotic lesions was observed. That is, the surrogate antigen antibodies competed effectively with the original murine Z2D3 monoclonal antibody for binding sites on the human atherosclerotic lesions. The generation of immunologically active, highly specific, monoclonal antibodies by means of immunization with a surrogate antigen as defined in section IV-2 conclusively demonstrates that the immunogenic epitope presented by the surrogate antigen is structurally very similar, if not identical, to the naturally occurring epitope formed during the development of an atherosclerotic lesion.

VII. Imaging Of Atherosclerotic Plaque

The unique specificity of the Z2D3 monoclonal antibody for an epitope or epitopes localized in atherosclerotic lesions provides an opportunity to deliver defined agents directly to the site of the lesion in vivo. The Z2D3 antibody binds to atherosclerotic lesions during all stages of plaque development. As a consequence, the Z2D3 monoclonal antibody is superior to other antibodies which have been used in published imaging studies (see references in Background Of The Invention, above).

The Z2D3 monoclonal antibody or an immunologically active fragment thereof may be coupled to an imaging marker of choice by means of one of a variety of conjugation methods available to the protein chemist. The choice of marker would depend on the type of imaging technology to be employed but would be readily apparent to one skilled in the art of medical imaging.

Preliminary investigation of one imaging technique using radioisotope labeled Z2D3 antibody fragments is presently in progress. The radioisotope indium-ill was attached to the Z2D3 via the metal chelator diethylenetriaminepentaacetic acid. The results to date are reported below.

VII-1. Conjugation Of Chimeric Antibody To DTPA

The Z2D3 chimeric antibody or its F(ab')$_2$ or Fab fragment, was dialyzed extensively against 100 mM HEPES [4-(2-Hydroxyethyl)-1-piperazineethanesulfonic acid] (U.S. Biochemical Corp.), 150 mM sodium chloride, pH 7.5. Diethylenetriaminepentaacetic acid (DTPA) anhydride (Sigma) was suspended in dry chloroform at a concentration of 2 mg/mL. The desired quantity of suspended DTPA-anhydride, usually a 25-fold molar excess over the amount of antibody being conjugated, was transferred to a glass tube. The chloroform was evaporated under a stream of dry argon gas. The dialyzed antibody was added to the DTPA-anhydride residue in the tube and thoroughly mixed. The mixture was incubated at 0° C. for 45 minutes with occasional stirring. Unbound DTPA was removed by extensive dialysis, and the conjugated antibody was stored at 4° C.

VI-2. In-Vivo Nuclear Imaging Of Atherosclerotic Rabbit

DTPA-Z2D3 F(ab')$_2$, prepared as in section VII-1 (0.25 mg in 0.15 mL), was mixed with 1 mCi indium-111 chloride in 0.15 mL of 1M citrate buffer, pH 5.5. The reaction mixture was incubated at ambient temperature for 30 minutes, and the indium-labeled antibody fragment was separated from unbound indium by gel filtration on a Sephadex G-25 (Sigma) column in 0.15M sodium chloride.

Z2D3 chimeric F(ab')$_2$ fragment labeled with Indium-III (~0.5 mCi/0. 5 mg) was used to image experimental atheroma in rabbits (n=4) with de-endothelialized descending aorta, fed on 6% peanut oil, 2% cholesterol chow for 8–12 weeks. Uptake was compared to control human IgG1 F(ab')$_2$, prepared from human myeloma IgG (Calbiochem, San Diego, Calif.), using the procedures developed for the chimeric Z2D3 antibody (section V-9).

Atherosclerotic lesions were visualized in 3 out of 4 rabbits with the chimeric Z2D3 F(ab')$_2$-DTPA. (One rabbit had minimal lesions.) Lesions were not visualized in rabbits injected with the control human IgG1 F(ab')$_2$. Mean % injected dose per gram in the lesions was as follows:

| Sample | % Injected Dose/Gram (± SD) | |
| --- | --- | --- |
| | Normal Artery | Lesion |
| Chimeric Z2D3 F(ab')$_2$ | 0.019 ± 0.006 | 0.112 ± 0.049 |
| Human IgG1 F(ab')$_2$ | 0.005 | 0.036 |

The uptake of the chimeric F(ab')$_2$ was significantly higher than the control and specific targeting was also demonstrated by macro-autoradiography.

VII-3 Other Imaging Techniques

The use of the Z2D3 monoclonal antibody or immunologically active fragments thereof conjugated to DTPA is not limited to radio imaging with indium-111. A wide variety of radioisotopes may be incorporated into the DTPA moieties. In addition, other chelating agents may be conjugated to the antibody.

Furthermore, Z2D3 monoclonal antibodies conjugated to chelating agents is not limited to use with radioisotopes. Paramagnetic ions may be incorporated for use with Magnetic Resonance Imaging (MRI). X-ray opaque ions could be used for X-ray imaging.

In principle, chelator conjugated Z2D3 monoclonal antibodies could be used to image atherosclerotic plaque using any imaging technology, whether presently available or to be developed in the future, which exploits the presence of a metal ion or ions as a means of detection.

VIII. Treatment Of Atherosclerotic Plaque

As noted in section VII, the Z2D3 monoclonal antibody provides a means of delivering an agent directly to the site of an atherosclerotic lesion in vivo. Such an agent could be therapeutic in nature. Any agent which would serve to dissolve, digest, break up or inhibit the growth of atherosclerotic plaque or otherwise ameliorate the progression of atherosclerosis could be used. Some methods are presented below.

VIII-1. Laser Angioplasty Ablation Of Atherosclerotic Plaque

The use and limitations of lasers in angioplasty have been discussed above (Background Of The Invention). The Z2D3 monoclonal antibody can be conjugated to a dye whose absorption maximum corresponds to the maximum emission wavelength of the laser to be used for angioplasty. The Z2D3 antibody and the conjugated dye would bind to the plaque and not to normal tissues. During the ablation procedure, energy from the laser would be absorbed by the dye and thus be concentrated on the diseased areas. As a consequence, the efficiency of ablation would be increased while minimizing damage to surrounding normal tissues.

A wide variety of dyes fluorescent, are available for conjugation to proteins. A number of methods for conjugating dyes to proteins, and in particular antibodies, have been published. The choice of dye and method of conjugation would be readily apparent to one skilled in the arts of laser angioplasty and protein chemistry.

One dye which may be useful in laser angioplasty is rhodamine. Rhodamine is a fluorescent dye whose various derivatives absorb light at a wavelength of approximately 570 nm. In a preliminary study the Z2D3 antibody has been conjugated to lissamine rhodamine B.

VIII-1(a) Conjugation Of Chimeric Antibody To Rhodamine

The chimeric Z2D3 antibody or it F(ab')$_2$ or Fab fragment at a concentration of 2–4 mL was dialyzed against 50 mM sodium borate buffer, pH 8.2. A fresh solution of lissamine rhodamine B sulfonyl chloride (Molecular Probes, Inc. Eugene, Oreg.) was prepared in dry acetone at 0.25 mg/mL. An aliquot of this solution representing a 6-fold molar excess of rhodamine over the amount of antibody to be conjugated was transferred to a glass tube. The acetone was evaporated under a stream of dry argon. The dialyzed antibody was added to the rhodamine residue in the tube. The tube was capped, covered with aluminum foil, and incubated at 4° C. for 3 hours with constant shaking.

An aliquot of a 1.5M hydroxylamine hydrochloride (Sigma) solution (pH 8.0) equal to ¹/₁₀ the volume of the antibody solution was added to the reaction mixture. This solution was incubated at 4° C. for 30 minutes with constant shaking. The reaction mixture was then dialyzed extensively against borate buffer in the dark. The rhodamine-antibody conjugate was stored at 4° C. in the dark to avoid photobleaching of the dye.

VIII-1(b) Enhancement Of Laser Angioplasty Ablation With Antibody-Rhodamine Conjugate Frozen sections of rabbit atherosclerotic aortae stained with the rhodamine-chimeric F(ab')$_2$ demonstrated intense fluorescent staining confined to the diseased intima of atherosclerotic arteries while control arteries were entirely negative. Isolated aortae segments or rings exposed to rhodamine-F(ab')$_2$ demonstrated immunofluorescent staining of the luminal portion of the thickened intima during 1–24 hours of exposure. Thus, the Z2D3 antibody specifically delivers the dye to atherosclerotic lesions and not to normal tissues. With further development this approach of selectively labeling atherosclerotic lesions with dye-conjugated antibodies may allow the ablation of diseased areas by laser while minimizing damage to normal tissue.

VIII-2 Enzymatic Digestion Of Atherosclerotic Plaque

The Z2D3 monoclonal antibody could be used to deliver enzymes specifically to the site of an atherosclerotic lesion. The enzyme could be any enzyme capable of digesting one or more components of the plaque. The enzyme or a combination of enzymes would be conjugated to the antibody by one of a variety of conjugation techniques known to one skilled in the art of protein chemistry.

In another approach, the Z2D3 antibody could be coupled to an inactive form of an enzyme, for example, a proenzyme or an enzyme-inhibitor complex. The advantage of this method would be that larger amounts of enzyme could be administered, thus delivering larger amounts of enzyme to the plaque while not causing any damage to normal tissues by the circulating conjugate. After the conjugate has bound to the plaque and unbound circulating conjugate has cleared, the enzyme could be activated so as to begin digestion of the plaque. Activation would involve specific cleavage of the proenzyme or removal of an enzyme inhibitor.

VIII-3 Drug Delivery By The Z2D3 Monoclonal Antibody

The Z2D3 monoclonal antibody could be conjugated to a variety of drugs useful in treating atherosclerosis. Of particular interest would be drugs which inhibit cell growth or which inhibit cell growth factors. The Z2D3 monoclonal antibody would specifically deliver a high concentration of the drug of choice directly to the atherosclerotic lesion.

VIII-4 Drugs Which Inhibit Or Prevent The Formation Of The Z2D3 Antigen Epitope The Z2D3 monoclonal antibody binds to all stages of atherosclerotic plaque development as visualized by immunohistology (Section III). It is therefore likely that the Z2D3 antigen is an integral component of the atherosclerotic lesion.

Any compound or drug which inhibits or prevents the synthesis or formation of the Z2D3 atherosclerotic plaque-specific antigen may serve to inhibit, prevent or cure the disease. The formation of plaque antigen could be blocked in several ways. In one method, antigen formation could be blocked by inhibiting or inactivating the enzyme or enzymes responsible for the synthesis of the Z2D3 antigen.

Evidence presented above (section IV) suggests that the Z2D3 antigen is a complex comprised of at least two molecules, one of which is a steroid, and the other, a quaternary ammonium salt. Consequently, a second method of preventing plaque antigen formation would be the administration of a drug which blocks the formation of the antigen complex or which forms non-antigenic complexes with one or both of the antigen components.

VIII-4-(a). Inhibition Of The Surrogate Antigen ELISA

While studying the surrogate antigen ELISA (Section IV-2), it was discovered that certain chemical compounds, which, when added to the plate coating solution (Section IV-2-(e)), significantly reduce or completely eliminate the ELISA signal. Since these chemical compounds do not function as surrogate antigens, either alone or in combination with a suitable steroid or quaternary ammonium compound, this inhibition of the ELISA is not due to competition for antibody binding. Inhibition of the ELISA is therefore attributed to the chemical's ability to block or inhibit the formation of the surrogate antigen. Thus, such chemicals could be of therapeutic value in the treatment of atherosclerosis.

Materials

Reagents and materials for ELISA assays were as presented in Section IV-2-(d) and (e). Chemicals being tested as inhibitors, the highest grade available, were purchased from one of the following: Sigma Chemical Company, St. Louis, Mo.; Aldrich Chemical Company, Milwaukee, Wis.; or Steraloids, Inc., Wilton, N.H. Compounds were stored as directed by the supplier, generally desiccated over phosphorous pentoxide.

Procedure

A surrogate antigen solution containing 0.5 mg/mL of the steroid of choice and 31.25 µg/mL of the quaternary ammonium compound of choice was prepared in absolute ethanol. This solution was pipetted into microtiter plate wells, 50 µL per well, yielding 25 µg of steroid and 1.56 µg of quaternary ammonium compound per well. Negative control wells received no antigen solution.

Chemicals being tested as inhibitors were dissolved in absolute ethanol at 0.5 mg/mL. In some cases, sonication was required for complete dissolution. A two-fold dilution series of the chemical was prepared in absolute ethanol. Aliquots, 50 µL per well, of the inhibitor at the appropriate dilutions were added to the microtiter plate wells containing the surrogate antigen solution. Positive control wells received no inhibitor. After all compounds were added to the wells, the ethanol was removed by evaporation in a stream of air. The remainder of the ELISA was performed as described in Section IV-2-(d).

Results

The chemical compounds which have been tested to-date for their ability to inhibit the Z2D3 surrogate antigen are shown in Table 6. Several compounds are potent inhibitors, requiring 5 nmol or less of the compound per well to reduce ELISA activity by 50%. Several of these compounds will be tested for their ability to inhibit the formation of atherosclerotic lesions in-vivo.

Of the weak inhibitors, requiring more than 5 nmol of compound for 50% inhibition, phosphatidylcholine is of interest. Intravenous injection of phosphatidylcholine have been reported to cause the regression of atherosclerotic lesions in animal models [Byers, S. O. and Friedman, M., Journal Lipid Research, vol. 1 (4), pages 343–348, 1960; Stafford, W. W. and Day, C. E., Artery, vol. 1(2), pages 106–114, 1975]. The mechanism of this action has not been explained. It is possible that phosphatidylcholine functions as an inhibitor of the Z2D3 antigen.

Table 1. Immunohistological Specificity Of Z2D3 IgM-Class Monoclonal Antibody.

Table 2. Sterol Or Sterol-Like Components—ELISA Activity Relative To Cholesterol.

Table 3. Quaternary Ammonium Or Non-Sterol Component—ELISA Activity Relative To BAC.

Table 4. PCR And cDNA Primers.

Table 5. Immunohistological Specificity Of Z2D3 Chimeric Antibody.

Table 6. Chemicals Tested As Inhibitors Of The Z2D3 Surrogate Antigen ELISA

TABLE 1

Immunohistologic Screening

We have demonstrated that Mab Z2D3 is localized to the core of atherosclerotic plaque. It does not bind other arterial wall components or other tissues that would interfere with its use as an in-vivo targeting agent. The table below shows that the S2D3 antigen is extracellulsar in the atherosclerosis lesions (that is, it is exposed) and is available for binding to its antibody. The antigen is present in three other sites (spleen, ovary, and lymph node) intracellularly (that is, it is not exposed), and will not be available for binding in vivo.

| Tissue | Staining |
|---|---|
| Cerebellum | — |
| Cerebral cortex | — |
| Medulla | — |
| Spinal cord | — |
| Dura | — |
| Peripheral nerve | — |
| Heart | — |
| Lung | — |
| Trachea | — |
| Bronchus | — |
| Breast | — |
| Pectoral muscle | — |
| Esophagus | — |
| Diaphragm | — |
| Stomach | — |
| Liver | — |
| Spleen | 3-4[+] fibromyocytes (intracellular) |
| Pancreas | — |
| Small bowel | — |
| Colon | — |
| Ovary | 1-2[+] luteal cells (intracellular) |
| Uterus | — |
| Kidney | — |
| Bladder | — |
| Rectum | — |
| Psoas Muscle | — |
| Lymph Node | — |
| Skin | 1-3[+] sebaceous glands (intracellular) |
| Coronary artery lesion | 3-4[+] extracellular straining |

TABLE 2

Sterol Or Sterol - Like Component ELISA Activity Relative To Cholesterol

| Compound | Quaternary Ammonium Component | | |
|---|---|---|---|
| | Benzalkonium Chloride | Benzyldimethyl Hexadecyl Ammonium Chloride | Palmitoyl Choline |
| Highly Active Compounds | | | |
| 5-Cholesten-3β-ol (Cholesterol) | 1 | 1 | 1 |
| 5,7-Cholestadien-3β-ol (7-Dehydrocholesterol) | 2 | 4 | 8 |
| 5,24-Cholestadien-3β-ol (Desmosterol) | 1 | 1 | 1 |
| 5α-Cholestane-3β-ol (Dihydrocholesterol) | 1 | 1 | 1 |
| 5α-Cholest-7-en-3β-ol (Lathosterol) | nt | 1 | 1 |
| 5-Cholesten-3-one | nt | 0.1 | 2 |
| Other Steroid Compounds | | | |
| 5β-Cholanic acid | <0.05 | nt | nt |
| Cholecalciferol (Vitamin D3) | nt | <0.05 | <0.05 |
| 5α-Cholestane | <0.05 | nt | nt |
| 5β-Cholestane 3β-ol sulfate | <0.05 | nt | nt |
| 5β-Cholestane-3β-ol (Corpostanol) | <0.05 | <0.05 | 0.1 |
| 5β-Cholestane-3-one | <0.05 | nt | nt |
| 4-Cholesten-3α-ol | <0.05 | nt | nt |
| 4-Cholesten-3β-ol (Allocholesterol) | 0.5 | nt | nt |
| 4-Cholesten-3-one | nt | <0.05 | <0.05 |
| 5-Cholesten | nt | <0.05 | <0.05 |
| 5-Cholesten-3β,7α-diol (7α-Hydroxycholesterol) | nt | 0.1 | 0.3 |
| 5-Cholesten-3β,7β-diol (7β-Hydroxycholesterol) | nt | <0.05 | <0.05 |
| 5-Cholesten-3β,19-diol (19-Hydroxycholesterol) | 0.1 | nt | nt |
| 5-Cholesten-3β,20α-diol (20α-Hydroxycholesterol) | nt | <0.05 | <0.05 |
| 5-Cholesten-3β,25-diol (25-Hydroxycholesterol) | <0.05 | nt | nt |
| 5-Cholesten-3α-ol (Epicholesterol) | <0.05 | nt | nt |
| 5-Cholesten-3β-ol acetate | <0.05 | nt | nt |
| 5-Cholesten-3β-ol benzoate | <0.05 | nt | nt |
| 5-Cholesten-3β-ol n-butyrate | <0.05 | nt | nt |
| 5-Cholesten-3β-ol ethyl carbonate | <0.05 | nt | nt |
| 5-Cholesten-3β-ol n-palmitate | <0.05 | nt | nt |
| Dihydrotachysterol | <0.05 | nt | nt |
| 3-Hydroxyandrost-5-en-17-one | <0.05 | nt | nt |
| 8,24-Lanostadien-3β-ol (Lanosterol) | 0.1 | 0.1 | 0.1 |
| 5,22 Stigmastadien-3β-ol (Stigmasterol) | <0.05 | nt | nt |
| Tryclycerides: | | | |
| Trilaurin | <0.05 | nt | nt |
| Trimyristin | <0.05 | nt | nt |
| Other Compounds: | | | |
| Decahydro-2-naphthol | <0.05 | nt | nt |
| 1,12-Dodecanediol | <0.05 | nt | nt |
| n-Dodecanoic acid | <0.05 | nt | nt |
| Non-Mammalian Sterols: | | | |
| Spirosol-5-en-3β-ol (Solsodine) | <0.05 | nt | nt |
| (25R) Sprost-5-en-3β-ol (Diosgenin) | 0.2 | nt | nt |
| 5,24 (28)-Sitmastadien-3β-ol (Fucosterol) | 1 | nt | nt |

TABLE 3

Quaternary Ammonium Or Non-Sterol Component ELISA Activity Relative to BAC

| Compound | Steroid Component | |
|---|---|---|
| | Cholesterol | 7-Dehydro-cholesterol |
| Quaternary Ammonium Detergents: | | |
| Benzalkonium chloride | 1 | 1 |
| Dodecyltrimethyl ammonium bromide | <0.05 | <0.05 |
| Tetradecyltrimethyl ammonium bromide | <0.05 | 0.1 |
| Hexadecyltrimethyl ammonium bromide | 1 | 1 |
| Benzyldimethyldodecyl ammonium bromide | 0.1 | 0.1 |
| Benzyldimethyltetradecyl ammonium chloride | 1 | 4 |
| Benzyldimethylhexadecyl ammonium chloride | 12 | 8 |
| Benzyldimethyloctadecyl ammonium chloride | 16 | 8 |
| Benzyltrimethyl ammonium chloride | <0.05 | nt |
| Benzyltriethyl ammonium chloride | <0.05 | nt |
| Benzyltributyl ammonium chloride | <0.05 | nt |
| Didodecyldimethyl ammonium chloride | 0.1 | 0.5 |
| Hexadecyldimethylethyl ammonium chloride | 4 | 4 |
| Hexadecylpyridyl ammonium chloride | 2 | 4 |
| Naturally Occurring Quaternary Ammonium Compounds: | | |
| Butyryl choline | <0.05 | <0.05 |
| Lauroyl choline | <0.05 | 0.2 |
| Myristoyl choline | <0.05 | 2 |
| Palmitoyl choline | 0.2 | 4 |
| Stearoyl choline | 0.2 | 4 |
| Palmitoyl carnitine | <0.05 | <0.05 |
| n-Palmitoyl-D-sphingomyelin | <0.05 | <0.05 |
| Phosphatidyl choline, hen's egg | <0.05 | <0.05 |
| Phosphatidyl choline, hen's egg, reduced | <0.05 | <0.05 |
| Phosphatidyl choline, Dipalmitoyl | <0.05 | <0.05 |
| Phosphatidyl choline, 1-Palmitoyl, 2-Acetyl | <0.05 | <0.05 |
| 1-0-Hexadecyl-2-acetyl-sn-Glycero-3-phospho-(N,N,N-trimethyl)hexanolamine | <0.05 | 0.1 |
| Other Compounds: | | |
| Polyethylene glycol | <0.05 | <0.05 |
| Polyvinyl alcohol | <0.05 | <0.05 |

TABLE 4

PCR And cDNA Primers
Restriction Sites Are Underlined

| | |
|---|---|
| CK2FOR 5' | GG<u>AAGCTT</u>GAAGATGGATACAGTTGGTGCAGC |
| CM1FOR 5' | GG<u>AAGCTT</u>AAGACATTTGGGAAGGACTGACTCTC |
| VH1BACK 5' | AGGTSMAR<u>CTGCAG</u>SAGTCWGG |
| VH1FOR 5' | TGAGGAGAC<u>GGTG</u>ACCGTGGTCCCTTGGCCCCAG |
| VK1BACK 5' | GACATT<u>CAGCTG</u>ACCCAGTCTCCA |
| VK4BACK 5' | GACATT<u>GAGCTC</u>ACCCAGTCTCCA |
| VK1FOR 5' | GTTAG<u>ATCT</u>CCAGCTTGGTCCC |
| VK2FOR 5' | GTTAG<u>ATCTGAG</u>CTTGGTCCC |

Sequence CK2FOR 5' is SEQ ID NO:81.
Sequence CM1FOR 5' is SEQ ID NO:82.
Sequence VH1BACK 5' is SEQ ID NO:83.
Sequence VH1FOR 5' is SEQ ID NO:84.
Sequence VK1BACK 5' is SEQ ID NO:85.
Sequence VK4BACK 5' is SEQ ID NO:86.
Sequence VK1FOR 5' is SEQ ID NO:87.
Sequence VK2FOR 5' is SEQ ID NO:88.

TABLE 5

Immunohistologic Screening
We have demonstrated that the chimeric Z2D3 IgG antibody is localized to the core of atherosclerotic plaque. It does not bind other arterial wall components or other tissues taht would interfere with its use as an in-vivo targeting agent. The table below shows that the Z2D3 antigen is specific to the atherosclerosis lesions only, and is not present in any other sites.

| Tissue | Staining |
|---|---|
| Coronary artery lesion | 3-4+ extracellular staining |
| Cerebellum | — |
| Cerebral cortex | — |
| Medulla | — |
| Spinal cord | — |
| Dura | — |
| Peripheral nerve | — |
| Heart | — |
| Lung | — |
| Trachea | — |
| Bronchus | — |
| Breast | — |
| Pectoral muscle | — |
| Esophagus | — |
| Diaphragm | — |
| Stomach | — |
| Liver | — |
| Spleen | — |
| Pancreas | — |
| Small bowel | — |
| Colon | — |
| Ovary | — |
| Uterus | — |
| Kidney | — |
| Bladder | — |
| Rectum | — |
| Psoas muscle | — |
| Lymph node | — |
| Skin | — |

Table 6.

Chemicals Tested As Inhibitors Of The Z2D3 Surrogate Antigen ELISA

Strong Inhibitors: Less than 5 nmol of the compound yields 50% inhibition of the ELISA activity:

5β-Cholanic Acid
Arachidonic Acid
Cardiolipin
5α-Cholestane-β-ol Sulfate
Lysophosphatidylcholine
Palmitic Acid
Phosphatidyl-N,N-Dimethylethanolamine
Phosphatidylethanolamine Phosphatidylglycerol
Stearic Acid
Weak Inhibitors: Greater than 5 nmol of the compound required to yield 50% inhibition of the ELISA activity:
Clofibric Acid
Eicosapentaenoic Acid
Phosphatidylinositol
Sodium Dodecylsulfate
Sphingomyelin
Sulfatides
Tween-20
Non-Inhibitors: 50 nmol of the compound yields no inhibition of the ELISA activity:
5α-Androstan-3α-ol-17-one Sulfate 5α-Androstan-3β-ol-17-one Sulfate
5α-Androstan-17β-ol-3-one Sulfate
5β-Androstan-3α-ol-17-one Sulfate
5-Androsten-3β-ol-17-one Sulfate
Table 6, Continued
Bezafibrate
Danazol
Hexadecanedioic Acid
Probucol
Triglycerides
Triton X-100
Triton X-405

---

What is claimed is:

1. A proteinaceous construct capable of specifically binding to atherosclerotic plague comprising a binding site which comprises an amino acid sequence or combination of amino acid sequences, each of which amino acid sequences is the same or substantially the same as the amino acid sequence of a complementarity determining region (CDR) of a murine-human chimeric monoclonal antibody produced by a rat myeloma cell line designated Z2D3 73/30 1D10.

2. The proteinaceous construct of claim 1, labeled with a detectable marker.

3. The proteinaceous construct of claim 1 bound to a solid support.

4. A reagent for use in imaging atherosclerotic plaque, which comprises the proteinaceous construct of claim 2, in an amount effective to image atherosclerotic plaque, and a physiologically acceptable carrier.

5. A method for imaging atherosclerotic plaque, which comprises:

(a) contacting the atherosclerotic plaque to be imaged with the reagent of claim 4, under conditions such that the reagent binds to the atherosclerotic plaque; and (b) detecting the detectable marker labelling the proteinaceous construct in the reagent bound to the atherosclerotic plaque;

thereby imaging the atherosclerotic plaque.

6. The proteinaceous construct of claim 1, bound to a chromophore capable of absorbing radiation having a plaque ablating wavelength.

7. The proteinaceous construct of claim 6, wherein the chromophore absorbs light having a wavelength from about 190 nm to about 1100 nm.

8. The proteinaceous construct of claim 7, wherein the chromophore is fluorescein, rhodamine, tetracycline, hematoporphyrin, or β-carotene.

9. A reagent for ablating atherosclerotic plaque comprising the proteinaceous construct of claim 6 in an amount effective to highlight the atherosclerotic plaque to be ablated, and a physiologically acceptable carrier.

10. A method for ablating atherosclerotic plaque, which comprises:

(a) contacting atherosclerotic plaque with an effective amount of the reagent of claim 9, so that the proteinaceous construct present in the reagent binds to the atherosclerotic plaque forming an atherosclerotic plaque-construct complex;

(b) exposing the resulting complex to radiation having a plaque ablating wavelength under conditions such that the radiation is absorbed by the chromophore at a sufficient energy to ablate the atherosclerotic plaque; and (c) thereby ablating the atherosclerotic plaque.

11. A method for detecting in a sample an antigen indicative of the presence of atherosclerotic plaque, which comprises:

(a) contacting the sample with the proteinaceous construct of claim 1, under conditions such that the proteinaceous construct binds to the antigen in the sample to form a detectable complex;

(b) detecting the complex so formed; and (c) thereby detecting in the sample an antigen indicative of the presence of atherosclerotic plaque.

12. A method for quantitatively determining in a sample the concentration of an antigen indicative of the presence of atherosclerotic plaque, which comprises:

(a) contacting a solid support with an excess of the proteinaceous construct of claim 1, under conditions permitting the construct to attach to the surface of the solid support;

(b) removing unbound proteinaceous construct;

(c) contacting the resulting solid support to which the proteinaceous construct is bound with the sample under conditions such that any antigen present in the sample binds to the bound construct and forms a complex therewith;

(d) removing any antigen which is not bound to the complex;

(e) contacting any complex so formed with an excess of a detectable reagent which specifically binds to any antigen present in the complex so as to form a second complex which includes the proteinaceous construct, the antigen, and the detectable reagent;

(f) removing any detectable reagent which is not bound in the second complex;

(g) quantitatively determining the concentration of detectable reagent present in the second complex; and (h) thereby quantitatively determining in the sample the concentration of an antigen indicative of the presence of atherosclerotic plaque.

13. The method of claim 12, wherein the detectable reagent comprises a monoclonal antibody or fragment thereof labeled with a detectable marker, wherein the monoclonal antibody is produced by hybridoma Z2D3 having ATCC Accession Number HB9840, hybridoma Z2D3/3E5 having ATCC Accession Number HB10485, rat myeloma cell line Z2D3 73/30 1D10 having ATCC Accession Number CRL 11203, or a CDR-grafted antibody comprising a CDR region from hybridoma Z2D3 or hybridoma Z2D3/3E5 and a framework and constant region from a human immunoglobulin.

14. A method for quantitatively determining in a sample the concentration of an antigen which is indicative of the presence of atherosclerotic plaque, which comprises:

(a) contacting a solid support with a predetermined amount of the proteinaceous construct of claim 1, under conditions permitting the construct to attach to the surface of the solid support;

(b) removing any proteinaceous construct not bound to the solid support;

(c) contacting the resulting solid support to which the construct is bound with a predetermined amount of an antigen labeled with a detectable marker, and with the sample under such conditions that labeled and sample antigens competitively bind to the construct bound to the solid support and form a complex therewith;

(d) removing any labeled and sample antigens which are not bound to the complex;

(e) quantitatively determining the amount of labeled antigen bound to the solid support; and (f) thereby quantitatively determining in the sample the concentration of an antigen which is indicative of the presence of atherosclerotic plaque.

15. The method of claim 14, wherein step (e) comprises quantitatively determining the amount of labeled antigen not bound to the solid support.

16. A method for quantitatively determining in a sample the concentration of an antigen which is indicative of the presence of atherosclerotic plaque, which comprises:

(a) contacting a solid support with a predetermined amount of the proteinaceous construct of claim 1, under conditions permitting the construct to attach to the surface of the support;

(b) removing any proteinaceous construct not bound to the solid support;

(c) contacting the resulting solid support to which the construct is bound with the sample under conditions such that any antigen present in the sample binds to the bound construct and forms a complex therewith;

(d) removing any antigen which is not bound to the complex;

(e) contacting the complex so formed with a predetermined amount of plaque antigen labeled with a detectable marker under conditions such that the labeled plaque antigen competes with the antigen from the sample for binding to the construct;

(f) removing any labeled and sample antigens which are not bound to the complex;

(g) quantitatively determining the amount of labeled plaque antigen bound to the solid support; and (h) thereby quantitatively determining in the sample the concentration of an antigen which is indicative of the presence of atherosclerotic plaque.

17. The method of claim 16, wherein step (g) comprises quantitatively determining the amount of labeled antigen not bound to the solid support.

18. The proteinaceous construct of claim 1, conjugated to an enzyme capable of digesting a component of atherosclerotic plaque.

19. The proteinaceous construct of claim 18, wherein the enzyme is a proenzyme which, when activated, is converted to an enzyme capable of digesting a component of atherosclerotic plaque.

20. The proteinaceous construct of claim 18, wherein the construct and the enzyme comprise a single molecule.

21. The proteinaceous construct of claim 18, wherein the construct is a bifunctional peptide comprising a binding site specific for the enzyme and a binding site specific for the antigen.

22. The proteinaceous construct of claim 18, wherein the enzyme is a proteinase, an elastase, a collagenase, or a saccharidase.

23. The proteinaceous construct of claim 19, wherein the proenzyme is a proenzyme form of fibroblastic collagenase, gelatinase, polymorphonuclear collagenase, granolocytic collagenase, stromelysin I, stromelysin II, or elastase.

24. A method for reducing the amount of atherosclerotic plaque in a blood vessel, which comprises:
  (a) contacting the atherosclerotic plaque with a reagent comprising the proteinaceous construct of claim 18 under conditions and in an amount such that the reagent binds to, and digests, a component of the plaque; and
  (b) thereby reducing the amount of atherosclerotic plaque in a blood vessel.

25. A reagent comprising the proteinaceous construct of claim 18, in an amount effective to digest a component of atherosclerotic plaque, and a physiologically acceptable carrier.

26. The proteinaceous construct of claim 1, conjugated to cell growth inhibitors capable of preventing proliferation of atherosclerotic plaque.

27. A pharmaceutical composition for treating atherosclerosis, which comprises the proteinaceous construct of claim 1 bound to a drug useful in treating atherosclerosis.

28. A method of treating atherosclerosis in a subject, which comprises administering to the subject an amount of the pharmaceutical composition of claim 27 effective to treat atherosclerosis.

* * * * *

SEQUENCE LISTING ( 1 ) GENERAL INFORMATION:

( i i i ) NUMBER OF SEQUENCES: 88

( 2 ) INFORMATION FOR SEQ ID NO:1:

( i ) SEQUENCE CHARACTERISTICS:
  ( A ) LENGTH: 22 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:1:

AGGTSMARCT GCAGSAGTCW GG  22

( 2 ) INFORMATION FOR SEQ ID NO:2:

( i ) SEQUENCE CHARACTERISTICS:
  ( A ) LENGTH: 220 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:2:

CTGCAGGAGT CWGGAGGAGG CTTGGTGCAA CCTGGGGGGT CACGGGACT CTCTTGTGAA  60

GGCTCAGGGT TTACTTTTAG TGGCTTCTGG ATGAGCTGGG TTCGACAGAC ACCTGGGAAG  120

ACCCTGGAGT GGATTGGAGA CATTAATTCT GATGGCAGTG CAATAAACTA CGCACCATCC  180

ATAAAGGATC GATTCACTAT CTTCAGAGAC AATGACAAGA  220

( 2 ) INFORMATION FOR SEQ ID NO:3:

( i ) SEQUENCE CHARACTERISTICS:
  ( A ) LENGTH: 218 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:3:

| | | | | | | |
|---|---|---|---|---|---|---|
| CTGCAGGAGT | CWGGAGGAGG | CTTGGTGCAA | CCTGGGGGGT | CACGGGGACT | CTCTTGTGAA | 6 0 |
| GGCTCAGGGT | TTACTTTTAG | TGGCTTCTGG | ATGAGCTGGG | TTCGACAGAC | ACCTGGGAAG | 1 2 0 |
| ACCCTGGAGT | GGATTGGAGA | CATTAATTCT | GATGGCAGTG | CAATAAACTA | CGCACCATCC | 1 8 0 |
| ATAAAGGATC | GATTCACTAT | CTTCAGAGAC | AATGACAA | | | 2 1 8 |

( 2 ) INFORMATION FOR SEQ ID NO:4:

( i ) SEQUENCE CHARACTERISTICS:
        ( A ) LENGTH: 220 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:4:

| | | | | | | |
|---|---|---|---|---|---|---|
| CTGCAGGAGT | CTGGAGGAGG | CTTGGTGCAA | CCTGGGGGGT | CGCGGGGACT | CTCTTGTGAA | 6 0 |
| GGCTCAGGGC | TTACTTTTAG | TGGCTTCTGG | ATGAGCTGGG | TTCGACAGAC | ACCTGGGAAG | 1 2 0 |
| ACCCTGGAGT | GGATTGGAGA | CATTAATTCT | GATGGCAGTG | CAATAAACTA | CGCACCATCC | 1 8 0 |
| ATAAAGGATC | GATTCACTAT | CTTCAGAGAC | AATGACAAGA | | | 2 2 0 |

( 2 ) INFORMATION FOR SEQ ID NO:5:

( i ) SEQUENCE CHARACTERISTICS:
        ( A ) LENGTH: 218 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:5:

| | | | | | | |
|---|---|---|---|---|---|---|
| CTGCAGGAGT | CAGGAGGAGG | CTTGGTGCAA | CCTGGGGGGT | CACGGGGACT | CTCTTGTGAA | 6 0 |
| GGCTCAGGGT | TTACTTTTAG | TGGCTTCTGG | ATGAGCTGGG | TTCGACAGAC | ACCTGGGAAG | 1 2 0 |
| ACCCTGGAGT | GGATTGGAGA | CATTAATTCT | GATGGCAGTG | CAATAAACTA | CGCACCATCC | 1 8 0 |
| ATAAAGGATC | GATTCACTAT | CTTCAGAGAC | AATGACAA | | | 2 1 8 |

( 2 ) INFORMATION FOR SEQ ID NO:6:

( i ) SEQUENCE CHARACTERISTICS:
        ( A ) LENGTH: 237 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:6:

| | | | | | |
|---|---|---|---|---|---|
| CTGCAGGAGT | CAGGAGGAGG | CTTGGTGCAA | CCTGGGGGGT | CACGGGGACT | CTCTTGTGAA | 60
| GGCTCAGGGT | TTACTTTTAG | TGGCTTCTGG | ATGAGCTGGG | TTCGACAGAC | ACCTGGGAAG | 120
| ACCCTGGAGT | GGATTGGAGA | CACTAATTCT | GATGGCAGTG | CAATAAACTA | CGCACCATCC | 180
| ATAAAGGATC | GATTCACTAT | CTTCAGAGAC | AATGACAAGA | GCACCCTGTA | CCTGCAG | 237

( 2 ) INFORMATION FOR SEQ ID NO:7:

( i ) SEQUENCE CHARACTERISTICS:
  ( A ) LENGTH: 220 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:7:

| | | | | | |
|---|---|---|---|---|---|
| AGGCTTGGTG | CAACCTGGGG | GGTCACGGGG | ACTCTCTTGT | GAAGGCTCAG | GGTTTACTTT | 60
| TAGTGGCTTC | TGGATGAGCT | GGGTTCGACA | GACACCTGGG | AAGACCCTGG | AGTGGATTGG | 120
| AGACATTAAT | TCTGATGGCA | GTGCAATAAA | CTACGCACCA | TCCATAAAGG | ATCGATTCAC | 180
| TATCTTCAGA | GACAATGACA | AGAGCACCCT | GTACCTGCAG | | | 220

( 2 ) INFORMATION FOR SEQ ID NO:8:

( i ) SEQUENCE CHARACTERISTICS:
  ( A ) LENGTH: 220 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:8:

| | | | | | |
|---|---|---|---|---|---|
| AGGCTTGGTG | CAACCTGGGG | GGTCACGGGG | ACTCTCTTGT | GAAGGCTCAG | GGTTTACTTT | 60
| TAGTGGCTTC | TGGATGAGCT | GGGTTCGACA | GACACCTGGG | AAGACCCTGG | AGTGGATTGG | 120
| AGACATTAAT | TCTGATGGCA | GTGCAATAAA | CTACGCACCA | TCCATAAAGG | ATCGATTCAC | 180
| TATCTTCAGA | GACAGTGACA | AGAGCACCCT | GTACCTGCAG | | | 220

( 2 ) INFORMATION FOR SEQ ID NO:9:

( i ) SEQUENCE CHARACTERISTICS:
  ( A ) LENGTH: 220 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:9:

| | | | | | |
|---|---|---|---|---|---|
| AGGCTTGGTG | CAACCTGGGG | GGTCACGGGG | ACTCTCTTGT | GAAGGCTCAG | GGTTTACTTT | 60

```
TAGTGGCTTC TGGATGAGCT GGGTTCGACA GACACCTGGG AAGACCCTGG AGTGGATTGG        120

AGACATTAAT TCTGATGGCA GTGCAATAAA CTACGCACCA TCCATAAAGG ATCGATTCAC        180

TATCTTCAGA GACAATGACA AGAGCACCCT GTACCTGCAG                              220
```

( 2 ) INFORMATION FOR SEQ ID NO:10:

( i ) SEQUENCE CHARACTERISTICS:
        ( A ) LENGTH: 219 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:10:

```
GGCTTGGTGC AACCTGGGGG GTCACGGGGA CTCTCTTGTG AAGGCTCAGG GTTTACTTTT        60

AGTGGCTTCT GGATGAGCTG GGTTCGACAG ACACCTGGGA AGACCCTGGA GTGGATTGGA       120

GACATTAATT CTGATGGCAG TGCAATAAAC TACGCACCAT CCATAAAGGA TCGATTCACT       180

ATCTTCAGAG ACAATGACAA GAGCACCCTG TACCTGCAG                             219
```

( 2 ) INFORMATION FOR SEQ ID NO:11:

( i ) SEQUENCE CHARACTERISTICS:
        ( A ) LENGTH: 218 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:11:

```
GCTTGGTGCA ACCTGGGGGG TCACGGGGAC TCTCTTGTGA AGGCTCAGGG TTTACTTTTA        60

GTGGCTTCTG GATGAGCTGG GTTCGACAGA CACCTGGGAA GACCCTGGAG TGGATTGGAG       120

ACATTAATTC TGATGGCAGT GCAATAAACT ACGCACCATC CATAAAGGAT CGATTCACTA       180

TCTTCAGAGA CAATGACAAG AGCACCCTGT ACCTGCAG                              218
```

( 2 ) INFORMATION FOR SEQ ID NO:12:

( i ) SEQUENCE CHARACTERISTICS:
        ( A ) LENGTH: 147 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:12:

```
CTGCAGATGA GCAATGTGCG ATCTGAGGAC ACAGCCACGT ATTTCTGTAT GAGATATGAT        60

GGTTACTACT GGTACTTCGA TGTCTGGGGC GCAGGGACCA CGGTCACCGT CTCCTCAGAG       120

AGTCAGTCCT TCCCAAGTCT TAAGCTT                                          147
```

( 2 ) INFORMATION FOR SEQ ID NO:13:

( i ) SEQUENCE CHARACTERISTICS:
        ( A ) LENGTH: 114 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:13:

```
CTGCAGATGA   GCAATGTGCG   ATCTGAGGAC   ACAGCCACGT   ATTTCTGTAT   GAGATATGAT        60
GGTTACTACT   GGTACTTCGA   TGTCTGGGGC   GCAGGGACCA   CGGTCACCGT   CTCC             114
```

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:14:

```
GAGAGTCAGT   CCTTCCCAAA   TGTCTTAAGC   TTCC                                        34
```

( 2 ) INFORMATION FOR SEQ ID NO:15:

( i ) SEQUENCE CHARACTERISTICS:
        ( A ) LENGTH: 390 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:15:

```
AGGTSMARCT   GCAGGAGTCW   GGAGGAGGCT   TGGTGCAACC   TGGGGGGTCA   CGGGGACTCT        60
CTTGTGAAGG   CTCAGGGTTT   ACTTTTAGTG   GCTTCTGGAT   GAGCTGGGTT   CGACAGACAC       120
CTGGGAAGAC   CCTGGAGTGG   ATTGGAGACA   TTAATTCTGA   TGGCAGTGCA   ATAAACTACG       180
CACCATCCAT   AAAGGATCGA   TTCACTATCT   TCAGAGACAA   TGACAAGAGC   ACCCTGTACC       240
TGCAGATGAG   CAATGTGCGA   TCTGAGGACA   CAGCCACGTA   TTTCTGTATG   AGATATGATG       300
GTTACTACTG   GTACTTCGAT   GTCTGGGGCG   CAGGGACCAC   GGTCACCGTC   TCCTCAGAGA       360
GTCAGTCCTT   CCCAAATGTC   TTAAGCTTCC                                             390
```

( 2 ) INFORMATION FOR SEQ ID NO:16:

( i ) SEQUENCE CHARACTERISTICS:
        ( A ) LENGTH: 390 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:16:

| AGGTSMARCT | GCAGGAGTCW | GGAGGAGGCT | TGGTGCAACC | TGGGGGGTCA | CGGGGACTCT | 60 |
|---|---|---|---|---|---|---|
| CTTGTGAAGG | CTCAGGGTTT | ACTTTTAGTG | GCTTCTGGAT | GAGCTGGGTT | CGACAGACAC | 120 |
| CTGGGAAGAC | CCTGGAGTGG | ATTGGAGACA | TTAATTCTGA | TGGCAGTGCA | ATAAACTACG | 180 |
| CACCATCCAT | AAAGGATCGA | TTCACTATCT | TCAGAGACAA | TGACAAGAGC | ACCCTGTACC | 240 |
| TGCAGATGAG | CAATGTGCGA | TCTGAGGACA | CAGCCACGTA | TTTCTGTATG | AGATATGATG | 300 |
| GTTACTACTG | GTACTTCGAT | GTCTGGGGCG | CAGGGACCAC | GGTCACCGTC | TCCTCAGAGA | 360 |
| GTCAGTCCTT | CCCAAATGTC | TTAAGCTTCC | | | | 390 |

( 2 ) INFORMATION FOR SEQ ID NO:17:

( i ) SEQUENCE CHARACTERISTICS:
        ( A ) LENGTH: 390 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:17:

| TCCASKTYGA | CGTCCTCAGW | CCTCCTCCGA | ACCACGTTGG | ACCCCCAGT | GCCCCTGAGA | 60 |
|---|---|---|---|---|---|---|
| GAACACTTCC | GAGTCCCAAA | TGAAAATCAC | CGAAGACCTA | CTCGACCCAA | GCTGTCTGTG | 120 |
| GACCCTTCTG | GGACCTCACC | TAACCTCTGT | AATTAAGACT | ACCGTCACGT | TATTTGATGC | 180 |
| GTGGTAGGTA | TTTCCTAGCT | AAGTGATAGA | AGTCTCTGTT | ACTGTTCTCG | TGGGACATGG | 240 |
| ACGTCTACTC | GTTACACGCT | AGACTCCTGT | GTCGGTGCAT | AAAGACATAC | TCTATACTAC | 300 |
| CAATGATGAC | CATGAAGCTA | CAGACCCCGC | GTCCCTGGTG | CCAGTGGCAG | AGGAGTCTCT | 360 |
| CAGTCAGGAA | GGGTTTACAG | AATTCGAAGG | | | | 390 |

( 2 ) INFORMATION FOR SEQ ID NO:18:

( i ) SEQUENCE CHARACTERISTICS:
        ( A ) LENGTH: 126 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:18:

| Val | Lys | Leu | Gln | Glu | Ser | Gly | Gly | Gly | Leu | Val | Gln | Pro | Gly | Gly | Ser |
|---|---|---|---|---|---|---|---|---|---|---|---|---|---|---|---|
| 1 | | | | 5 | | | | | 10 | | | | | 15 | |
| Arg | Gly | Leu | Ser | Cys | Glu | Gly | Ser | Gly | Phe | Thr | Phe | Ser | Gly | Phe | Trp |
| | | | 20 | | | | | 25 | | | | | 30 | | |
| Met | Ser | Trp | Val | Arg | Gln | Thr | Pro | Gly | Lys | Thr | Leu | Glu | Trp | Ile | Gly |
| | | 35 | | | | | 40 | | | | | 45 | | | |
| Asp | Ile | Asn | Ser | Asp | Gly | Ser | Ala | Ile | Asn | Tyr | Ala | Pro | Ser | Ile | Lys |

|  |  |  |  | 50 |  |  |  |  | 55 |  |  |  |  | 60 |  |
|---|---|---|---|---|---|---|---|---|---|---|---|---|---|---|---|

Asp Arg Phe Thr Ile Phe Arg Asp Asn Asp Lys Ser Thr Leu Tyr Leu
65                  70                  75                  80

Gln Met Ser Asn Val Arg Ser Glu Asp Thr Ala Thr Tyr Phe Cys Met
                85                  90                  95

Arg Tyr Asp Gly Tyr Tyr Trp Tyr Phe Asp Val Trp Gly Ala Gly Thr
            100                 105                 110

Thr Val Thr Val Ser Ser Glu Ser Gln Ser Phe Pro Asn Val
        115                 120                 125

( 2 ) INFORMATION FOR SEQ ID NO:19:

( i ) SEQUENCE CHARACTERISTICS:
        ( A ) LENGTH: 126 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:19:

Val Gln Leu Gln Glu Ser Gly Gly Gly Leu Val Gln Pro Gly Gly Ser
1                   5                   10                  15

Arg Gly Leu Ser Cys Glu Gly Ser Gly Phe Thr Phe Ser Gly Phe Trp
            20                  25                  30

Met Ser Trp Val Arg Gln Thr Pro Gly Lys Thr Leu Glu Trp Ile Gly
        35                  40                  45

Asp Ile Asn Ser Asp Gly Ser Ala Ile Asn Tyr Ala Pro Ser Ile Lys
    50                  55                  60

Asp Arg Phe Thr Ile Phe Arg Asp Asn Asp Lys Ser Thr Leu Tyr Leu
65                  70                  75                  80

Gln Met Ser Asn Val Arg Ser Glu Asp Thr Ala Thr Tyr Phe Cys Met
                85                  90                  95

Arg Tyr Asp Gly Tyr Tyr Trp Tyr Phe Asp Val Trp Gly Ala Gly Thr
            100                 105                 110

Thr Val Thr Val Ser Ser Glu Ser Gln Ser Phe Pro Asn Val
        115                 120                 125

( 2 ) INFORMATION FOR SEQ ID NO:20:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:20:

GGCTTCTGGA TGAGC                                                            15

( 2 ) INFORMATION FOR SEQ ID NO:21:

( i ) SEQUENCE CHARACTERISTICS:
        ( A ) LENGTH: 15 base pairs
        ( B ) TYPE: nucleic acid ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:21:

CCGAAGACCT ACTCG     15

( 2 ) INFORMATION FOR SEQ ID NO:22:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:22:

Gly Phe Trp Met Ser
1               5

( 2 ) INFORMATION FOR SEQ ID NO:23:

( i ) SEQUENCE CHARACTERISTICS:
        ( A ) LENGTH: 51 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:23:

GACATTAATT CTGATGGCAG TGCAATAAAC TACGCACCAT CCATAAAGGA T     51

( 2 ) INFORMATION FOR SEQ ID NO:24:

( i ) SEQUENCE CHARACTERISTICS:
        ( A ) LENGTH: 51 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:24:

CTGTAATTAA GACTACCGTC ACGTTATTTG ATGCGTGGTA GGTATTTCCT A     51

( 2 ) INFORMATION FOR SEQ ID NO:25:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown (i i) MOLECULE TYPE: DNA (genomic)

(i i i) HYPOTHETICAL: N (i v) ANTI-SENSE: N (x i) SEQUENCE DESCRIPTION: SEQ ID NO:25:

| Asp | Ile | Asn | Ser | Asp | Gly | Ser | Ala | Ile | Asn | Tyr | Ala | Pro | Ser | Ile | Lys |
| 1 | | | | 5 | | | | | 10 | | | | | 15 | |

Asp (2) INFORMATION FOR SEQ ID NO:26:

(i) SEQUENCE CHARACTERISTICS:
 (A) LENGTH: 30 base pairs
 (B) TYPE: nucleic acid
 (C) STRANDEDNESS: unknown
 (D) TOPOLOGY: unknown (i i) MOLECULE TYPE: DNA (genomic)

(i i i) HYPOTHETICAL: N (i v) ANTI-SENSE: N (x i) SEQUENCE DESCRIPTION: SEQ ID NO:26:

TATGATGGTT ACTACTGGTA CTTCGATGTC    30

(2) INFORMATION FOR SEQ ID NO:27:

(i) SEQUENCE CHARACTERISTICS:
 (A) LENGTH: 30 base pairs
 (B) TYPE: nucleic acid
 (C) STRANDEDNESS: unknown
 (D) TOPOLOGY: unknown (i i) MOLECULE TYPE: DNA (genomic)

(i i i) HYPOTHETICAL: N (i v) ANTI-SENSE: N (x i) SEQUENCE DESCRIPTION: SEQ ID NO:27:

ATACTACCAA TGATGACCAT GAAGCTACAG    30

(2) INFORMATION FOR SEQ ID NO:28:

(i) SEQUENCE CHARACTERISTICS:
 (A) LENGTH: 10 amino acids
 (B) TYPE: amino acid
 (C) STRANDEDNESS: unknown
 (D) TOPOLOGY: unknown (i i) MOLECULE TYPE: DNA (genomic)

(i i i) HYPOTHETICAL: N (i v) ANTI-SENSE: N (x i) SEQUENCE DESCRIPTION: SEQ ID NO:28:

| Tyr | Asp | Gly | Tyr | Tyr | Trp | Tyr | Phe | Asp | Val |
| 1 | | | | 5 | | | | | 10 |

(2) INFORMATION FOR SEQ ID NO:29:

(i) SEQUENCE CHARACTERISTICS:
 (A) LENGTH: 121 amino acids
 (B) TYPE: amino acid
 (C) STRANDEDNESS: unknown
 (D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:29:

| Xaa | Val | Xaa | Leu | Gln | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |
| Ser | Arg | Gly | Leu | Ser | Cys | Glu | Gly | Ser | Gly | Phe | Thr | Phe | Ser | Gly | Phe |
| | | | 20 | | | | 25 | | | | | 30 | | | |
| Trp | Met | Ser | Trp | Val | Arg | Gln | Thr | Pro | Gly | Lys | Thr | Leu | Glu | Trp | Ile |
| | | 35 | | | | 40 | | | | | 45 | | | | |
| Gly | Asp | Ile | Asn | Ser | Asp | Gly | Ser | Ala | Ile | Asn | Tyr | Ala | Pro | Ser | Ile |
| | 50 | | | | | 55 | | | | | 60 | | | | |
| Lys | Asp | Arg | Phe | Thr | Ile | Phe | Arg | Asp | Asn | Asp | Lys | Ser | Thr | Leu | Tyr |
| 65 | | | | 70 | | | | | 75 | | | | | 80 | |
| Leu | Tyr | Leu | Gln | Met | Ser | Asn | Val | Arg | Ser | Glu | Asp | Thr | Ala | Thr | Tyr |
| | | | | 85 | | | | | 90 | | | | | 95 | |
| Phe | Cys | Met | Arg | Tyr | Asp | Gly | Tyr | Tyr | Trp | Tyr | Phe | Asp | Val | Trp | Gly |
| | | | 100 | | | | | 105 | | | | | 110 | | |
| Ala | Gly | Thr | Thr | Val | Thr | Val | Ser | Ser | | | | | | | |
| | | 115 | | | | | 120 | | | | | | | | |

(2) INFORMATION FOR SEQ ID NO:30:

(i) SEQUENCE CHARACTERISTICS:
(A) LENGTH: 120 amino acids
(B) TYPE: amino acid
(C) STRANDEDNESS: unknown
(D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:30:

| Glu | Val | Lys | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |
| Ser | Leu | Lys | Leu | Ser | Cys | Ala | Ala | Ser | Gly | Phe | Asp | Phe | Ser | Arg | Tyr |
| | | | 20 | | | | 25 | | | | | 30 | | | |
| Trp | Met | Ser | Trp | Val | Arg | Gln | Ala | Pro | Gly | Lys | Gly | Leu | Glu | Trp | Ile |
| | | 35 | | | | 40 | | | | | 45 | | | | |
| Gly | Glu | Ile | Asn | Pro | Lys | Ala | Asp | Ser | Ser | Thr | Ile | Asn | Tyr | Thr | Pro |
| | 50 | | | | | 55 | | | | | 60 | | | | |
| Ser | Leu | Lys | Asp | Lys | Phe | Ile | Ile | Ser | Arg | Asp | Asn | Ala | Lys | Asn | Thr |
| 65 | | | | 70 | | | | | 75 | | | | | 80 | |
| Leu | Tyr | Leu | Gln | Met | Ser | Lys | Val | Arg | Ser | Glu | Asp | Thr | Ala | Leu | Tyr |
| | | | | 85 | | | | | 90 | | | | | 95 | |
| Tyr | Cys | Ala | Arg | Leu | Gly | Tyr | Tyr | Gly | Tyr | Phe | Ala | Tyr | Trp | Gly | |
| | | | 100 | | | | | 105 | | | | | 110 | | |
| Gln | Gly | Thr | Thr | Val | Thr | Val | Ser | Ser | | | | | | | |
| | | | 115 | | | | | 120 | | | | | | | |

(2) INFORMATION FOR SEQ ID NO:31:

(i) SEQUENCE CHARACTERISTICS:
(A) LENGTH: 5 amino acids
(B) TYPE: amino acid
(C) STRANDEDNESS: unknown (D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:31:

Gly Phe Trp Met Ser
1               5

(2) INFORMATION FOR SEQ ID NO:32:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:32:

Arg Tyr Trp Met Ser
1               5

(2) INFORMATION FOR SEQ ID NO:33:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:33:

Asp Ile Asn Ser Asp Gly Ser Ala Ile Asn Tyr Ala Pro Ser Ile
1               5                   10                  15

Lys Asp (2) INFORMATION FOR SEQ ID NO:34:

(i) SEQUENCE CHARACTERISTICS:
        (A) LENGTH: 19 amino acids
        (B) TYPE: amino acid
        (C) STRANDEDNESS: unknown
        (D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:34:

Glu Ile Asn Pro Lys Ala Asp Ser Ser Thr Ile Asn Tyr Thr Pro Ser
1               5                   10                  15

Leu Lys Asp (2) INFORMATION FOR SEQ ID NO:35:

( i ) SEQUENCE CHARACTERISTICS:
     ( A ) LENGTH: 10 amino acids
     ( B ) TYPE: amino acid
     ( C ) STRANDEDNESS: unknown
     ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:35:

```
Tyr Asp Gly Tyr Tyr Trp Tyr Phe Asp Val
1               5                   10
```

( 2 ) INFORMATION FOR SEQ ID NO:36:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:36:

```
Leu Gly Tyr Tyr Gly Tyr Phe Ala Tyr
1               5
```

( 2 ) INFORMATION FOR SEQ ID NO:37:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:37:

```
GACATTCAGC TGACCCAGTC TCCA                                              24
```

( 2 ) INFORMATION FOR SEQ ID NO:38:

( i ) SEQUENCE CHARACTERISTICS:
        ( A ) LENGTH: 291 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:38:

```
CTGACCCAGT CTCCATCCTC CATGTATGCA TCGCTGGGAG AGAGAGTCAC TATCACTTGC        60
AAGGCGAGTC AGGACATTAA AAGCTATTTA AGCTGGTACC AGCAGAAACC ATGGAAATCT       120
CCTAAGACCC TGATCTATTA TGCAACAAGC TTGGCAGATG GGTCCCATC  AAGATTCAGT       180
GGCAGTGGAT CTGGGCAAGA TTATTCTCTA ACCATCAGCA GCCTGGAGTC TGACGATACA       240
```

GCAACTTATT ACTGTCTACA GCATGGTGAG AGCCCGCTCA CGTTCGGTGC T        291

( 2 ) INFORMATION FOR SEQ ID NO:39:

( i ) SEQUENCE CHARACTERISTICS:
           ( A ) LENGTH: 140 base pairs
           ( B ) TYPE: nucleic acid
           ( C ) STRANDEDNESS: unknown
           ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:39:

CTGACCCAGT CTCCATCCTC CATGTATGCA TCGCTGGGAG AGAGAGTCAC TATCACTTGC        60

AAGGCGAGTC AGGACATTAA AAGCTATTTA AGCTGGTACC AGCAGAAACC ATGGAAATCT        120

CCTAAGACCC TGATCTATTA        140

( 2 ) INFORMATION FOR SEQ ID NO:40:

( i ) SEQUENCE CHARACTERISTICS:
           ( A ) LENGTH: 92 base pairs
           ( B ) TYPE: nucleic acid
           ( C ) STRANDEDNESS: unknown
           ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:40:

CTGACCCAGT CTCCATCCTC CATGTATGCA TCGCTGGGAG AGAGAGTCAC TATCACTTGC        60

AAGGCGAGTC AGGACATTAA AAGCTATTTA AG        92

( 2 ) INFORMATION FOR SEQ ID NO:41:

( i ) SEQUENCE CHARACTERISTICS:
           ( A ) LENGTH: 152 base pairs
           ( B ) TYPE: nucleic acid
           ( C ) STRANDEDNESS: unknown
           ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:41:

CTGACCCAGT CTCCATCCTC CATGTATGCA TCGCTGGGAG AGAGAGTCAC TATCACTTGC        60

AAGGCGAGTC AGGACATTAA AAGCTATTTA AGCTGGTACC AGCAGAAACC ATGGAAATCT        120

CCTAAGACCC TGATCTATTA TGCAACAAGC TT        152

( 2 ) INFORMATION FOR SEQ ID NO:42:

( i ) SEQUENCE CHARACTERISTICS:
           ( A ) LENGTH: 141 base pairs
           ( B ) TYPE: nucleic acid
           ( C ) STRANDEDNESS: unknown
           ( D ) TOPOLOGY: unknown ( i i ) MOLECULE TYPE: DNA (genomic)

(i i i) HYPOTHETICAL: N (i v) ANTI-SENSE: N (x i) SEQUENCE DESCRIPTION: SEQ ID NO:42:

| | | | | | |
|---|---|---|---|---|---|
| CTCCATCCTC | CATGTATGCA | TCGCTGGGAG | AGAGAGTCAC | TATCACTTGC | AAGGCGAGTC | 60 |
| AGGACATTAA | AAGCTATTTA | AGCTGGTACC | AGCAGAAACC | ATGGAAATCT | CCTAAGACCC | 120 |
| TGATCTATTA | TGCAACAAGC | T | | | | 141 |

(2) INFORMATION FOR SEQ ID NO:43:

(i) SEQUENCE CHARACTERISTICS:
        (A) LENGTH: 84 base pairs
        (B) TYPE: nucleic acid
        (C) STRANDEDNESS: unknown
        (D) TOPOLOGY: unknown (i i) MOLECULE TYPE: DNA (genomic)

(i i i) HYPOTHETICAL: N (i v) ANTI-SENSE: N (x i) SEQUENCE DESCRIPTION: SEQ ID NO:43:

| | | | | | |
|---|---|---|---|---|---|
| TCCATCCTCC | ATGTATGCAT | CGCTGGGAGA | GAGAGTCACT | ATCACTTGCA | AGGCGAGTCA | 60 |
| GGACATTAAA | AGCTATTTAA | GCTG | | | | 84 |

(2) INFORMATION FOR SEQ ID NO:44:

(i) SEQUENCE CHARACTERISTICS:
        (A) LENGTH: 140 base pairs
        (B) TYPE: nucleic acid
        (C) STRANDEDNESS: unknown
        (D) TOPOLOGY: unknown (i i) MOLECULE TYPE: DNA (genomic)

(i i i) HYPOTHETICAL: N (i v) ANTI-SENSE: N (x i) SEQUENCE DESCRIPTION: SEQ ID NO:44:

| | | | | | |
|---|---|---|---|---|---|
| TCCATCCCCC | ATGTATGCAT | CGCTGGGAGA | GAGAGTCACT | ATCACTTGCA | AGGCGAGTCA | 60 |
| GGACATTAAA | AGCTATTTAA | GCTGGTACCA | GCAGAAACCA | TGGAAATCTC | CTAAGACCCT | 120 |
| GATCTATTAT | GCAACAAGCT | | | | | 140 |

(2) INFORMATION FOR SEQ ID NO:45:

(i) SEQUENCE CHARACTERISTICS:
        (A) LENGTH: 140 base pairs
        (B) TYPE: nucleic acid
        (C) STRANDEDNESS: unknown
        (D) TOPOLOGY: unknown (i i) MOLECULE TYPE: DNA (genomic)

(i i i) HYPOTHETICAL: N (i v) ANTI-SENSE: N (x i) SEQUENCE DESCRIPTION: SEQ ID NO:45:

| | | | | | |
|---|---|---|---|---|---|
| TCCATCCTCC | ATGTATGCAT | CGCTGGGAGA | GAGAGTCACT | ATCACTTGCA | AGGCGAGTCA | 60 |
| GGACATTAAA | AGCTATTTAA | GCTGGTACCA | GCAGAAACCA | TGGAAATCTC | CTAAGACCCT | 120 |
| GATCTATTAT | GCAACAAGCT | | | | | 140 |

( 2 ) INFORMATION FOR SEQ ID NO:46:

( i ) SEQUENCE CHARACTERISTICS:
    ( A ) LENGTH: 265 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:46:

```
TGCATCGCTG GGAGAGAGAG TCACTATCAC TTGCAAGGCG AGTCAGGACA TTAAAAGCTA      60
TTTAAGCTGG TACCAGCAGA AACCATGGAA ATCTCCTAAG ACCCTGATCT ATTATGCAAC     120
AAGCTTGGCA GATGGGGTCC CATCAAGATT CAGTGGCAGT GGATCTGGGC AAGATTATTC     180
TCTAACCATC AGCAGCCTGG AGTCTGACGA TACAGCAACT TATTACTGTC TACAGCATGG     240
TGAGAGCCCG CTCACGTTCG GTGCT                                          265
```

( 2 ) INFORMATION FOR SEQ ID NO:47:

( i ) SEQUENCE CHARACTERISTICS:
    ( A ) LENGTH: 265 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:47:

```
TGCATCGCTG GGAGAGAGAG TCACTATCAC TTGCAAGGCG AGTCAGGACA TTAAAAGCTA      60
TTTAAGCTGG TACCAGCAGA AACCATGGAA ATCTCCTAAG ACCCTGATCT ATTATGCAAC     120
AAGCTTGGCA GATGGGGTCC CATCAAGATT CAGTGGCAGT GGATCTGGGC AAGATTATTC     180
TCTAACCATC AGCAGCCTGG AGTCTGACGA TACAGCAACT TATTACTGTC TACAGCATGG     240
TGAGAGCCCG CTCACGTTCG GTGCT                                          265
```

( 2 ) INFORMATION FOR SEQ ID NO:48:

( i ) SEQUENCE CHARACTERISTICS:
    ( A ) LENGTH: 265 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:48:

```
TGCATCGCTG GGAGAGAGAG TCACTATCAC TTGCAAGGCG AGTCAGGACA TTAAAAGCTA      60
TTTAAGCTGG TACCAGCAGA AACCATGGAA ATCTCCTAAG ACCCTGATCT ATTATGCAAC     120
AAGCTTGGCA GATGGGGTCC CATCAAGATT CAGTGGCAGT GGATCTGGGC AAGATTATTC     180
TCTAACCATC AGCAGCCTGG AGTCTGACGA TACAGCAACT TATTACTGTC TACAGCATGG     240
TGAGAGCCCG CTCACGTTCG GTGCT                                          265
```

( 2 ) INFORMATION FOR SEQ ID NO:49:

( i ) SEQUENCE CHARACTERISTICS:
        ( A ) LENGTH: 264 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:49:

| | | | | | | |
|---|---|---|---|---|---|---|
| GCATCGCTGG | GAGAGAGAGT | CACTATCACT | TGCAAGGCGA | GTCAGGACAT | TAAAAGCTAT | 60 |
| TTAAGCTGGT | ACCAGCAGAA | ACCATGGAAA | TCTCCTAAGA | CCCTGATCTA | TTATGCAACA | 120 |
| AGCTTGGCAG | ATGGGGTCCC | ATCAAGATTC | AGTGGCAGTG | GATCTGGGCA | AGATTATTCT | 180 |
| CTAACCATCA | GCAGCCTGGA | GTCTGACGAT | ACAGCAACTT | ATTACTGTCT | ACAGCATGGT | 240 |
| GAGAGCCCGC | TCACGTTCGG | TGCT | | | | 264 |

( 2 ) INFORMATION FOR SEQ ID NO:50:

( i ) SEQUENCE CHARACTERISTICS:
        ( A ) LENGTH: 264 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:50:

| | | | | | | |
|---|---|---|---|---|---|---|
| GCATCGCTGG | GAGAGAGAGT | CACTATCACT | TGCAAGGCGA | GTCAGGACAT | TAAAAGCTAT | 60 |
| TTAAGCTGGT | ACCAGCAGAA | ACCATGGAAA | TCTCCTAAGA | CCCTGATCTA | TTATGCAACA | 120 |
| AGCTTGGCAG | ATGGGGTCCC | ATCAAGATTC | AGTGGCAGTG | GATCTGGGCA | AGATTATTCT | 180 |
| CTAACCATCA | GCAGCCTGGA | GTCTGACGAT | ACAGCAACTT | ATTACTGTCT | ACAGCATGGT | 240 |
| GAGAGCCCGC | TCACGTTCGG | TGCT | | | | 264 |

( 2 ) INFORMATION FOR SEQ ID NO:51:

( i ) SEQUENCE CHARACTERISTICS:
        ( A ) LENGTH: 263 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:51:

| | | | | | | |
|---|---|---|---|---|---|---|
| CATCGCTGGG | AGAGAGAGTC | ACTATCACTT | GCAAGGCGAG | TCAGGACATT | AAAAGCTATT | 60 |
| TAAGCTGGTA | CCAGCAGAAA | CCATGGAAAT | CTCCTAAGAC | CCTGATCTAT | TATGCAACAA | 120 |
| GCTTGGCAGA | TGGGGTCCCA | TCAAGATTCA | GTGGCAGTGG | ATCTGGGCAA | GATTATTCTC | 180 |
| TAACCATCAG | CAGCCTGGAG | TCTGACGATA | CAGCAACTTA | TTACTGTCTA | CAGCATGGTG | 240 |

```
AGAGCCCGCT CACGTTCGGT GCT                                                                      263
```

( 2 ) INFORMATION FOR SEQ ID NO:52:

( i ) SEQUENCE CHARACTERISTICS:
        ( A ) LENGTH: 260 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:52:

```
CGCTGGGAGA GAGAGTCACT ATCACTTGCA AGGCGAGTCA GGACATTAAA AGCTATTTAA    60
GCTGGTACCA GCAGAAACCA TGGAAATCTC CTAAGACCCT GATCTATTAT GCAACAAGCT   120
TGGCAGATGG GGTCCCATCA AGATTCAGTG GCAGTGGATC TGGGCAAGAT TATTCTCTAA   180
CCATCAGCAG CCTGGAGTCT GACGATACAG CAACTTATTA CTGTCTACAG CATGGTGAGA   240
GCCCGCTCAC GTTCGGTGCT                                                260
```

( 2 ) INFORMATION FOR SEQ ID NO:53:

( i ) SEQUENCE CHARACTERISTICS:
        ( A ) LENGTH: 88 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:53:

```
AAGGCGAGTC AGGACATTAA AAGCTATTTA AGCTGGTACC AGCAGAAACC ATGGAAATCT    60
CCTAAGACCC TGATCTATTA TGCAACAA                                       88
```

( 2 ) INFORMATION FOR SEQ ID NO:54:

( i ) SEQUENCE CHARACTERISTICS:
        ( A ) LENGTH: 203 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:54:

```
AGCTTGGCAG ATGGGGTCCC ATCAAGATTC AGTGGCAGTG GATCTGGGCA AGATTATTCT    60
CTAACCATCA GCAGCCTGGA GTCTGACGAT ACAGCAACTT ATTACTGTCT ACAGCATGGT   120
GAGAGCCCGC TCACGTTCGG TGCTGGGACC AAGCTGGAGC TGAAACGGGC TGATGCTGCA   180
CCAACTGTAT CCACTTCAAG CTT                                            203
```

( 2 ) INFORMATION FOR SEQ ID NO:55:

( i ) SEQUENCE CHARACTERISTICS:
        ( A ) LENGTH: 204 base pairs (B) TYPE: nucleic acid
(C) STRANDEDNESS: unknown
(D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:55:

| | | | | | | |
|---|---|---|---|---|---|---|
| AGCTTGGCAG | ATGGGGTCCC | ATCAAGATTC | AGTGGCAGTG | GATCTGGGCA | AGATTATTCT | 60 |
| CTAACCATCA | GCAGCCTGGA | GTCTGACGAT | ACAGCAACTT | ATTACTGTCT | ACAGCATGGT | 120 |
| GAGAGCCCGC | TCACGTTCGG | TGCTGGGACC | AAGCTGGAGC | TGAAACGGGC | TGATGCTGCA | 180 |
| CCAACTGTAT | CCATCTTCAA | GCTT | | | | 204 |

(2) INFORMATION FOR SEQ ID NO:56:

(i) SEQUENCE CHARACTERISTICS:
(A) LENGTH: 175 base pairs
(B) TYPE: nucleic acid
(C) STRANDEDNESS: unknown
(D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:56:

| | | | | | | |
|---|---|---|---|---|---|---|
| AGCTTGGCAG | ATGGGGTCCC | ATCAAGATTC | AGTGGCAGTG | GATCTGGGCA | AGATTATTCT | 60 |
| CTAACCATCA | GCAGCCTGGA | GTCTGACGAT | ACAGCAACTT | ATTACTGTCT | ACAGCATGGT | 120 |
| GAGAGCCCGC | TCACGTTCGG | TGCTGGGACC | AAGCTGGAGC | TGAAACGGGC | TGATG | 175 |

(2) INFORMATION FOR SEQ ID NO:57:

(i) SEQUENCE CHARACTERISTICS:
(A) LENGTH: 167 base pairs
(B) TYPE: nucleic acid
(C) STRANDEDNESS: unknown
(D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:57:

| | | | | | | |
|---|---|---|---|---|---|---|
| CTTGGCAGAT | GGGGTCCCAT | CAAGATTCAG | TGGCAGTGGA | TCTGGGCAAG | ATTATTCTCT | 60 |
| AACCATCAGC | AGCCTGGAGT | CTGACGATAC | AGCAACTTAT | TACTGTCTAC | AGCATGGTGA | 120 |
| GAGCCCGCTC | ACGTTCGGTG | CTGGGACCAA | GCTGGAGCTG | AAACGGG | | 167 |

(2) INFORMATION FOR SEQ ID NO:58:

(i) SEQUENCE CHARACTERISTICS:
(A) LENGTH: 154 base pairs
(B) TYPE: nucleic acid
(C) STRANDEDNESS: unknown
(D) TOPOLOGY: unknown (ii) MOLECULE TYPE: DNA (genomic)

(iii) HYPOTHETICAL: N (iv) ANTI-SENSE: N ( x i ) SEQUENCE DESCRIPTION: SEQ ID NO:58:

| | | | | | |
|---|---|---|---|---|---|
| AAGATTATTC | TCTAACCATC | AGCAGCCTGG | AGTCTGACGA | TACAGCAACT | TATTACTGTC | 60
| TACAGCATGG | TGAGAGCCCG | CTCACGTTCG | GTGCTGGGAC | CAAGCTGGAG | CTGAAACGGG | 120
| CTGATGCTGC | ACCAACTGTA | TCCATCTTCA | AGCT | | | 154

( 2 ) INFORMATION FOR SEQ ID NO:59:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:59:

GCTGCACCAA CTGTATCCAT CTTCAAGCTT CC    32

( 2 ) INFORMATION FOR SEQ ID NO:60:

( i ) SEQUENCE CHARACTERISTICS:
        ( A ) LENGTH: 362 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:60:

| | | | | | |
|---|---|---|---|---|---|
| GACATTCAGC | TGACCCAGTC | TCCATCCTCC | ATGTATGCAT | CGCTGGGAGA | GAGAGTCACT | 60
| ATCACTTGCA | AGGCGAGTCA | GGACATTAAA | AGCTATTTAA | GCTGGTACCA | GCAGAAACCA | 120
| TGGAAATCTC | CTAAGACCCT | GATCTATTAT | GCAACAAGCT | TGGCAGATGG | GGTCCCATCA | 180
| AGATTCAGTG | GCAGTGGATC | TGGGCAAGAT | TATTCTCTAA | CCATCAGCAG | CCTGGAGTCT | 240
| GACGATACAG | CAACTTATTA | CTGTCTACAG | CATGGTGAGA | GCCCGCTCAC | GTTCGGTGCT | 300
| GGGACCAAGC | TGGAGCTGAA | ACGGGCTGAT | GCTGCACCAA | CTGTATCCAT | CTTCAAGCTT | 360
| CC | | | | | | 362

( 2 ) INFORMATION FOR SEQ ID NO:61:

( i ) SEQUENCE CHARACTERISTICS:
        ( A ) LENGTH: 449 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:61:

| | | | | | |
|---|---|---|---|---|---|
| CTGCAGSAGT | CWGGACTCAG | CATGGACATG | AGGGCCCCTG | CTCAGTTTTT | TGGGATCTTG | 60
| TTGCTCTGGT | TTCCAGGTAT | CAGATGTGAC | ATCAAGATGA | CCCAGTCTCC | ATCCTCCATG | 120

```
TATGCATCGC TGGGAGAGAG AGTCACTATC ACTTGCAAGG CGAGTCAGGA CATTAAAAGC    180

TATTTAAGCT GGTACCAGCA GAAACCATGG AAATCTCCTA AGACCCTGAT CTATTATGCA    240

ACAAGCTTGG CAGATGGGGT CCCATCAAGA TTCAGTGGCA GTGGATCTGG GCAAGATTAT    300

TCTCTAACCA TCAGCAGCCT GGAGTCTGAC GATACAGCAA CTTATTACTG TCTACAGCAT    360

GGTGAGAGCC CGCTCACGTT CGGTGCTGGG ACCAAGCTGG AGCTGAAACG GGCTGATGCT    420

GCACCAACTG TATCCATCTT CAAGCTTCC                                      449
```

( 2 ) INFORMATION FOR SEQ ID NO:62:

( i ) SEQUENCE CHARACTERISTICS:
        ( A ) LENGTH: 449 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:62:

```
GACGTCSTCA GWCCTGAGTC GTACCTGTAC TCCCGGGGAC GAGTCAAAAA ACCCTAGAAC     60

AACGAGACCA AAGGTCCATA GTCTACACTG TAGTTCTACT GGGTCAGAGG TAGGAGGTAC    120

ATACGTAGCG ACCCTCTCTC TCAGTGATAG TGAACGTTCC GCTCAGTCCT GTAATTTTCG    180

ATAAATTCGA CCATGGTCGT CTTTGGTACC TTTAGAGGAT TCTGGGACTA GATAATACGT    240

TGTTCGAACC GTCTACCCCA GGGTAGTTCT AAGTCACCGT CACCTAGACC CGTTCTAATA    300

AGAGATTGGT AGTCGTCGGA CCTCAGACTG CTATGTCGTT GAATAATGAC AGATGTCGTA    360

CCACTCTCGG GCGAGTGCAA GCCACGACCC TGGTTCGACC TCGACTTTGC CCGACTACGA    420

CGTGGTTGAC ATAGGTAGAA GTTCGAAGG                                      449
```

( 2 ) INFORMATION FOR SEQ ID NO:63:

( i ) SEQUENCE CHARACTERISTICS:
        ( A ) LENGTH: 138 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:63:

```
Met Arg Ala Pro Ala Gln Phe Phe Gly Ile Leu Leu Leu Trp Phe Pro
 1               5                  10                  15

Gly Ile Arg Cys Asp Ile Lys Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile Lys Ser Tyr Leu Ser Trp Tyr Gln Gln Lys Pro Trp Lys Ser Pro
    50                  55                  60

Lys Thr Leu Ile Tyr Tyr Ala Thr Ser Leu Ala Asp Gly Val Pro Ser
65                  70                  75                  80

Arg Phe Ser Gly Ser Gly Ser Gly Gln Asp Tyr Ser Leu Thr Ile Ser
                85                  90                  95
```

| Ser | Leu | Glu | Ser | Asp | Asp | Thr | Ala | Thr | Tyr | Tyr | Cys | Leu | Gln | His | Gly |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Glu | Ser | Pro | Leu | Thr | Phe | Gly | Ala | Gly | Thr | Lys | Leu | Glu | Leu | Lys | Arg |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ala | Asp | Ala | Ala | Pro | Thr | Val | Ser | Ile | Phe |
|-----|-----|-----|-----|-----|-----|-----|-----|-----|-----|
|     | 130 |     |     |     |     | 135 |     |     |     |

( 2 ) INFORMATION FOR SEQ ID NO:64:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:64:

AAGGCGAGTC AGGACATTAA AAGCTATTTA AGC        33

( 2 ) INFORMATION FOR SEQ ID NO:65:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:65:

TTCCGCTCAG TCCTGTAATT TTCGATAAAT TCG        33

( 2 ) INFORMATION FOR SEQ ID NO:66:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:66:

| Lys | Ala | Ser | Gln | Asp | Ile | Lys | Ser | Tyr | Leu | Ser |
|-----|-----|-----|-----|-----|-----|-----|-----|-----|-----|-----|
| 1   |     |     |     | 5   |     |     |     |     | 10  |     |

( 2 ) INFORMATION FOR SEQ ID NO:67:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:67:

TATGCAACAA GCTTGGCAGA T                                                                                     21

( 2 ) INFORMATION FOR SEQ ID NO:68:

( i ) SEQUENCE CHARACTERISTICS:
                ( A ) LENGTH: 21 base pairs
                ( B ) TYPE: nucleic acid
                ( C ) STRANDEDNESS: unknown
                ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:68:

ATACGTTGTT CGAACCGTCT A                                                                                     21

( 2 ) INFORMATION FOR SEQ ID NO:69:

( i ) SEQUENCE CHARACTERISTICS:
                ( A ) LENGTH: 7 amino acids
                ( B ) TYPE: amino acid
                ( C ) STRANDEDNESS: unknown
                ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:69:

Tyr  Ala  Thr  Ser  Leu  Ala  Asp
        1                        5

( 2 ) INFORMATION FOR SEQ ID NO:70:

( i ) SEQUENCE CHARACTERISTICS:
                ( A ) LENGTH: 27 base pairs
                ( B ) TYPE: nucleic acid
                ( C ) STRANDEDNESS: unknown
                ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:70:

CTACAGCATG GTGAGAGCCC GCTCACG                                                                               27

( 2 ) INFORMATION FOR SEQ ID NO:71:

( i ) SEQUENCE CHARACTERISTICS:
                ( A ) LENGTH: 27 base pairs
                ( B ) TYPE: nucleic acid
                ( C ) STRANDEDNESS: unknown
                ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:71:

GATGTCGTAC CACTCTCGGG CGAGTGC 27

(2) INFORMATION FOR SEQ ID NO:72:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:72:

Leu Gln His Gly Glu Ser Pro Leu Thr
1               5

(2) INFORMATION FOR SEQ ID NO:73:

(i) SEQUENCE CHARACTERISTICS:
        (A) LENGTH: 107 amino acids
        (B) TYPE: amino acid
        (C) STRANDEDNESS: unknown
        (D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:73:

Asp Ile Gln Leu Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Leu
                85                  90                  95

Thr Phe Gly Ala Gly Thr Lys Leu Glu Leu Lys
            100                 105

(2) INFORMATION FOR SEQ ID NO:74:

(i) SEQUENCE CHARACTERISTICS:
        (A) LENGTH: 107 amino acids
        (B) TYPE: amino acid
        (C) STRANDEDNESS: unknown
        (D) TOPOLOGY: unknown (ii) MOLECULE TYPE: DNA (genomic)

(iii) HYPOTHETICAL: N (iv) ANTI-SENSE: N (xi) SEQUENCE DESCRIPTION: SEQ ID NO:74:

Asp Ile Gln Met Thr Gln Ser Pro Ser Ser Leu Ser Ala Ser Leu Gly
1               5                   10                  15

```
Asp  Arg  Val  Thr  Ile  Thr  Cys  Arg  Ala  Ser  Gln  Asp  Ile  Ser  Asn  Tyr
               20                       25                      30

Leu  Asn  Trp  Tyr  Gln  Gln  Lys  Pro  Gly  Gly  Thr  Pro  Lys  Leu  Leu  Ile
          35                       40                      45

Tyr  Tyr  Ala  Ser  Arg  Leu  His  Ser  Gly  Val  Pro  Ser  Arg  Phe  Ser  Gly
     50                       55                      60

Ser  Gly  Ser  Gly  Thr  Asp  Tyr  Ser  Leu  Thr  Ile  Ser  Ser  Leu  Glu  Gln
65                       70                      75                           80

Glu  Asp  Ile  Ala  Thr  Tyr  Phe  Cys  Gln  Gln  Gly  Asn  Ser  Leu  Pro  Arg
                    85                  90                           95

Thr  Phe  Gly  Gly  Gly  Thr  Lys  Leu  Glu  Ile  Lys
               100                 105
```

( 2 ) INFORMATION FOR SEQ ID NO:75:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:75:

```
Lys  Ala  Ser  Gln  Asp  Ile  Lys  Ser  Tyr  Leu  Ser
1                   5                        10
```

( 2 ) INFORMATION FOR SEQ ID NO:76:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:76:

```
Arg  Ala  Ser  Gln  Asp  Ile  Ser  Asn  Tyr  Leu  Asn
1                   5                        10
```

( 2 ) INFORMATION FOR SEQ ID NO:77:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:77:

```
Tyr  Ala  Thr  Ser  Leu  Ala  Asp
1                   5
```

( 2 ) INFORMATION FOR SEQ ID NO:78:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:78:

Tyr Ala Ser Arg Leu His Ser
1               5

( 2 ) INFORMATION FOR SEQ ID NO:79:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:79:

Leu Gln His Gly Glu Ser Pro Leu Thr
1               5

( 2 ) INFORMATION FOR SEQ ID NO:80:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:80:

Gln Gln Gly Asn Ser Leu Pro Arg Thr
1               5

( 2 ) INFORMATION FOR SEQ ID NO:81:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: N ( i v ) ANTI-SENSE: N ( x i ) SEQUENCE DESCRIPTION: SEQ ID NO:81:

GGAAGCTTGA AGATGGATAC AGTTGGTGCA GC        3 2

( 2 ) INFORMATION FOR SEQ ID NO:82:

(i) SEQUENCE CHARACTERISTICS:
(A) LENGTH: 34 base pairs
(B) TYPE: nucleic acid
(C) STRANDEDNESS: unknown
(D) TOPOLOGY: unknown (ii) MOLECULE TYPE: cDNA (iii) HYPOTHETICAL: N (iv) ANTI-SENSE: N (xi) SEQUENCE DESCRIPTION: SEQ ID NO:82:

GGAAGCTTAA GACATTTGGG AAGGACTGAC TCTC 34

(2) INFORMATION FOR SEQ ID NO:83:

(i) SEQUENCE CHARACTERISTICS:
(A) LENGTH: 22 base pairs
(B) TYPE: nucleic acid
(C) STRANDEDNESS: unknown
(D) TOPOLOGY: unknown (ii) MOLECULE TYPE: cDNA (iii) HYPOTHETICAL: N (iv) ANTI-SENSE: N (xi) SEQUENCE DESCRIPTION: SEQ ID NO:83:

AGGTSMARCT GCAGSAGTCW GG 22

(2) INFORMATION FOR SEQ ID NO:84:

(i) SEQUENCE CHARACTERISTICS:
(A) LENGTH: 34 base pairs
(B) TYPE: nucleic acid
(C) STRANDEDNESS: unknown
(D) TOPOLOGY: unknown (ii) MOLECULE TYPE: cDNA (iii) HYPOTHETICAL: N (iv) ANTI-SENSE: N (xi) SEQUENCE DESCRIPTION: SEQ ID NO:84:

TGAGGAGACG GTGACCGTGG TCCCTTGGCC CCAG 34

(2) INFORMATION FOR SEQ ID NO:85:

(i) SEQUENCE CHARACTERISTICS:
(A) LENGTH: 24 base pairs
(B) TYPE: nucleic acid
(C) STRANDEDNESS: unknown
(D) TOPOLOGY: unknown (ii) MOLECULE TYPE: cDNA (iii) HYPOTHETICAL: N (iv) ANTI-SENSE: N (xi) SEQUENCE DESCRIPTION: SEQ ID NO:85:

GACATTCAGC TGACCCAGTC TCCA 24

(2) INFORMATION FOR SEQ ID NO:86:

(i) SEQUENCE CHARACTERISTICS:
(A) LENGTH: 24 base pairs
(B) TYPE: nucleic acid

```
            ( C ) STRANDEDNESS: unknown
            ( D ) TOPOLOGY: unknown ( i i ) MOLECULE TYPE: cDNA ( i i i ) HYPOTHETICAL: N ( i v ) ANTI-SENSE: N ( x i ) SEQUENCE DESCRIPTION: SEQ ID NO:86:

GACATTGAGC  TCACCCAGTC  TCCA                                            2 4

( 2 ) INFORMATION FOR SEQ ID NO:87:

( i ) SEQUENCE CHARACTERISTICS:
            ( A ) LENGTH: 22 base pairs
            ( B ) TYPE: nucleic acid
            ( C ) STRANDEDNESS: unknown
            ( D ) TOPOLOGY: unknown ( i i ) MOLECULE TYPE: cDNA ( i i i ) HYPOTHETICAL: N ( i v ) ANTI-SENSE: N ( x i ) SEQUENCE DESCRIPTION: SEQ ID NO:87:

GTTAGATCTC  CAGCTTGGTC  CC                                              2 2

( 2 ) INFORMATION FOR SEQ ID NO:88:

( i ) SEQUENCE CHARACTERISTICS:
            ( A ) LENGTH: 21 base pairs
            ( B ) TYPE: nucleic acid
            ( C ) STRANDEDNESS: unknown
            ( D ) TOPOLOGY: unknown ( i i ) MOLECULE TYPE: cDNA ( i i i ) HYPOTHETICAL: N ( i v ) ANTI-SENSE: N ( x i ) SEQUENCE DESCRIPTION: SEQ ID NO:88:

GTTAGATCTG  AGCTTGGTCC  C                                               2 1
```